United States Patent
Bowie et al.

(10) Patent No.: US 11,479,760 B2
(45) Date of Patent: Oct. 25, 2022

(54) BIOSYNTHETIC PLATFORM FOR THE PRODUCTION OF CANNABINOIDS AND OTHER PRENYLATED COMPOUNDS

(71) Applicant: The Regents of the University of California, Oakland, CA (US)

(72) Inventors: James U. Bowie, Los Angeles, CA (US); Meaghan Valliere, Leominster, MA (US); Tyler P. Korman, Sierra Madre, CA (US); Nicholas Woodall, Knoxville, TN (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/264,758

(22) PCT Filed: Aug. 1, 2019

(86) PCT No.: PCT/US2019/044752
§ 371 (c)(1),
(2) Date: Jan. 29, 2021

(87) PCT Pub. No.: WO2020/028722
PCT Pub. Date: Feb. 6, 2020

(65) Prior Publication Data
US 2021/0309975 A1    Oct. 7, 2021

Related U.S. Application Data

(60) Provisional application No. 62/713,348, filed on Aug. 1, 2018.

(51) Int. Cl.
| | |
|---|---|
| *C12P 17/06* | (2006.01) |
| *C12N 9/10* | (2006.01) |
| *C12P 7/22* | (2006.01) |
| *C12P 7/42* | (2006.01) |
| *C12P 9/00* | (2006.01) |

(52) U.S. Cl.
CPC .............. *C12N 9/1085* (2013.01); *C12P 7/22* (2013.01); *C12P 7/42* (2013.01); *C12P 9/00* (2013.01); *C12P 17/06* (2013.01); *C12Y 205/01039* (2013.01)

(58) Field of Classification Search
None
See application file for complete search history.

(56) References Cited

U.S. PATENT DOCUMENTS

2010/0285502 A1    11/2010    Kuzuyama et al.
2021/0309975 A1*   10/2021    Bowie ................. C12N 9/1085

FOREIGN PATENT DOCUMENTS

| CN | 113355300 A | 9/2021 |
|---|---|---|
| DE | 102010011601 A1 | 9/2011 |
| WO | 2006/081537 A2 | 8/2006 |
| WO | 2018/200888 A1 | 11/2018 |
| WO | 2019/173770 A1 | 9/2019 |
| WO | 2019/183152 A1 | 9/2019 |
| WO | 2020210810 A1 | 10/2020 |

OTHER PUBLICATIONS

International Search Report and Written Opinion, PCT/US2019/044752, United States Patent & Trademark Office, dated Jan. 9, 2020.
Valliere et al., "A cell-free platform for the prenylation of natural products and application to cannabinoid production," Nature Communicatons, vol. 10, p. 565, Feb. 4, 2019.
Yang et al., "Catalytic Mechanism of Aromatic Prenylation by NphB," Biochemistry, 51 (12):2606-2618, 2012.
Zocher et al., "Structure-Based Engineering Increased the Catalytic Turnover Rate of a Novel Phenazine Prenyltransferase," PLoS One, 7(10):e48427, 2012.
Nakamura, Yukari, International Preliminary Report on Patentability and Written Opinion, PCT/US2019/044752, The International Bureau of WIPO, dated Feb. 11, 2021.
Schonwasser, D., Partial Supplementary European Search Report, European Patent Office, Application No. 19843397.1, dated Apr. 11, 2022.
Schonwasser, D., Partial Supplementary European Search Report, European Patent Office, Application No. 19843397.1, dated Jun. 27, 2022.
Valliere et al., "A bio-inspired cell-free system for cannabinoid production from inexpensive inputs", Nature Chemical Biology, Aug. 24, 2020, vol. 16, No. 12, pp. 1427-1433.
Zirpel et al., "Engineering yeasts as platform organisms for cannabinoid biosynthesis", Journal of Biotechnology, Jul. 3, 2017, vol. 259, pp. 204-212.

* cited by examiner

*Primary Examiner* — Hope A Robinson
(74) *Attorney, Agent, or Firm* — Gavrilovich, Dodd & Lindsey LLP

(57) ABSTRACT

Provided is an enzyme useful for prenylation and recombinant pathways for the production of cannabinoids, cannabinoid precursors and other prenylated chemicals in a cell free system as well and recombinant microorganisms that catalyze the reactions.

12 Claims, 13 Drawing Sheets

Specification includes a Sequence Listing.

SEQUENCE LISTING

<160> NUMBER OF SEQ ID NOS: 83

<210> SEQ ID NO 1
<211> LENGTH: 327
<212> TYPE: PRT
<213> ORGANISM: Artificial Sequence
<220> FEATURE:
<223> OTHER INFORMATION: NphB M1

<400> SEQUENCE: 1

Met Gly Ser Ser His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
                100                 105                 110

Asp Leu Leu Ala Asp Thr Gln Lys His Leu Pro Val Ser Met Phe Ala
            115                 120                 125

Ile Asp Gly Glu Val Thr Gly Gly Phe Lys Lys Thr Tyr Ala Phe Phe
        130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Gly Ala Ala Tyr His Ile Thr Asp Val Gln Arg Gly Leu Leu Lys
305                 310                 315                 320

Ala Phe Asp Ser Leu Glu Asp
                325

<210> SEQ ID NO 2
<211> LENGTH: 327
<212> TYPE: PRT
<213> ORGANISM: Artificial Sequence
<220> FEATURE:
<223> OTHER INFORMATION: NphB M2

<400> SEQUENCE: 2

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
                100                 105                 110

Asp Leu Leu Ala Asp Thr Gln Lys His Leu Pro Val Ser Met Phe Ala
            115                 120                 125

```
Ile Asp Gly Glu Val Thr Gly Gly Phe Lys Lys Thr Tyr Ala Phe Phe
            130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Gly Ala Asn Tyr His Ile Thr Asp Val Gln Arg Gly Leu Leu Lys
305                 310                 315                 320

Ala Phe Asp Ser Leu Glu Asp
                325

<210> SEQ ID NO 3
<211> LENGTH: 327
<212> TYPE: PRT
<213> ORGANISM: Artificial Sequence
<220> FEATURE:
<223> OTHER INFORMATION: NphB M3

<400> SEQUENCE: 3

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160
```

```
Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser His Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Gly Ala Ala Tyr His Ile Thr Asp Val Gln Arg Gly Leu Leu Lys
305                 310                 315                 320

Ala Phe Asp Ser Leu Glu Asp
                325

<210> SEQ ID NO 4
<211> LENGTH: 327
<212> TYPE: PRT
<213> ORGANISM: Artificial Sequence
<220> FEATURE:
<223> OTHER INFORMATION: NphB M4

<400> SEQUENCE: 4

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190
```

```
Asn Leu Tyr Phe Ser Glu Leu Ser Ala Gln Thr Leu Glu Ala Glu Ser
            195                 200                 205

Val Leu Ala Leu Val Arg Glu Leu Gly Leu His Val Pro Asn Glu Leu
    210                 215                 220

Gly Leu Lys Phe Cys Lys Arg Ser Asn Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Gly Ala Ala Tyr His Ile Thr Asp Val Gln Arg Gly Leu Leu Lys
305                 310                 315                 320

Ala Phe Asp Ser Leu Glu Asp
                325

<210> SEQ ID NO 5
<211> LENGTH: 327
<212> TYPE: PRT
<213> ORGANISM: Artificial Sequence
<220> FEATURE:
<223> OTHER INFORMATION: NphB M5

<400> SEQUENCE: 5

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Ser Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220
```

```
Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Ile Ser Asn
            245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
            275                 280                 285

Thr Leu Val Tyr Gly Leu Thr Leu Ser Pro Lys Glu Glu Tyr Tyr Lys
            290                 295                 300

Leu Gly Ala Asn Tyr His Ile Thr Asp Val Gln Arg Gly Leu Leu Lys
305                 310                 315                 320

Ala Phe Asp Ser Leu Glu Asp
                325

<210> SEQ ID NO 6
<211> LENGTH: 327
<212> TYPE: PRT
<213> ORGANISM: Artificial Sequence
<220> FEATURE:
<223> OTHER INFORMATION: NpHB M6

<400> SEQUENCE: 6

Met Gly Ser Ser His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
            35                  40                  45

Lys Ile Tyr Pro Leu Leu Ser Thr Phe Gln Asp Thr Leu Val Glu Gly
        50                  55                  60

Gly Ser Val Val Asn Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
            115                 120                 125

Ile Asp Gly Glu Val Thr Gly Gly Phe Lys Lys Thr Tyr Ala Phe Phe
130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
            195                 200                 205

Val Leu Ala Leu Val Arg Glu Leu Gly Leu His Val Pro Asn Glu Leu
        210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Ile Ser Asn
            245                 250                 255
```

```
Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
            275                 280                 285

Thr Leu Val Tyr Gly Leu Thr Leu Ser Pro Lys Glu Glu Tyr Tyr Lys
            290                 295                 300

Leu Gly Ala Ser Tyr His Ile Thr Asp Val Gln Arg Gly Leu Leu Lys
305                 310                 315                 320

Ala Phe Asp Ser Leu Glu Asp
            325

<210> SEQ ID NO 7
<211> LENGTH: 327
<212> TYPE: PRT
<213> ORGANISM: Artificial
<220> FEATURE:
<223> OTHER INFORMATION: NphB M7

<400> SEQUENCE: 7

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
            35                  40                  45

Lys Ile Tyr Pro Leu Leu Ser Thr Phe Gln Asp Thr Leu Val Glu Gly
        50                  55                  60

Gly Ser Val Val Ser Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
            115                 120                 125

Ile Asp Gly Glu Val Thr Gly Gly Phe Lys Lys Thr Tyr Ala Phe Phe
130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
            165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
            195                 200                 205

Val Leu Ala Leu Val Arg Glu Leu Gly Leu His Val Pro Asn Glu Leu
            210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Ile Ser Asn
            245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
            275                 280                 285
```

Thr Leu Val Tyr Gly Leu Thr Leu Ser Pro Lys Glu Glu Tyr Tyr Lys
    290                 295                 300

Leu Gly Ala Ala Tyr His Ile Thr Asp Val Gln Arg Gly Leu Leu Lys
305                 310                 315                 320

Ala Phe Asp Ser Leu Glu Asp
                325

<210> SEQ ID NO 8
<211> LENGTH: 327
<212> TYPE: PRT
<213> ORGANISM: Artificial Sequence
<220> FEATURE:
<223> OTHER INFORMATION: NphB M8

<400> SEQUENCE: 8

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Thr Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Gly Ala Asn Tyr His Ile Thr Asp Val Gln Arg Gly Leu Leu Lys
305                 310                 315                 320

Ala Phe Asp Ser Leu Glu Asp
                325

<210> SEQ ID NO 9
<211> LENGTH: 327
<212> TYPE: PRT
<213> ORGANISM: Artificial Sequence
<220> FEATURE:
<223> OTHER INFORMATION: NphB M9

<400> SEQUENCE: 9

Met Gly Ser Ser His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Thr Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
290                 295                 300

Leu Gly Ala Asn Tyr His Ile Thr Asp Val Gln Arg Gly Leu Leu Lys
305                 310                 315                 320

Ala Phe Asp Ser Leu Glu Asp
                325

<210> SEQ ID NO 10

<211> LENGTH: 327
<212> TYPE: PRT
<213> ORGANISM: Artificial Sequence
<220> FEATURE:
<223> OTHER INFORMATION: NphB M10

<400> SEQUENCE: 10

```
Met Gly Ser Ser His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Ser Ala Asn Tyr His Ile Thr Asp Val Gln Arg Gly Leu Leu Lys
305                 310                 315                 320

Ala Phe Asp Ser Leu Glu Asp
                325
```

<210> SEQ ID NO 11
<211> LENGTH: 327
<212> TYPE: PRT
<213> ORGANISM: Artificial Sequence
<220> FEATURE:
<223> OTHER INFORMATION: NphB M11

```
<400> SEQUENCE: 11

Met Gly Ser Ser His His His His His Ser Ser Gly Leu Val Pro
1               5                   10                  15

Arg Gly Ser His Met Ser Glu Ala Ala Asp Val Glu Arg Val Tyr Ala
                20                  25                  30

Ala Met Glu Glu Ala Ala Gly Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Gly Phe Ser Met Ala Ser Gly Arg His Ser Thr Glu
65              70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Asn Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Gly Ala Asn Tyr His Ile Thr Asp Val Gln Arg Gly Leu Leu Lys
305                 310                 315                 320

Ala Phe Asp Ser Leu Glu Asp
                325

<210> SEQ ID NO 12
<211> LENGTH: 327
<212> TYPE: PRT
<213> ORGANISM: Artificial Sequence
<220> FEATURE:
<223> OTHER INFORMATION: NphB M12

<400> SEQUENCE: 12

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
```

```
            20                  25                  30
Ala Met Glu Glu Ala Ala Gly Leu Leu Gly Val Ala Cys Ala Arg Asp
            35                  40                  45

Lys Ile Tyr Pro Leu Leu Ser Thr Phe Gln Asp Thr Leu Val Glu Gly
    50                  55                  60

Gly Ser Val Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Asn Ser Val Tyr Pro Thr Leu Asn
225                 230                 235                 240

Trp Glu Thr Gly Lys Ile Asp Arg Leu Cys Phe Ala Val Thr Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Gly Ala Ala Tyr His Ile Thr Asp Val Gln Arg Gly Leu Leu Lys
305                 310                 315                 320

Ala Phe Asp Ser Leu Glu Asp
                325

<210> SEQ ID NO 13
<211> LENGTH: 327
<212> TYPE: PRT
<213> ORGANISM: Artificial Sequence
<220> FEATURE:
<223> OTHER INFORMATION: NphB M13

<400> SEQUENCE: 13

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
```

```
Gly Ser Val Val Asn Phe Ser Met Ala Ser Gly Arg His Ser Thr Glu
 65                  70                  75                  80

Leu Asp Phe Ser Ile Ser Val Pro Thr Ser His Gly Asp Pro Tyr Ala
                 85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
            115                 120                 125

Ile Asp Gly Glu Val Thr Gly Gly Phe Lys Lys Thr Tyr Ala Phe Phe
        130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Asn Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Gly Ala Ser Tyr His Ile Thr Asp Val Gln Arg Gly Leu Leu Lys
305                 310                 315                 320

Ala Phe Asp Ser Leu Glu Asp
                325

<210> SEQ ID NO 14
<211> LENGTH: 327
<212> TYPE: PRT
<213> ORGANISM: Artificial Sequence
<220> FEATURE:
<223> OTHER INFORMATION: NphB M14

<400> SEQUENCE: 14

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Val Phe Ser Met Ala Ser Gly Arg His Ser Thr Glu
 65                 70                  75                  80

Leu Asp Phe Ser Ile Ser Val Pro Thr Ser His Gly Asp Pro Tyr Ala
```

```
            85                  90                  95
Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
            115                 120                 125

Ile Asp Gly Glu Val Thr Gly Gly Phe Lys Lys Thr Tyr Ala Phe Phe
            130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
            165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
            195                 200                 205

Val Leu Ala Leu Val Arg Glu Leu Gly Leu His Val Pro Asn Glu Leu
            210                 215                 220

Gly Leu Lys Phe Cys Lys Arg Ser Gly Ser Val Tyr Pro Thr Leu Asn
225                 230                 235                 240

Trp Glu Thr Gly Lys Ile Asp Arg Leu Cys Phe Ala Val Thr Ser Asn
            245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
            275                 280                 285

Thr Leu Val Tyr Gly Leu Thr Leu Ser Pro Lys Glu Glu Tyr Tyr Lys
            290                 295                 300

Leu Gly Ala Asn Tyr His Ile Thr Asp Val Gln Arg Gly Leu Leu Lys
305                 310                 315                 320

Ala Phe Asp Ser Leu Glu Asp
            325

<210> SEQ ID NO 15
<211> LENGTH: 327
<212> TYPE: PRT
<213> ORGANISM: Artificial Sequence
<220> FEATURE:
<223> OTHER INFORMATION: NphB M15

<400> SEQUENCE: 15

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
            85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
```

```
            115                 120                 125
Ile Asp Gly Glu Val Thr Gly Gly Phe Lys Lys Thr Tyr Ala Phe Phe
            130                 135                 140
Pro Thr Asp Asn Met Pro Gly Val Ala Glu Leu Ser Ala Ile Pro Ser
145                 150                 155                 160
Met Pro Pro Ala Val Ala Glu Asn Ala Glu Leu Phe Ala Arg Tyr Gly
                    165                 170                 175
Leu Asp Lys Val Gln Met Thr Ser Met Asp Tyr Lys Lys Arg Gln Val
                180                 185                 190
Asn Leu Tyr Phe Ser Glu Leu Ser Ala Gln Thr Leu Glu Ala Glu Ser
                195                 200                 205
Val Leu Ala Leu Val Arg Glu Leu Gly Leu His Val Pro Asn Glu Leu
            210                 215                 220
Gly Leu Lys Phe Cys Lys Arg Ser Asn Ser Val Tyr Pro Thr Leu Asn
225                 230                 235                 240
Trp Glu Thr Gly Lys Ile Asp Arg Leu Cys Phe Ser Val Ile Ser Asn
                    245                 250                 255
Asp Pro Thr Leu Val Pro Ser Ser Asp Glu Gly Asp Ile Glu Lys Phe
                260                 265                 270
His Asn Tyr Ala Thr Lys Ala Pro Tyr Ala Tyr Val Gly Glu Lys Arg
                275                 280                 285
Thr Leu Val Tyr Gly Leu Thr Leu Ser Pro Lys Glu Glu Tyr Tyr Lys
            290                 295                 300
Leu Gly Ala Ala Tyr His Ile Thr Asp Val Gln Arg Gly Leu Leu Lys
305                 310                 315                 320
Ala Phe Asp Ser Leu Glu Asp
                    325

<210> SEQ ID NO 16
<211> LENGTH: 327
<212> TYPE: PRT
<213> ORGANISM: Artificial Sequence
<220> FEATURE:
<223> OTHER INFORMATION: NphB M16

<400> SEQUENCE: 16

Met Gly Ser Ser His His His His His His Ser Ser Gly Leu Val Pro
1               5                   10                  15
Arg Gly Ser His Met Ser Glu Ala Ala Asp Val Glu Arg Val Tyr Ala
                20                  25                  30
Ala Met Glu Glu Ala Ala Gly Leu Leu Gly Val Ala Cys Ala Arg Asp
            35                  40                  45
Lys Ile Tyr Pro Leu Leu Ser Thr Phe Gln Asp Thr Leu Val Glu Gly
        50                  55                  60
Gly Ser Val Val Val Phe Ser Met Ala Ser Gly Arg His Ser Thr Glu
65                  70                  75                  80
Leu Asp Phe Ser Ile Ser Val Pro Thr Ser His Gly Asp Pro Tyr Ala
                85                  90                  95
Thr Val Val Glu Lys Gly Leu Phe Pro Ala Thr Gly His Pro Val Asp
                100                 105                 110
Asp Leu Leu Ala Asp Thr Gln Lys His Leu Pro Val Ser Met Phe Ala
            115                 120                 125
Ile Asp Gly Glu Val Thr Gly Gly Phe Lys Lys Thr Tyr Ala Phe Phe
            130                 135                 140
Pro Thr Asp Asn Met Pro Gly Val Ala Glu Leu Ser Ala Ile Pro Ser
```

```
            145                 150                 155                 160
        Met Pro Pro Ala Val Ala Glu Asn Ala Glu Leu Phe Ala Arg Tyr Gly
                        165                 170                 175

Leu Asp Lys Val Gln Met Thr Ser Met Asp Tyr Lys Lys Arg Gln Val
                        180                 185                 190

Asn Leu Tyr Phe Ser Glu Leu Ser Ala Gln Thr Leu Glu Ala Glu Ser
                        195                 200                 205

Val Leu Ala Leu Val Arg Glu Leu Gly Leu His Val Pro Asn Glu Leu
                210                 215                 220

Gly Leu Lys Phe Cys Lys Arg Ser Asn Ser Val Tyr Pro Thr Leu Asn
        225                 230                 235                 240

Trp Glu Thr Gly Lys Ile Asp Arg Leu Cys Phe Ser Val Ile Ser Asn
                        245                 250                 255

Asp Pro Thr Leu Val Pro Ser Ser Asp Glu Gly Asp Ile Glu Lys Phe
                        260                 265                 270

His Asn Tyr Ala Thr Lys Ala Pro Tyr Ala Tyr Val Gly Glu Lys Arg
                        275                 280                 285

Thr Leu Val Tyr Gly Leu Thr Leu Ser Pro Lys Glu Glu Tyr Tyr Lys
                290                 295                 300

Leu Gly Ala Asn Tyr His Ile Thr Asp Val Gln Arg Gly Leu Leu Lys
        305                 310                 315                 320

Ala Phe Asp Ser Leu Glu Asp
                        325

<210> SEQ ID NO 17
        <211> LENGTH: 327
        <212> TYPE: PRT
        <213> ORGANISM: Artificial Sequence
        <220> FEATURE:
        <223> OTHER INFORMATION: NphB M17

<400> SEQUENCE: 17

Met Gly Ser Ser His His His His His His Ser Ser Gly Leu Val Pro
        1               5                   10                  15

Arg Gly Ser His Met Ser Glu Ala Ala Asp Val Glu Arg Val Tyr Ala
                        20                  25                  30

Ala Met Glu Glu Ala Ala Gly Leu Leu Gly Val Ala Cys Ala Arg Asp
                        35                  40                  45

Lys Ile Tyr Pro Leu Leu Ser Thr Phe Gln Asp Thr Leu Val Glu Gly
                50                  55                  60

Gly Ser Val Val Thr Phe Ser Met Ala Ser Gly Arg His Ser Thr Glu
        65                  70                  75                  80

Leu Asp Phe Ser Ile Ser Val Pro Thr Ser His Gly Asp Pro Tyr Ala
                        85                  90                  95

Thr Val Val Glu Lys Gly Leu Phe Pro Ala Thr Gly His Pro Val Asp
                        100                 105                 110

Asp Leu Leu Ala Asp Thr Gln Lys His Leu Pro Val Ser Met Phe Ala
                        115                 120                 125

Ile Asp Gly Glu Val Thr Gly Gly Phe Lys Lys Thr Tyr Ala Phe Phe
                130                 135                 140

Pro Thr Asp Asn Met Pro Gly Val Ala Glu Leu Ser Ala Ile Pro Ser
        145                 150                 155                 160

Met Pro Pro Ala Val Ala Glu Asn Ala Glu Leu Phe Ala Arg Tyr Gly
                        165                 170                 175

Leu Asp Lys Val Gln Met Thr Ser Met Asp Tyr Lys Lys Arg Gln Val
```

```
            180                 185                 190
Asn Leu Tyr Phe Ser Glu Leu Ser Ala Gln Thr Leu Glu Ala Glu Ser
                195                 200                 205

Val Leu Ala Leu Val Arg Glu Leu Gly Leu His Val Pro Asn Glu Leu
    210                 215                 220

Gly Leu Lys Phe Cys Lys Arg Ser Gly Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
            290                 295                 300

Leu Gly Ala Asn Tyr His Ile Thr Asp Val Gln Arg Gly Leu Leu Lys
305                 310                 315                 320

Ala Phe Asp Ser Leu Glu Asp
                325

<210> SEQ ID NO 18
<211> LENGTH: 327
<212> TYPE: PRT
<213> ORGANISM: Artificial Sequence
<220> FEATURE:
<223> OTHER INFORMATION: NphB M18

<400> SEQUENCE: 18

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Ser Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220
```

```
        210                 215                 220
Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Asn Tyr Gly Leu Thr Leu Ser Pro Lys Glu Glu Tyr Tyr Lys
    290                 295                 300

Leu Gly Ala Asn Tyr His Ile Thr Asp Val Gln Arg Gly Leu Leu Lys
305                 310                 315                 320

Ala Phe Asp Ser Leu Glu Asp
                325
```

<210> SEQ ID NO 19
<211> LENGTH: 327
<212> TYPE: PRT
<213> ORGANISM: Artificial Sequence
<220> FEATURE:
<223> OTHER INFORMATION: NphB M19

<400> SEQUENCE: 19

```
Met Gly Ser Ser His His His His His Ser Ser Gly Leu Val Pro
1               5                   10                  15

Arg Gly Ser His Met Ser Glu Ala Ala Asp Val Glu Arg Val Tyr Ala
                20                  25                  30

Ala Met Glu Glu Ala Ala Gly Leu Leu Gly Val Ala Cys Ala Arg Asp
            35                  40                  45

Lys Ile Tyr Pro Leu Leu Ser Thr Phe Gln Asp Thr Leu Val Glu Gly
        50                  55                  60

Gly Ser Val Val Ser Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Asn Ser Val Tyr Pro Thr Leu Asn
225                 230                 235                 240

Trp Glu Thr Gly Lys Ile Asp Arg Leu Cys Phe Ala Val Ile Ser Asn
```

```
                    245                 250                 255
Asp Pro Thr Leu Val Pro Ser Ser Asp Glu Gly Asp Ile Glu Lys Phe
                260                 265                 270
His Asn Tyr Ala Thr Lys Ala Pro Tyr Ala Tyr Val Gly Glu Lys Arg
                275                 280                 285
Thr Leu Asn Tyr Gly Leu Thr Leu Ser Pro Lys Glu Glu Tyr Tyr Lys
                290                 295                 300
Leu Gly Ala Asn Tyr His Ile Thr Asp Val Gln Arg Gly Leu Leu Lys
305                 310                 315                 320
Ala Phe Asp Ser Leu Glu Asp
                325

<210> SEQ ID NO 20
<211> LENGTH: 327
<212> TYPE: PRT
<213> ORGANISM: Artificial Sequence
<220> FEATURE:
<223> OTHER INFORMATION: NphB M20

<400> SEQUENCE: 20

Met Gly Ser Ser His His His His His His Ser Gly Leu Val Pro
1               5                   10                  15
Arg Gly Ser His Met Ser Glu Ala Ala Asp Val Glu Arg Val Tyr Ala
                20                  25                  30
Ala Met Glu Glu Ala Ala Gly Leu Leu Gly Val Ala Cys Ala Arg Asp
                35                  40                  45
Lys Ile Tyr Pro Leu Leu Ser Thr Phe Gln Asp Thr Leu Val Glu Gly
                50                  55                  60
Gly Ser Val Val Thr Phe Ser Met Ala Ser Gly Arg His Ser Thr Glu
65              70                  75                  80
Leu Asp Phe Ser Ile Ser Val Pro Thr Ser His Gly Asp Pro Tyr Ala
                85                  90                  95
Thr Val Val Glu Lys Gly Leu Phe Pro Ala Thr Gly His Pro Val Asp
                100                 105                 110
Asp Leu Leu Ala Asp Thr Gln Lys His Leu Pro Val Ser Met Phe Ala
                115                 120                 125
Ile Asp Gly Glu Val Thr Gly Gly Phe Lys Lys Thr Tyr Ala Phe Phe
                130                 135                 140
Pro Thr Asp Asn Met Pro Gly Val Ala Glu Leu Ser Ala Ile Pro Ser
145                 150                 155                 160
Met Pro Pro Ala Val Ala Glu Asn Ala Glu Leu Phe Ala Arg Tyr Gly
                165                 170                 175
Leu Asp Lys Val Gln Met Thr Ser Met Asp Tyr Lys Lys Arg Gln Val
                180                 185                 190
Asn Leu Tyr Phe Ser Glu Leu Ser Ala Gln Thr Leu Glu Ala Glu Ser
                195                 200                 205
Val Leu Ala Leu Val Arg Glu Leu Gly Leu His Val Pro Asn Glu Leu
                210                 215                 220
Gly Leu Lys Phe Cys Lys Arg Ser Gly Ser Val Tyr Pro Thr Leu Asn
225                 230                 235                 240
Trp Glu Thr Gly Lys Ile Asp Arg Leu Cys Phe Ala Val Ile Ser Asn
                245                 250                 255
Asp Pro Thr Leu Val Pro Ser Ser Asp Glu Gly Asp Ile Glu Lys Phe
                260                 265                 270
His Asn Tyr Ala Thr Lys Ala Pro Tyr Ala Tyr Val Gly Glu Lys Arg
```

```
            275                 280                 285
Thr Leu His Tyr Gly Leu Thr Leu Ser Pro Lys Glu Glu Tyr Tyr Lys
    290                 295                 300

Leu Gly Ala Asn Tyr His Ile Thr Asp Val Gln Arg Gly Leu Leu Lys
305                 310                 315                 320

Ala Phe Asp Ser Leu Glu Asp
                325

<210> SEQ ID NO 21
<211> LENGTH: 327
<212> TYPE: PRT
<213> ORGANISM: Artificial Sequence
<220> FEATURE:
<223> OTHER INFORMATION: NphB M21

<400> SEQUENCE: 21

Met Gly Ser Ser His His His His Ser Ser Gly Leu Val Pro
1               5                   10                  15

Arg Gly Ser His Met Ser Glu Ala Ala Asp Val Glu Arg Val Tyr Ala
                20                  25                  30

Ala Met Glu Glu Ala Ala Gly Leu Leu Gly Val Ala Cys Ala Arg Asp
            35                  40                  45

Lys Ile Tyr Pro Leu Leu Ser Thr Phe Gln Asp Thr Leu Val Glu Gly
    50                  55                  60

Gly Ser Val Val Ser Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Asn Ser Val Tyr Pro Thr Leu Asn
225                 230                 235                 240

Trp Glu Thr Gly Lys Ile Asp Arg Leu Cys Phe Ser Val Thr Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Asn Tyr Gly Leu Thr Leu Ser Pro Lys Glu Glu Tyr Tyr Lys
    290                 295                 300

Leu Gly Ala Asn Tyr His Ile Thr Asp Val Gln Arg Gly Leu Leu Lys
```

Ala Phe Asp Ser Leu Glu Asp
            325

<210> SEQ ID NO 22
<211> LENGTH: 327
<212> TYPE: PRT
<213> ORGANISM: Artificial Sequence
<220> FEATURE:
<223> OTHER INFORMATION: NphB M22

<400> SEQUENCE: 22

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Thr Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Gly Ser Val Tyr Pro Thr Leu Asn
225                 230                 235                 240

Trp Glu Thr Gly Lys Ile Asp Arg Leu Cys Phe Ala Val Thr Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu His Tyr Gly Leu Thr Leu Ser Pro Lys Glu Glu Tyr Tyr Lys
    290                 295                 300

Leu Gly Ala Asn Tyr His Ile Thr Asp Val Gln Arg Gly Ile Leu Lys
305                 310                 315                 320

Ala Phe Asp Ser Leu Glu Asp
            325

```
<210> SEQ ID NO 23
<211> LENGTH: 327
<212> TYPE: PRT
<213> ORGANISM: Artificial Sequence
<220> FEATURE:
<223> OTHER INFORMATION: NphB M23

<400> SEQUENCE: 23

Met Gly Ser Ser His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
    130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ala Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Ser Ala Ala Tyr His Ile Thr Asp Val Gln Arg Gly Leu Leu Lys
305                 310                 315                 320

Ala Phe Asp Ser Leu Glu Asp
                325

<210> SEQ ID NO 24
<211> LENGTH: 327
<212> TYPE: PRT
<213> ORGANISM: Artificial Sequence
<220> FEATURE:
<223> OTHER INFORMATION: NphB M24
```

<400> SEQUENCE: 24

```
Met Gly Ser Ser His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
        115                 120                 125

Ile Asp Gly Glu Val Thr Gly Gly Phe Lys Lys Thr Tyr Ala Phe Phe
130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ser Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Ser Ala Ala Tyr His Ile Thr Asp Val Gln Arg Gly Leu Leu Lys
305                 310                 315                 320

Ala Phe Asp Ser Leu Glu Asp
                325
```

<210> SEQ ID NO 25
<211> LENGTH: 327
<212> TYPE: PRT
<213> ORGANISM: Artificial Sequence
<220> FEATURE:
<223> OTHER INFORMATION: NphB M25

<400> SEQUENCE: 25

```
Met Gly Ser Ser His His His His His Ser Ser Gly Leu Val Pro
1               5                   10                  15
```

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
 50                  55                  60

Gly Ser Val Val Phe Ser Met Ala Ser Gly Arg His Ser Thr Glu
 65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
                100                 105                 110

Asp Leu Leu Ala Asp Thr Gln Lys His Leu Pro Val Ser Met Phe Ala
            115                 120                 125

Ile Asp Gly Glu Val Thr Gly Gly Phe Lys Lys Thr Tyr Ala Phe Phe
130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser His Ser Val Tyr Pro Thr Leu Asn
225                 230                 235                 240

Trp Glu Thr Gly Lys Ile Asp Arg Leu Cys Phe Ser Val Ile Ser Asn
                245                 250                 255

Asp Pro Thr Leu Val Pro Ser Ser Asp Glu Gly Asp Ile Glu Lys Phe
            260                 265                 270

His Asn Tyr Ala Thr Lys Ala Pro Tyr Ala Tyr Val Gly Glu Lys Arg
        275                 280                 285

Thr Leu Val Tyr Gly Leu Thr Leu Ser Pro Lys Glu Glu Tyr Tyr Lys
    290                 295                 300

Leu Ser Ala Ala Tyr His Ile Thr Asp Val Gln Arg Gly Leu Leu Lys
305                 310                 315                 320

Ala Phe Asp Ser Leu Glu Asp
                325

<210> SEQ ID NO 26
<211> LENGTH: 327
<212> TYPE: PRT
<213> ORGANISM: Artificial Sequence
<220> FEATURE:
<223> OTHER INFORMATION: NphB M27

<400> SEQUENCE: 26

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

```
Lys Ile Tyr Pro Leu Leu Ser Thr Phe Gln Asp Thr Leu Val Glu Gly
         50                  55                  60
Gly Ser Val Val Val Phe Ser Met Ala Ser Gly Arg His Ser Thr Glu
 65                  70                  75                  80
Leu Asp Phe Ser Ile Ser Val Pro Thr Ser His Gly Asp Pro Tyr Ala
                 85                  90                  95
Thr Val Val Glu Lys Gly Leu Phe Pro Ala Thr Gly His Pro Val Asp
                100                 105                 110
Asp Leu Leu Ala Asp Thr Gln Lys His Leu Pro Val Ser Met Phe Ala
                115                 120                 125
Ile Asp Gly Glu Val Thr Gly Gly Phe Lys Lys Thr Tyr Ala Phe Phe
130                 135                 140
Pro Thr Asp Asn Met Pro Gly Val Ala Glu Leu Ser Ala Ile Pro Ser
145                 150                 155                 160
Met Pro Pro Ala Val Ala Glu Asn Ala Glu Leu Phe Ala Arg Tyr Gly
                165                 170                 175
Leu Asp Lys Val Gln Met Thr Ser Met Asp Tyr Lys Lys Arg Gln Val
                180                 185                 190
Asn Leu Tyr Phe Ser Glu Leu Ser Ala Gln Thr Leu Glu Ala Glu Ser
                195                 200                 205
Val Leu Ala Leu Val Arg Glu Leu Gly Leu His Val Pro Asn Glu Leu
                210                 215                 220
Gly Leu Lys Phe Cys Lys Arg Ser Phe Ser Val Tyr Pro Thr Leu Asn
225                 230                 235                 240
Trp Glu Thr Gly Lys Ile Asp Arg Leu Cys Phe Ala Val Ile Ser Asn
                245                 250                 255
Asp Pro Thr Leu Val Pro Ser Ser Asp Glu Gly Asp Ile Glu Lys Phe
                260                 265                 270
His Asn Tyr Ala Thr Lys Ala Pro Tyr Ala Tyr Val Gly Glu Lys Arg
                275                 280                 285
Thr Leu Val Tyr Gly Leu Thr Leu Ser Pro Lys Glu Glu Tyr Tyr Lys
                290                 295                 300
Leu Ser Ala Val Tyr His Ile Thr Asp Val Gln Arg Gly Leu Leu Lys
305                 310                 315                 320
Ala Phe Asp Ser Leu Glu Asp
                325

<210> SEQ ID NO 27
<211> LENGTH: 327
<212> TYPE: PRT
<213> ORGANISM: Artificial Sequence
<220> FEATURE:
<223> OTHER INFORMATION: NphB M28

<400> SEQUENCE: 27

Met Gly Ser Ser His His His His His His Ser Ser Gly Leu Val Pro
 1               5                  10                  15
Arg Gly Ser His Met Ser Glu Ala Ala Asp Val Glu Arg Val Tyr Ala
                 20                  25                  30
Ala Met Glu Glu Ala Ala Gly Leu Leu Gly Val Ala Cys Ala Arg Asp
                 35                  40                  45
Lys Ile Tyr Pro Leu Leu Ser Thr Phe Gln Asp Thr Leu Val Glu Gly
         50                  55                  60
Gly Ser Val Val Val Phe Ser Met Ala Ser Gly Arg His Ser Thr Glu
 65                  70                  75                  80
```

```
Leu Asp Phe Ser Ile Ser Val Pro Thr Ser His Gly Asp Pro Tyr Ala
                85              90                  95
Thr Val Val Glu Lys Gly Leu Phe Pro Ala Thr Gly His Pro Val Asp
            100                 105                 110
Asp Leu Leu Ala Asp Thr Gln Lys His Leu Pro Val Ser Met Phe Ala
            115                 120                 125
Ile Asp Gly Glu Val Thr Gly Gly Phe Lys Lys Thr Tyr Ala Phe Phe
130                 135                 140
Pro Thr Asp Asn Met Pro Gly Val Ala Glu Leu Ser Ala Ile Pro Ser
145                 150                 155                 160
Met Pro Pro Ala Val Ala Glu Asn Ala Glu Leu Phe Ala Arg Tyr Gly
                165                 170                 175
Leu Asp Lys Val Gln Met Thr Ser Met Asp Tyr Lys Lys Arg Gln Val
            180                 185                 190
Asn Leu Tyr Phe Ser Glu Leu Ser Ala Gln Thr Leu Glu Ala Glu Ser
            195                 200                 205
Val Leu Ala Leu Val Arg Glu Leu Gly Leu His Val Pro Asn Glu Leu
        210                 215                 220
Gly Leu Lys Phe Cys Lys Arg Ser Phe Ser Val Tyr Pro Thr Leu Asn
225                 230                 235                 240
Trp Glu Thr Gly Lys Ile Asp Arg Leu Cys Phe Ser Val Ile Ser Asn
                245                 250                 255
Asp Pro Thr Leu Val Pro Ser Ser Asp Glu Gly Asp Ile Glu Lys Phe
            260                 265                 270
His Asn Tyr Ala Thr Lys Ala Pro Tyr Ala Tyr Val Gly Glu Lys Arg
            275                 280                 285
Thr Leu Val Tyr Gly Leu Thr Leu Ser Pro Lys Glu Glu Tyr Tyr Lys
        290                 295                 300
Leu Ser Ala Val Tyr His Ile Thr Asp Val Gln Arg Gly Leu Leu Lys
305                 310                 315                 320
Ala Phe Asp Ser Leu Glu Asp
                325

<210> SEQ ID NO 28
<211> LENGTH: 328
<212> TYPE: PRT
<213> ORGANISM: Artificial Sequence
<220> FEATURE:
<223> OTHER INFORMATION: NphB M30

<400> SEQUENCE: 28

Met Gly Ser Ser His His His His His His Ser Ser Gly Leu Val Pro
1               5                   10                  15
Arg Gly Ser His Met Ser Glu Ala Ala Asp Val Glu Arg Val Tyr Ala
            20                  25                  30
Ala Met Glu Glu Ala Ala Gly Leu Leu Gly Val Ala Cys Ala Arg Asp
        35                  40                  45
Lys Ile Tyr Pro Leu Leu Ser Thr Phe Gln Asp Thr Leu Val Glu Gly
    50                  55                  60
Gly Ser Val Val Val Phe Ser Met Ala Ser Gly Arg His Ser Thr Glu
65                  70                  75                  80
Leu Asp Phe Ser Ile Ser Val Pro Thr Ser His Gly Asp Pro Tyr Ala
                85                  90                  95
Thr Val Val Glu Lys Gly Leu Phe Pro Ala Thr Gly His Pro Val Asp
            100                 105                 110
```

```
Asp Leu Leu Ala Asp Thr Gln Lys His Leu Pro Val Ser Met Phe Ala
            115                 120                 125

Ile Asp Gly Glu Val Thr Gly Gly Phe Lys Lys Thr Tyr Ala Phe Phe
130                 135                 140

Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
        195                 200                 205

Val Leu Ala Leu Val Arg Glu Leu Gly Leu His Val Pro Asn Glu Leu
    210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ser Ala Val Ile Ser
                245                 250                 255

Asn Asp Pro Thr Leu Val Pro Ser Ser Asp Glu Gly Asp Ile Glu Lys
            260                 265                 270

Phe His Asn Tyr Ala Thr Lys Ala Pro Tyr Ala Tyr Val Gly Glu Lys
        275                 280                 285

Arg Thr Leu Val Tyr Gly Leu Thr Leu Ser Pro Lys Glu Glu Tyr Tyr
    290                 295                 300

Lys Leu Gly Ala Ala Tyr His Ile Thr Asp Val Gln Arg Gly Leu Leu
305                 310                 315                 320

Lys Ala Phe Asp Ser Leu Glu Asp
                325

<210> SEQ ID NO 29
<211> LENGTH: 328
<212> TYPE: PRT
<213> ORGANISM: Artificial Sequence
<220> FEATURE:
<223> OTHER INFORMATION: NphB M31

<400> SEQUENCE: 29

Met Gly Ser Ser His His His His His His Ser Ser Gly Leu Val Pro
1               5                   10                  15

Arg Gly Ser His Met Ser Glu Ala Ala Asp Val Glu Arg Val Tyr Ala
            20                  25                  30

Ala Met Glu Glu Ala Ala Gly Leu Leu Gly Val Ala Cys Ala Arg Asp
        35                  40                  45

Lys Ile Tyr Pro Leu Leu Ser Thr Phe Gln Asp Thr Leu Val Glu Gly
    50                  55                  60

Gly Ser Val Val Phe Ser Met Ala Ser Gly Arg His Ser Thr Glu
65                  70                  75                  80

Leu Asp Phe Ser Ile Ser Val Pro Thr Ser His Gly Asp Pro Tyr Ala
                85                  90                  95

Thr Val Val Glu Lys Gly Leu Phe Pro Ala Thr Gly His Pro Val Asp
            100                 105                 110

Asp Leu Leu Ala Asp Thr Gln Lys His Leu Pro Val Ser Met Phe Ala
            115                 120                 125

Ile Asp Gly Glu Val Thr Gly Gly Phe Lys Lys Thr Tyr Ala Phe Phe
130                 135                 140
```

```
Pro Thr Asp Asn Met Pro Gly Val Ala Glu Leu Ser Ala Ile Pro Ser
145                 150                 155                 160

Met Pro Pro Ala Val Ala Glu Asn Ala Glu Leu Phe Ala Arg Tyr Gly
                165                 170                 175

Leu Asp Lys Val Gln Met Thr Ser Met Asp Tyr Lys Lys Arg Gln Val
            180                 185                 190

Asn Leu Tyr Phe Ser Glu Leu Ser Ala Gln Thr Leu Glu Ala Glu Ser
            195                 200                 205

Val Leu Ala Leu Val Arg Glu Leu Gly Leu His Val Pro Asn Glu Leu
        210                 215                 220

Gly Leu Lys Phe Cys Lys Arg Ser Phe Ser Val Tyr Pro Thr Leu Asn
225                 230                 235                 240

Trp Glu Thr Gly Lys Ile Asp Arg Leu Cys Phe Ser Ala Val Ile Ser
                245                 250                 255

Asn Asp Pro Thr Leu Val Pro Ser Ser Asp Glu Gly Asp Ile Glu Lys
            260                 265                 270

Phe His Asn Tyr Ala Thr Lys Ala Pro Tyr Ala Tyr Val Gly Glu Lys
            275                 280                 285

Arg Thr Leu Val Tyr Gly Leu Thr Leu Ser Pro Lys Glu Glu Tyr Tyr
290                 295                 300

Lys Leu Gly Ala Val Tyr His Ile Thr Asp Val Gln Arg Gly Leu Leu
305                 310                 315                 320

Lys Ala Phe Asp Ser Leu Glu Asp
                325

<210> SEQ ID NO 30
<211> LENGTH: 307
<212> TYPE: PRT
<213> ORGANISM: Streptomyces sp.

<400> SEQUENCE: 30

Met Ser Glu Ala Ala Asp Val Glu Arg Val Tyr Ala Ala Met Glu Glu
1               5                   10                  15

Ala Ala Gly Leu Leu Gly Val Ala Cys Ala Arg Asp Lys Ile Tyr Pro
                20                  25                  30

Leu Leu Ser Thr Phe Gln Asp Thr Leu Val Glu Gly Gly Ser Val Val
            35                  40                  45

Val Phe Ser Met Ala Ser Gly Arg His Ser Thr Glu Leu Asp Phe Ser
        50                  55                  60

Ile Ser Val Pro Thr Ser His Gly Asp Pro Tyr Ala Thr Val Val Glu
65                  70                  75                  80

Lys Gly Leu Phe Pro Ala Thr Gly His Pro Val Asp Asp Leu Leu Ala
                85                  90                  95

Asp Thr Gln Lys His Leu Pro Val Ser Met Phe Ala Ile Asp Gly Glu
            100                 105                 110

Val Thr Gly Gly Phe Lys Lys Thr Tyr Ala Phe Phe Pro Thr Asp Asn
        115                 120                 125

Met Pro Gly Val Ala Glu Leu Ser Ala Ile Pro Ser Met Pro Pro Ala
    130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190
```

Val Arg Glu Leu Gly Leu His Val Pro Asn Glu Leu Gly Leu Lys Phe
    195                 200                 205

Cys Lys Arg Ser Phe Ser Val Tyr Pro Thr Leu Asn Trp Glu Thr Gly
210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
            245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Tyr
            275                 280                 285

Tyr His Ile Thr Asp Val Gln Arg Gly Leu Leu Lys Ala Phe Asp Ser
290                 295                 300

Leu Glu Asp
305

<210> SEQ ID NO 31
<211> LENGTH: 449
<212> TYPE: PRT
<213> ORGANISM: Geobacillus thermodenitrificans

<400> SEQUENCE: 31

Met Thr His Ile Arg Phe Asp Tyr Ser Lys Ala Leu Ala Phe Phe Gly
1               5                   10                  15

Glu His Glu Leu Thr Tyr Leu Arg Asp Ala Val Lys Val Ala His His
            20                  25                  30

Ser Leu His Glu Lys Thr Gly Val Gly Asn Asp Phe Leu Gly Trp Leu
        35                  40                  45

Asp Trp Pro Val Asn Tyr Asp Lys Glu Phe Ala Arg Ile Lys Gln
50                  55                  60

Ala Ala Lys Lys Ile Gln Ser Asp Ser Asp Val Leu Leu Val Ile Gly
65                  70                  75                  80

Ile Gly Gly Ser Tyr Leu Gly Ala Arg Ala Ala Ile Glu Met Leu His
                85                  90                  95

His Ser Phe Tyr Asn Ala Leu Pro Lys Glu Lys Arg Ser Thr Pro Gln
            100                 105                 110

Ile Ile Phe Val Gly Asn Asn Ile Ser Ser Thr Tyr Met Lys Asp Val
        115                 120                 125

Ile Asp Phe Leu Glu Gly Lys Asp Phe Ser Ile Asn Val Ile Ser Lys
130                 135                 140

Ser Gly Thr Thr Thr Glu Pro Ala Ile Ala Phe Arg Ile Phe Arg Lys
145                 150                 155                 160

Leu Leu Glu Asp Lys Tyr Gly Lys Glu Glu Ala Arg Arg Ile Tyr
            165                 170                 175

Ala Thr Thr Asp Arg Ala Arg Gly Ala Leu Arg Thr Leu Ala Asp Glu
            180                 185                 190

Glu Gly Tyr Glu Thr Phe Val Ile Pro Asp Asp Ile Gly Gly Arg Tyr
        195                 200                 205

Ser Val Leu Thr Ala Val Gly Leu Leu Pro Ile Ala Ala Ser Gly Ala
    210                 215                 220

Asp Ile Asp Ala Met Met Glu Gly Ala Ala Lys Ala Arg Glu Asp Phe
225                 230                 235                 240

Ser Arg Ser Glu Leu Glu Glu Asn Ala Ala Tyr Gln Tyr Ala Ala Ile

```
                    245                 250                 255
Arg Asn Ile Leu Tyr Asn Lys Gly Lys Thr Ile Glu Leu Leu Val Asn
            260                 265                 270

Tyr Glu Pro Ala Leu His Tyr Phe Ala Glu Trp Trp Lys Gln Leu Phe
        275                 280                 285

Gly Glu Ser Glu Gly Lys Asp Gln Lys Gly Ile Tyr Pro Ala Ser Ala
        290                 295                 300

Asp Phe Ser Thr Asp Leu His Ser Leu Gly Gln Tyr Ile Gln Glu Gly
305                 310                 315                 320

Arg Arg Asp Leu Phe Glu Thr Val Leu Lys Leu Glu Glu Pro Arg His
                325                 330                 335

Glu Leu Val Ile Glu Ala Glu Ser Asp Leu Asp Gly Leu Asn Tyr
            340                 345                 350

Leu Ala Gly Gln Thr Val Asp Phe Val Asn Thr Lys Ala Phe Glu Gly
            355                 360                 365

Thr Leu Leu Ala His Thr Asp Gly Gly Val Pro Asn Leu Val Val Thr
        370                 375                 380

Leu Pro Lys Leu Asp Glu Tyr Thr Phe Gly Tyr Leu Val Tyr Phe Phe
385                 390                 395                 400

Glu Lys Ala Cys Ala Met Ser Gly Tyr Leu Leu Gly Val Asn Pro Phe
                405                 410                 415

Asp Gln Pro Gly Val Glu Ala Tyr Lys Lys Asn Met Phe Ala Leu Leu
            420                 425                 430

Gly Lys Pro Gly Tyr Glu Glu Leu Lys Asp Glu Leu Glu Lys Arg Leu
            435                 440                 445

Lys

<210> SEQ ID NO 32
<211> LENGTH: 319
<212> TYPE: PRT
<213> ORGANISM: Geobacillus stearothermophilus

<400> SEQUENCE: 32

Met Lys Arg Ile Gly Val Leu Thr Ser Gly Gly Asp Ser Pro Gly Met
1               5                   10                  15

Asn Ala Ala Ile Arg Ser Val Val Arg Lys Ala Ile Tyr His Gly Val
            20                  25                  30

Glu Val Tyr Gly Val Tyr His Gly Tyr Ala Gly Leu Ile Ala Gly Asn
        35                  40                  45

Ile Lys Lys Leu Glu Val Gly Asp Val Gly Asp Ile Ile His Arg Gly
    50                  55                  60

Gly Thr Ile Leu Tyr Thr Ala Arg Cys Pro Glu Phe Lys Thr Glu Glu
65                  70                  75                  80

Gly Gln Lys Lys Gly Ile Glu Gln Leu Lys Lys His Gly Ile Glu Gly
                85                  90                  95

Leu Val Val Ile Gly Gly Asp Gly Ser Tyr Gln Gly Ala Lys Lys Leu
            100                 105                 110

Thr Glu His Gly Phe Pro Cys Val Gly Val Pro Gly Thr Ile Asp Asn
        115                 120                 125

Asp Ile Pro Gly Thr Asp Phe Thr Ile Gly Phe Asp Thr Ala Leu Asn
    130                 135                 140

Thr Val Ile Asp Ala Ile Asp Lys Ile Arg Asp Thr Ala Thr Ser His
145                 150                 155                 160

Glu Arg Thr Tyr Val Ile Glu Val Met Gly Arg His Ala Gly Asp Ile
```

```
                        165                 170                 175
Ala Leu Trp Ser Gly Leu Ala Gly Gly Ala Glu Thr Ile Leu Ile Pro
            180                 185                 190

Glu Ala Asp Tyr Asp Met Asn Asp Val Ile Ala Arg Leu Lys Arg Gly
            195                 200                 205

His Glu Arg Gly Lys Lys His Ser Ile Ile Val Ala Glu Gly Val
            210                 215                 220

Gly Ser Gly Val Asp Phe Gly Arg Gln Ile Gln Glu Ala Thr Gly Phe
225                 230                 235                 240

Glu Thr Arg Val Thr Val Leu Gly His Val Gln Arg Gly Gly Ser Pro
            245                 250                 255

Thr Ala Phe Asp Arg Val Leu Ala Ser Arg Leu Gly Ala Arg Ala Val
            260                 265                 270

Glu Leu Leu Leu Glu Gly Lys Gly Gly Arg Cys Val Gly Ile Gln Asn
            275                 280                 285

Asn Gln Leu Val Asp His Asp Ile Ala Glu Ala Leu Ala Asn Lys His
            290                 295                 300

Thr Ile Asp Gln Arg Met Tyr Ala Leu Ser Lys Glu Leu Ser Ile
305                 310                 315

<210> SEQ ID NO 33
<211> LENGTH: 309
<212> TYPE: PRT
<213> ORGANISM: Escherichia coli

<400> SEQUENCE: 33

Met Val Arg Ile Tyr Thr Leu Thr Leu Ala Pro Ser Leu Asp Ser Ala
1               5                   10                  15

Thr Ile Thr Pro Gln Ile Tyr Pro Glu Gly Lys Leu Arg Cys Thr Ala
            20                  25                  30

Pro Val Phe Glu Pro Gly Gly Gly Gly Ile Asn Val Ala Arg Ala Ile
            35                  40                  45

Ala His Leu Gly Gly Ser Ala Thr Ala Ile Phe Pro Ala Gly Gly Ala
        50                  55                  60

Thr Gly Glu His Leu Val Ser Leu Leu Ala Asp Glu Asn Val Pro Val
65                  70                  75                  80

Ala Thr Val Glu Ala Lys Asp Trp Thr Arg Gln Asn Leu His Val His
                85                  90                  95

Val Glu Ala Ser Gly Glu Gln Tyr Arg Phe Val Met Pro Gly Ala Ala
            100                 105                 110

Leu Asn Glu Asp Glu Phe Arg Gln Leu Glu Glu Gln Val Leu Glu Ile
            115                 120                 125

Glu Ser Gly Ala Ile Leu Val Ile Ser Gly Ser Leu Pro Pro Gly Val
        130                 135                 140

Lys Leu Glu Lys Leu Thr Gln Leu Ile Ser Ala Ala Lys Gln Gly
145                 150                 155                 160

Ile Arg Cys Ile Val Asp Ser Ser Gly Glu Ala Leu Ser Ala Ala Leu
                165                 170                 175

Ala Ile Gly Asn Ile Glu Leu Val Lys Pro Asn Gln Lys Glu Leu Ser
            180                 185                 190

Ala Leu Val Asn Arg Glu Leu Thr Gln Pro Asp Asp Val Arg Lys Ala
            195                 200                 205

Ala Gln Glu Ile Val Asn Ser Gly Lys Ala Lys Arg Val Val Val Ser
        210                 215                 220
```

-continued

```
Leu Gly Pro Gln Gly Ala Leu Gly Val Asp Ser Glu Asn Cys Ile Gln
225                 230                 235                 240

Val Val Pro Pro Val Lys Ser Gln Ser Thr Val Gly Ala Gly Asp
            245                 250                 255

Ser Met Val Gly Ala Met Thr Leu Lys Leu Ala Glu Asn Ala Ser Leu
        260                 265                 270

Glu Glu Met Val Arg Phe Gly Val Ala Ala Gly Ser Ala Ala Thr Leu
            275                 280                 285

Asn Gln Gly Thr Arg Leu Cys Ser His Asp Asp Thr Gln Lys Ile Tyr
290                 295                 300

Ala Tyr Leu Ser Arg
305
```

<210> SEQ ID NO 34
<211> LENGTH: 319
<212> TYPE: PRT
<213> ORGANISM: Geobacillus stearothermophilus

<400> SEQUENCE: 34

```
Met Lys Arg Ile Gly Val Leu Thr Ser Gly Gly Asp Ser Pro Gly Met
1               5                   10                  15

Asn Ala Ala Ile Arg Ser Val Val Arg Lys Ala Ile Tyr His Gly Val
            20                  25                  30

Glu Val Tyr Gly Val Tyr His Gly Tyr Ala Gly Leu Ile Ala Gly Asn
        35                  40                  45

Ile Lys Lys Leu Glu Val Gly Asp Val Gly Asp Ile Ile His Arg Gly
    50                  55                  60

Gly Thr Ile Leu Tyr Thr Ala Arg Cys Pro Glu Phe Lys Thr Glu Glu
65                  70                  75                  80

Gly Gln Lys Lys Gly Ile Glu Gln Leu Lys Lys His Gly Ile Glu Gly
                85                  90                  95

Leu Val Val Ile Gly Gly Asp Gly Ser Tyr Gln Gly Ala Lys Lys Leu
            100                 105                 110

Thr Glu His Gly Phe Pro Cys Val Gly Val Pro Gly Thr Ile Asp Asn
        115                 120                 125

Asp Ile Pro Gly Thr Asp Phe Thr Ile Gly Phe Asp Thr Ala Leu Asn
    130                 135                 140

Thr Val Ile Asp Ala Ile Asp Lys Ile Arg Asp Thr Ala Thr Ser His
145                 150                 155                 160

Glu Arg Thr Tyr Val Ile Glu Val Met Gly Arg His Ala Gly Asp Ile
                165                 170                 175

Ala Leu Trp Ser Gly Leu Ala Gly Gly Ala Glu Thr Ile Leu Ile Pro
            180                 185                 190

Glu Ala Asp Tyr Asp Met Asn Asp Val Ile Ala Arg Leu Lys Arg Gly
        195                 200                 205

His Glu Ala Gly Lys Lys His Ser Ile Ile Val Ala Glu Gly Val
    210                 215                 220

Gly Ser Gly Val Asp Phe Gly Arg Gln Ile Gln Glu Ala Thr Gly Phe
225                 230                 235                 240

Glu Thr Arg Val Thr Val Leu Gly His Val Gln Arg Gly Gly Ser Pro
                245                 250                 255

Thr Ala Phe Asp Arg Val Leu Ala Ser Arg Leu Gly Ala Arg Ala Val
            260                 265                 270

Glu Leu Leu Leu Glu Gly Lys Gly Gly Arg Cys Val Gly Ile Gln Asn
        275                 280                 285
```

-continued

Asn Gln Leu Val Asp His Asp Ile Ala Glu Ala Leu Ala Asn Lys His
            290                 295                 300

Thr Ile Asp Gln Arg Met Tyr Ala Leu Ser Lys Glu Leu Ser Ile
305                 310                 315

<210> SEQ ID NO 35
<211> LENGTH: 359
<212> TYPE: PRT
<213> ORGANISM: Escherichia coli

<400> SEQUENCE: 35

Met Ser Lys Ile Phe Asp Phe Val Lys Pro Gly Val Ile Thr Gly Asp
1               5                   10                  15

Asp Val Gln Lys Val Phe Gln Val Ala Lys Glu Asn Asn Phe Ala Leu
                20                  25                  30

Pro Ala Val Asn Cys Val Gly Thr Asp Ser Ile Asn Ala Val Leu Glu
            35                  40                  45

Thr Ala Ala Lys Val Lys Ala Pro Val Ile Val Gln Phe Ser Asn Gly
        50                  55                  60

Gly Ala Ser Phe Ile Ala Gly Lys Gly Val Lys Ser Asp Val Pro Gln
65                  70                  75                  80

Gly Ala Ala Ile Leu Gly Ala Ile Ser Gly Ala His His Val His Gln
                85                  90                  95

Met Ala Glu His Tyr Gly Val Pro Val Ile Leu His Thr Asp His Cys
            100                 105                 110

Ala Lys Lys Leu Leu Pro Trp Ile Asp Gly Leu Leu Asp Ala Gly Glu
        115                 120                 125

Lys His Phe Ala Ala Thr Gly Lys Pro Leu Phe Ser Ser His Met Ile
    130                 135                 140

Asp Leu Ser Glu Glu Ser Leu Gln Glu Asn Ile Glu Ile Cys Ser Lys
145                 150                 155                 160

Tyr Leu Glu Arg Met Ser Lys Ile Gly Met Thr Leu Glu Ile Glu Leu
                165                 170                 175

Gly Cys Thr Gly Gly Glu Glu Asp Gly Val Asp Asn Ser His Met Asp
            180                 185                 190

Ala Ser Ala Leu Tyr Thr Gln Pro Glu Asp Val Asp Tyr Ala Tyr Thr
        195                 200                 205

Glu Leu Ser Lys Ile Ser Pro Arg Phe Thr Ile Ala Ala Ser Phe Gly
    210                 215                 220

Asn Val His Gly Val Tyr Lys Pro Gly Asn Val Val Leu Thr Pro Thr
225                 230                 235                 240

Ile Leu Arg Asp Ser Gln Glu Tyr Val Ser Lys Lys His Asn Leu Pro
                245                 250                 255

His Asn Ser Leu Asn Phe Val Phe His Gly Gly Ser Gly Ser Thr Ala
            260                 265                 270

Gln Glu Ile Lys Asp Ser Val Ser Tyr Gly Val Val Lys Met Asn Ile
        275                 280                 285

Asp Thr Asp Thr Gln Trp Ala Thr Trp Glu Gly Val Leu Asn Tyr Tyr
    290                 295                 300

Lys Ala Asn Glu Ala Tyr Leu Gln Gly Gln Leu Gly Asn Pro Lys Gly
305                 310                 315                 320

Glu Asp Gln Pro Asn Lys Lys Tyr Tyr Asp Pro Arg Val Trp Leu Arg
                325                 330                 335

Ala Gly Gln Thr Ser Met Ile Ala Arg Leu Glu Lys Ala Phe Gln Glu

-continued

```
                  340                 345                 350

Leu Asn Ala Ile Asp Val Leu
        355

<210> SEQ ID NO 36
<211> LENGTH: 255
<212> TYPE: PRT
<213> ORGANISM: Escherichia coli

<400> SEQUENCE: 36

Met Arg His Pro Leu Val Met Gly Asn Trp Lys Leu Asn Gly Ser Arg
1               5                   10                  15

His Met Val His Glu Leu Val Ser Asn Leu Arg Lys Glu Leu Ala Gly
            20                  25                  30

Val Ala Gly Cys Ala Val Ala Ile Ala Pro Pro Glu Met Tyr Ile Asp
        35                  40                  45

Met Ala Lys Arg Glu Ala Glu Gly Ser His Ile Met Leu Gly Ala Gln
    50                  55                  60

Asn Val Asp Leu Asn Leu Ser Gly Ala Phe Thr Gly Glu Thr Ser Ala
65                  70                  75                  80

Ala Met Leu Lys Asp Ile Gly Ala Gln Tyr Ile Ile Gly His Ser
                85                  90                  95

Glu Arg Arg Thr Tyr His Lys Glu Ser Asp Glu Leu Ile Ala Lys Lys
            100                 105                 110

Phe Ala Val Leu Lys Glu Gln Gly Leu Thr Pro Val Leu Cys Ile Gly
        115                 120                 125

Glu Thr Glu Ala Glu Asn Glu Ala Gly Lys Thr Glu Glu Val Cys Ala
    130                 135                 140

Arg Gln Ile Asp Ala Val Leu Lys Thr Gln Gly Ala Ala Ala Phe Glu
145                 150                 155                 160

Gly Ala Val Ile Ala Tyr Glu Pro Val Trp Ala Ile Gly Thr Gly Lys
                165                 170                 175

Ser Ala Thr Pro Ala Gln Ala Gln Ala Val His Lys Phe Ile Arg Asp
            180                 185                 190

His Ile Ala Lys Val Asp Ala Asn Ile Ala Glu Gln Val Ile Ile Gln
        195                 200                 205

Tyr Gly Gly Ser Val Asn Ala Ser Asn Ala Ala Glu Leu Phe Ala Gln
    210                 215                 220

Pro Asp Ile Asp Gly Ala Leu Val Gly Gly Ala Ser Leu Lys Ala Asp
225                 230                 235                 240

Ala Phe Ala Val Ile Val Lys Ala Ala Glu Ala Ala Lys Gln Ala
                245                 250                 255

<210> SEQ ID NO 37
<211> LENGTH: 335
<212> TYPE: PRT
<213> ORGANISM: Geobacillus stearothermophilus

<400> SEQUENCE: 37

Met Ala Val Lys Val Gly Ile Asn Gly Phe Gly Arg Ile Gly Arg Asn
1               5                   10                  15

Val Phe Arg Ala Ala Leu Lys Asn Pro Asp Ile Glu Val Val Ala Val
            20                  25                  30

Asn Asp Leu Thr Asp Ala Asn Thr Leu Ala His Leu Leu Lys Tyr Asp
        35                  40                  45

Ser Val His Gly Arg Leu Asp Ala Glu Val Ser Val Asn Gly Asn Asn
```

```
Leu Val Asn Gly Lys Glu Ile Ile Val Lys Ala Glu Arg Asp Pro
 65                  70                  75                  80

Glu Asn Leu Ala Trp Gly Glu Ile Gly Val Asp Ile Val Glu Ser
                 85                  90                  95

Thr Gly Arg Phe Thr Lys Arg Glu Asp Ala Ala Lys His Leu Glu Ala
            100                 105                 110

Gly Ala Lys Lys Val Ile Ile Ser Ala Pro Ala Lys Asn Glu Asp Ile
            115                 120                 125

Thr Ile Val Met Gly Val Asn Gln Asp Lys Tyr Asp Pro Lys Ala His
    130                 135                 140

His Val Ile Ser Asn Ala Ser Cys Thr Thr Asn Cys Leu Ala Pro Phe
145                 150                 155                 160

Ala Lys Val Leu His Glu Gln Phe Gly Ile Val Arg Gly Met Met Thr
                165                 170                 175

Thr Val His Ser Tyr Thr Asn Asp Gln Arg Ile Leu Asp Leu Pro His
            180                 185                 190

Lys Asp Leu Arg Arg Ala Arg Ala Ala Ala Glu Ser Ile Ile Pro Thr
            195                 200                 205

Thr Thr Gly Ala Ala Lys Ala Val Ala Leu Val Leu Pro Glu Leu Lys
    210                 215                 220

Gly Lys Leu Asn Gly Met Ala Met Arg Val Pro Thr Pro Asn Val Ser
225                 230                 235                 240

Val Val Asp Leu Val Ala Glu Leu Glu Lys Glu Val Thr Val Glu Glu
                245                 250                 255

Val Asn Ala Ala Leu Lys Ala Ala Glu Gly Leu Lys Gly Ile
                260                 265                 270

Leu Ala Tyr Ser Glu Glu Pro Leu Val Ser Arg Asp Tyr Asn Gly Ser
            275                 280                 285

Thr Val Ser Ser Thr Ile Asp Ala Leu Ser Thr Met Val Ile Asp Gly
            290                 295                 300

Lys Met Val Lys Val Ser Trp Tyr Asp Asn Glu Thr Gly Tyr Ser
305                 310                 315                 320

His Arg Val Val Asp Leu Ala Ala Tyr Ile Ala Ser Lys Gly Leu
                325                 330                 335

<210> SEQ ID NO 38
<211> LENGTH: 335
<212> TYPE: PRT
<213> ORGANISM: Artificial Sequence
<220> FEATURE:
<223> OTHER INFORMATION: mGap Mutation P191D

<400> SEQUENCE: 38

Met Ala Val Lys Val Gly Ile Asn Gly Phe Gly Arg Ile Gly Arg Asn
 1               5                  10                  15

Val Phe Arg Ala Ala Leu Lys Asn Pro Asp Ile Glu Val Val Ala Val
                 20                  25                  30

Asn Asp Leu Thr Asp Ala Asn Thr Leu Ala His Leu Leu Lys Tyr Asp
             35                  40                  45

Ser Val His Gly Arg Leu Asp Ala Glu Val Ser Val Asn Gly Asn Asn
     50                  55                  60

Leu Val Val Asn Gly Lys Glu Ile Ile Val Lys Ala Glu Arg Asp Pro
 65                  70                  75                  80

Glu Asn Leu Ala Trp Gly Glu Ile Gly Val Asp Ile Val Glu Ser
```

```
                85                  90                  95
Thr Gly Arg Phe Thr Lys Arg Glu Asp Ala Ala Lys His Leu Glu Ala
                100                 105                 110
Gly Ala Lys Lys Val Ile Ile Ser Ala Pro Ala Lys Asn Glu Asp Ile
                115                 120                 125
Thr Ile Val Met Gly Val Asn Gln Asp Lys Tyr Asp Pro Lys Ala His
    130                 135                 140
His Val Ile Ser Asn Ala Ser Cys Thr Thr Asn Cys Leu Ala Pro Phe
145                 150                 155                 160
Ala Lys Val Leu His Glu Gln Phe Gly Ile Val Arg Gly Met Met Thr
                165                 170                 175
Thr Val His Ser Tyr Thr Asn Asp Gln Arg Ile Leu Asp Leu Asp His
                180                 185                 190
Lys Asp Leu Arg Arg Ala Arg Ala Ala Glu Ser Ile Ile Pro Thr
                195                 200                 205
Thr Thr Gly Ala Ala Lys Ala Val Ala Leu Val Leu Pro Glu Leu Lys
    210                 215                 220
Gly Lys Leu Asn Gly Met Ala Met Arg Val Pro Thr Pro Asn Val Ser
225                 230                 235                 240
Val Val Asp Leu Val Ala Glu Leu Glu Lys Glu Val Thr Val Glu Glu
                245                 250                 255
Val Asn Ala Ala Leu Lys Ala Ala Glu Gly Glu Leu Lys Gly Ile
                260                 265                 270
Leu Ala Tyr Ser Glu Glu Pro Leu Val Ser Arg Asp Tyr Asn Gly Ser
                275                 280                 285
Thr Val Ser Ser Thr Ile Asp Ala Leu Ser Thr Met Val Ile Asp Gly
    290                 295                 300
Lys Met Val Lys Val Val Ser Trp Tyr Asp Asn Glu Thr Gly Tyr Ser
305                 310                 315                 320
His Arg Val Val Asp Leu Ala Ala Tyr Ile Ala Ser Lys Gly Leu
                325                 330                 335

<210> SEQ ID NO 39
<211> LENGTH: 335
<212> TYPE: PRT
<213> ORGANISM: Artificial Sequence
<220> FEATURE:
<223> OTHER INFORMATION: mGap Mutation D34A/L35R/T36K

<400> SEQUENCE: 39

Met Ala Val Lys Val Gly Ile Asn Gly Phe Gly Arg Ile Gly Arg Asn
1               5                   10                  15
Val Phe Arg Ala Ala Leu Lys Asn Pro Asp Ile Glu Val Val Ala Val
                20                  25                  30
Asn Ala Arg Lys Asp Ala Asn Thr Leu Ala His Leu Leu Lys Tyr Asp
            35                  40                  45
Ser Val His Gly Arg Leu Asp Ala Glu Val Ser Val Asn Gly Asn Asn
        50                  55                  60
Leu Val Val Asn Gly Lys Glu Ile Ile Val Lys Ala Glu Arg Asp Pro
65                  70                  75                  80
Glu Asn Leu Ala Trp Gly Glu Ile Gly Val Asp Ile Val Glu Ser
                85                  90                  95
Thr Gly Arg Phe Thr Lys Arg Glu Asp Ala Ala Lys His Leu Glu Ala
                100                 105                 110
Gly Ala Lys Lys Val Ile Ile Ser Ala Pro Ala Lys Asn Glu Asp Ile
```

```
            115                 120                 125
Thr Ile Val Met Gly Val Asn Gln Asp Lys Tyr Asp Pro Lys Ala His
        130                 135                 140

His Val Ile Ser Asn Ala Ser Cys Thr Thr Asn Cys Leu Ala Pro Phe
145                 150                 155                 160

Ala Lys Val Leu His Glu Gln Phe Gly Ile Val Arg Gly Met Met Thr
                165                 170                 175

Thr Val His Ser Tyr Thr Asn Asp Gln Arg Ile Leu Asp Leu Pro His
            180                 185                 190

Lys Asp Leu Arg Arg Ala Arg Ala Ala Glu Ser Ile Ile Pro Thr
        195                 200                 205

Thr Thr Gly Ala Ala Lys Ala Val Ala Leu Val Leu Pro Glu Leu Lys
        210                 215                 220

Gly Lys Leu Asn Gly Met Ala Met Arg Val Pro Thr Pro Asn Val Ser
225                 230                 235                 240

Val Val Asp Leu Val Ala Glu Leu Glu Lys Glu Val Thr Val Glu Glu
                245                 250                 255

Val Asn Ala Ala Leu Lys Ala Ala Glu Gly Glu Leu Lys Gly Ile
            260                 265                 270

Leu Ala Tyr Ser Glu Glu Pro Leu Val Ser Arg Asp Tyr Asn Gly Ser
        275                 280                 285

Thr Val Ser Ser Thr Ile Asp Ala Leu Ser Thr Met Val Ile Asp Gly
        290                 295                 300

Lys Met Val Lys Val Ser Trp Tyr Asp Asn Glu Thr Gly Tyr Ser
305                 310                 315                 320

His Arg Val Val Asp Leu Ala Ala Tyr Ile Ala Ser Lys Gly Leu
                325                 330                 335

<210> SEQ ID NO 40
<211> LENGTH: 394
<212> TYPE: PRT
<213> ORGANISM: Geobacillus stearothermophilus

<400> SEQUENCE: 40

Met Asn Lys Lys Thr Ile Arg Asp Val Asp Val Arg Gly Lys Arg Val
1               5                   10                  15

Phe Cys Arg Val Asp Phe Asn Val Pro Met Glu Gln Gly Ala Ile Thr
            20                  25                  30

Asp Asp Thr Arg Ile Arg Ala Ala Leu Pro Thr Ile Arg Tyr Leu Ile
        35                  40                  45

Glu His Gly Ala Lys Val Ile Leu Ala Ser His Leu Gly Arg Pro Lys
    50                  55                  60

Gly Lys Val Val Glu Glu Leu Arg Leu Asp Ala Val Ala Lys Arg Leu
65                  70                  75                  80

Gly Glu Leu Leu Glu Arg Pro Val Ala Lys Thr Asn Glu Ala Val Gly
                85                  90                  95

Asp Glu Val Lys Ala Ala Val Asp Arg Leu Asn Glu Gly Asp Val Leu
            100                 105                 110

Leu Leu Glu Asn Val Arg Phe Tyr Pro Gly Glu Glu Lys Asn Asp Pro
        115                 120                 125

Glu Leu Ala Lys Ala Phe Ala Glu Leu Ala Asp Leu Tyr Val Asn Asp
    130                 135                 140

Ala Phe Gly Ala Ala His Arg Ala His Ala Ser Thr Glu Gly Ile Ala
145                 150                 155                 160
```

His Tyr Leu Pro Ala Val Ala Gly Phe Leu Met Glu Lys Glu Leu Glu
            165                 170                 175

Val Leu Gly Lys Ala Leu Ser Asn Pro Asp Arg Pro Phe Thr Ala Ile
        180                 185                 190

Ile Gly Gly Ala Lys Val Lys Asp Lys Ile Gly Val Ile Asp Asn Leu
        195                 200                 205

Leu Glu Lys Val Asp Asn Leu Ile Ile Gly Gly Leu Ala Tyr Thr
        210                 215                 220

Phe Val Lys Ala Leu Gly His Asp Val Gly Ser Leu Leu Glu Glu
225                 230                 235                 240

Asp Lys Ile Glu Leu Ala Lys Ser Phe Met Glu Lys Ala Lys Glu Lys
                245                 250                 255

Gly Val Arg Phe Tyr Met Pro Val Asp Val Val Ala Asp Arg Phe
                260                 265                 270

Ala Asn Asp Ala Asn Thr Lys Val Val Pro Ile Asp Ala Ile Pro Ala
            275                 280                 285

Asp Trp Ser Ala Leu Asp Ile Gly Pro Lys Thr Arg Glu Leu Tyr Arg
        290                 295                 300

Asp Val Ile Arg Glu Ser Lys Leu Val Val Trp Asn Gly Pro Met Gly
305                 310                 315                 320

Val Phe Glu Met Asp Ala Phe Ala His Gly Thr Lys Ala Ile Ala Glu
                325                 330                 335

Ala Leu Ala Glu Ala Leu Asp Thr Tyr Ser Val Ile Gly Gly Gly Asp
            340                 345                 350

Ser Ala Ala Ala Val Glu Lys Phe Gly Leu Ala Asp Lys Met Asp His
        355                 360                 365

Ile Ser Thr Gly Gly Gly Ala Ser Leu Glu Phe Met Glu Gly Lys Gln
        370                 375                 380

Leu Pro Gly Val Val Ala Leu Glu Asp Lys
385                 390

<210> SEQ ID NO 41
<211> LENGTH: 470
<212> TYPE: PRT
<213> ORGANISM: Geobacillus thermodenitrificans

<400> SEQUENCE: 41

Met Ala Lys Gln Gln Ile Gly Val Ile Gly Leu Ala Val Met Gly Lys
1               5                   10                  15

Asn Leu Ala Leu Asn Ile Glu Ser Arg Gly Tyr Ser Val Ala Val Tyr
            20                  25                  30

Asn Arg Ser Arg Glu Lys Thr Asp Glu Phe Leu Glu Glu Ala Lys Gly
        35                  40                  45

Lys Asn Ile Val Gly Thr Tyr Ser Ile Glu Glu Phe Val Asn Ala Leu
    50                  55                  60

Glu Lys Pro Arg Lys Ile Leu Leu Met Val Lys Ala Gly Ala Pro Thr
65                  70                  75                  80

Asp Ala Thr Ile Glu Gln Leu Lys Pro Tyr Leu Glu Lys Gly Asp Ile
                85                  90                  95

Leu Ile Asp Gly Gly Asn Thr Tyr Phe Lys Asp Thr Gln Arg Arg Asn
            100                 105                 110

Glu Glu Leu Ala Lys Leu Gly Ile His Phe Ile Gly Thr Gly Val Ser
        115                 120                 125

Gly Gly Glu Glu Gly Ala Leu Lys Gly Pro Ser Ile Met Pro Gly Gly
    130                 135                 140

Gln Lys Glu Ala His Glu Leu Val Arg Pro Ile Phe Glu Ala Ile Ala
145                 150                 155                 160

Ala Lys Val Asp Gly Glu Pro Cys Thr Thr Tyr Ile Gly Pro Asp Gly
                165                 170                 175

Ala Gly His Tyr Val Lys Met Val His Asn Gly Ile Tyr Gly Asp
            180                 185                 190

Met Gln Leu Ile Ala Glu Ala Tyr Phe Leu Leu Lys His Val Leu Gly
            195                 200                 205

Met Asp Ala Ala Glu Leu His Glu Val Phe Ala Asp Trp Asn Lys Gly
        210                 215                 220

Glu Leu Asn Ser Tyr Leu Ile Glu Ile Thr Ala Asp Ile Phe Thr Lys
225                 230                 235                 240

Ile Asp Asp Glu Thr Gly Lys Pro Leu Val Asp Val Ile Leu Asp Lys
                245                 250                 255

Ala Gly Gln Lys Gly Thr Gly Lys Trp Thr Ser Gln Asn Ala Leu Asp
            260                 265                 270

Leu Gly Val Pro Leu Pro Ile Ile Thr Glu Ser Val Phe Ala Arg Phe
        275                 280                 285

Ile Ser Ala Met Lys Asp Glu Arg Val Lys Ala Ser Lys Leu Leu Ser
290                 295                 300

Gly Pro Ala Val Lys Pro Phe Glu Gly Asp Arg Asp His Phe Ile Glu
305                 310                 315                 320

Ala Val Arg Arg Ala Leu Tyr Met Ser Lys Ile Cys Ser Tyr Ala Gln
                325                 330                 335

Gly Phe Ala Gln Met Lys Ala Ala Ser Asp Glu Tyr Asn Trp Asn Leu
            340                 345                 350

Arg Tyr Gly Asp Ile Ala Met Ile Phe Arg Gly Gly Cys Ile Ile Arg
        355                 360                 365

Ala Gln Phe Leu Gln Lys Ile Lys Glu Ala Tyr Asp Arg Asp Pro Ala
370                 375                 380

Leu Pro Asn Leu Leu Leu Asp Pro Tyr Phe Lys Asn Ile Val Glu Ser
385                 390                 395                 400

Tyr Gln Asp Ser Leu Arg Glu Ile Val Ala Thr Ala Ala Met Arg Gly
                405                 410                 415

Ile Pro Val Pro Ala Phe Ala Ser Ala Leu Ala Tyr Tyr Asp Ser Tyr
            420                 425                 430

Arg Asn Glu Val Leu Pro Ala Asn Leu Ile Gln Ala Gln Arg Asp Tyr
        435                 440                 445

Phe Gly Ala His Thr Tyr Glu Arg Val Asp Lys Glu Gly Ile Phe His
450                 455                 460

Thr Glu Trp Leu Ala Lys
465                 470

<210> SEQ ID NO 42
<211> LENGTH: 437
<212> TYPE: PRT
<213> ORGANISM: Escherichia coli

<400> SEQUENCE: 42

Met Ser Lys Ile Val Lys Ile Ile Gly Arg Glu Ile Ile Asp Ser Arg
1               5                   10                  15

Gly Asn Pro Thr Val Glu Ala Glu Val His Leu Glu Gly Gly Phe Val
            20                  25                  30

Gly Met Ala Ala Ala Pro Ser Gly Ala Ser Thr Gly Ser Arg Glu Ala

```
            35                  40                  45
Leu Glu Leu Arg Asp Gly Asp Lys Ser Arg Phe Leu Gly Lys Gly Val
 50                  55                  60

Thr Lys Ala Val Ala Val Asn Gly Pro Ile Ala Gln Ala Leu Ile
 65                  70                  75                  80

Gly Lys Asp Ala Lys Asp Gln Ala Gly Ile Asp Lys Ile Met Ile Asp
                 85                  90                  95

Leu Asp Gly Thr Glu Lys Lys Ser Lys Phe Gly Ala Asn Ala Ile Leu
                100                 105                 110

Ala Val Ser Leu Ala Asn Ala Lys Ala Ala Ala Lys Gly Met
            115                 120                 125

Pro Leu Tyr Glu His Ile Ala Glu Leu Asn Gly Thr Pro Gly Lys Tyr
            130                 135                 140

Ser Met Pro Val Pro Met Met Asn Ile Ile Asn Gly Gly Glu His Ala
145                 150                 155                 160

Asp Asn Asn Val Asp Ile Gln Glu Phe Met Ile Gln Pro Val Gly Ala
                165                 170                 175

Lys Thr Val Lys Glu Ala Ile Arg Met Gly Ser Glu Val Phe His His
                180                 185                 190

Leu Ala Lys Val Leu Lys Ala Lys Gly Met Asn Thr Ala Val Gly Asp
            195                 200                 205

Glu Gly Gly Tyr Ala Pro Asn Leu Gly Ser Asn Asp Glu Ala Leu Ala
210                 215                 220

Val Ile Ala Glu Ala Val Lys Ala Ala Gly Tyr Glu Leu Gly Lys Asp
225                 230                 235                 240

Ile Thr Leu Ala Met Asp Cys Ala Ala Ser Glu Phe Tyr Lys Asp Gly
                245                 250                 255

Lys Tyr Val Leu Ala Gly Glu Gly Asn Lys Ala Phe Thr Ser Glu Glu
                260                 265                 270

Phe Thr His Phe Leu Glu Glu Leu Thr Lys Gln Tyr Pro Ile Val Ser
            275                 280                 285

Ile Glu Asp Gly Leu Asp Glu Ser Asp Trp Asp Gly Phe Ala Tyr Gln
290                 295                 300

Thr Lys Val Leu Gly Asp Lys Ile Gln Leu Val Gly Asp Asp Leu Phe
305                 310                 315                 320

Val Thr Asn Thr Lys Ile Leu Lys Glu Gly Ile Glu Lys Gly Ile Ala
                325                 330                 335

Asn Ser Tyr Leu Ile Lys Phe Asn Gln Ile Gly Ser Leu Thr Glu Thr
            340                 345                 350

Leu Ala Ala Ile Lys Met Ala Lys Asp Ala Gly Tyr Thr Ala Val Ile
            355                 360                 365

Ser His Arg Ser Gly Glu Thr Glu Asp Ala Thr Ile Ala Asp Leu Ala
            370                 375                 380

Val Gly Thr Ala Ala Gly Gln Ile Lys Thr Gly Ser Met Ser Arg Ser
385                 390                 395                 400

Asp Arg Val Ala Lys Tyr Asn Gln Leu Ile Arg Ile Glu Glu Ala Leu
                405                 410                 415

Gly Glu Lys Ala Arg Thr Thr Val Val Lys Arg Ser Lys Ala Arg His
                420                 425                 430

Lys Thr Asp Phe Ile
            435

<210> SEQ ID NO 43
```

<211> LENGTH: 587
<212> TYPE: PRT
<213> ORGANISM: Geobacillus stearothermophilus

<400> SEQUENCE: 43

Met Lys Arg Lys Thr Lys Ile Val Cys Thr Ile Gly Pro Ala Ser Glu
1               5                   10                  15

Ser Val Asp Lys Leu Val Gln Leu Met Glu Ala Gly Met Asn Val Ala
            20                  25                  30

Arg Leu Asn Phe Ser His Gly Asp His Glu Glu His Gly Arg Arg Ile
        35                  40                  45

Ala Asn Ile Arg Glu Ala Ala Lys Arg Thr Gly Arg Thr Val Ala Ile
    50                  55                  60

Leu Leu Asp Thr Lys Gly Pro Glu Ile Arg Thr His Asn Met Glu Asn
65                  70                  75                  80

Gly Ala Ile Glu Leu Lys Glu Gly Ser Lys Leu Val Ile Ser Met Ser
                85                  90                  95

Glu Val Leu Gly Thr Pro Glu Lys Ile Ser Val Thr Tyr Pro Ser Leu
            100                 105                 110

Ile Asp Asp Val Ser Val Gly Ala Lys Ile Leu Leu Asp Asp Gly Leu
        115                 120                 125

Ile Ser Leu Glu Val Asn Ala Val Asp Lys Gln Ala Gly Glu Ile Val
    130                 135                 140

Thr Thr Val Leu Asn Gly Gly Val Leu Lys Asn Lys Lys Gly Val Asn
145                 150                 155                 160

Val Pro Gly Val Lys Val Asn Leu Pro Gly Ile Thr Glu Lys Asp Arg
                165                 170                 175

Ala Asp Ile Leu Phe Gly Ile Arg Gln Gly Ile Asp Phe Ile Ala Ala
            180                 185                 190

Ser Phe Val Arg Arg Ala Ser Asp Val Leu Glu Ile Arg Glu Leu Leu
        195                 200                 205

Glu Ala His Asp Ala Leu His Ile Gln Ile Ile Ala Lys Ile Glu Asn
    210                 215                 220

Glu Glu Gly Val Ala Asn Ile Asp Glu Ile Leu Glu Ala Ala Asp Gly
225                 230                 235                 240

Leu Met Val Ala Arg Gly Asp Leu Gly Val Glu Ile Pro Ala Glu Glu
                245                 250                 255

Val Pro Leu Ile Gln Lys Leu Leu Ile Lys Lys Cys Asn Met Leu Gly
            260                 265                 270

Lys Pro Val Ile Thr Ala Thr Gln Met Leu Asp Ser Met Gln Arg Asn
        275                 280                 285

Pro Arg Pro Thr Arg Ala Glu Ala Ser Asp Val Ala Asn Ala Ile Phe
    290                 295                 300

Asp Gly Thr Asp Ala Val Met Leu Ser Gly Glu Thr Ala Ala Gly Gln
305                 310                 315                 320

Tyr Pro Val Glu Ala Val Lys Thr Met His Gln Ile Ala Leu Arg Thr
                325                 330                 335

Glu Gln Ala Leu Glu His Arg Asp Ile Leu Ser Gln Arg Thr Lys Glu
            340                 345                 350

Ser Gln Thr Thr Ile Thr Asp Ala Ile Gly Gln Ser Val Ala His Thr
        355                 360                 365

Ala Leu Asn Leu Asp Val Ala Ala Ile Val Thr Pro Thr Val Ser Gly
    370                 375                 380

Lys Thr Pro Gln Met Val Ala Lys Tyr Arg Pro Lys Ala Pro Ile Ile

```
                385                 390                 395                 400
Ala Val Thr Ser Asn Glu Ala Val Ser Arg Arg Leu Ala Leu Val Trp
                    405                 410                 415
Gly Val Tyr Thr Lys Glu Ala Pro His Val Asn Thr Thr Asp Glu Met
                    420                 425                 430
Leu Asp Val Ala Val Asp Ala Val Arg Ser Gly Leu Val Lys His
                    435                 440                 445
Gly Asp Leu Val Val Ile Thr Ala Gly Val Pro Val Gly Glu Thr Gly
                    450                 455                 460
Ser Thr Asn Leu Met Lys Val His Val Ile Ser Asp Leu Leu Ala Lys
465                 470                 475                 480
Gly Gln Gly Ile Gly Arg Lys Ser Ala Phe Gly Lys Ala Val Val Ala
                    485                 490                 495
Lys Thr Ala Glu Glu Ala Arg Gln Lys Met Val Asp Gly Gly Ile Leu
                    500                 505                 510
Val Thr Val Ser Thr Asp Ala Asp Met Met Pro Ala Ile Glu Lys Ala
                    515                 520                 525
Ala Ala Ile Ile Thr Glu Glu Gly Gly Leu Thr Ser His Ala Ala Val
                    530                 535                 540
Val Gly Leu Ser Leu Gly Ile Pro Val Ile Val Gly Val Glu Asn Ala
545                 550                 555                 560
Thr Thr Leu Phe Lys Asp Gly Gln Glu Ile Thr Val Asp Gly Gly Phe
                    565                 570                 575
Gly Ala Val Tyr Arg Gly His Ala Ser Val Leu
                    580                 585

<210> SEQ ID NO 44
<211> LENGTH: 475
<212> TYPE: PRT
<213> ORGANISM: Zymomonas mobilis

<400> SEQUENCE: 44

Met Thr Glu Gly Leu Phe Pro Arg Gly Arg Lys Val Arg Val Val Ser
1                   5                   10                  15
Thr Leu Gly Pro Ala Ser Ser Thr Ala Glu Gln Ile Arg Asp Arg Phe
                    20                  25                  30
Leu Ala Gly Ala Asp Val Phe Arg Ile Asn Met Ser His Gly Thr His
                    35                  40                  45
Asp Glu Lys Lys Val Ile Val Asp Asn Ile Arg Ala Leu Glu Lys Glu
                    50                  55                  60
Phe Asn Arg Pro Thr Thr Ile Leu Phe Asp Leu Gln Gly Pro Lys Leu
65                  70                  75                  80
Arg Val Gly Asp Phe Lys Glu Gly Lys Val Gln Leu Lys Glu Gly Gln
                    85                  90                  95
Thr Phe Thr Phe Asp Gln Asp Pro Thr Leu Gly Asp Glu Thr Arg Val
                    100                 105                 110
Asn Leu Pro His Pro Glu Ile Phe Lys Ala Leu Asp Lys Gly His Arg
                    115                 120                 125
Leu Leu Leu Asp Asp Gly Lys Ile Val Val Arg Cys Val Glu Ser Ser
                    130                 135                 140
Pro Thr Lys Ile Val Thr Arg Val Glu Val Pro Gly Pro Leu Ser Asp
145                 150                 155                 160
His Lys Gly Phe Asn Val Pro Asp Val Val Ile Pro Leu Ala Ala Leu
                    165                 170                 175
```

-continued

```
Thr Pro Lys Asp Arg Lys Asp Leu Asp Phe Ala Leu Lys Glu Lys Ala
            180                 185                 190

Asp Trp Val Ala Leu Ser Phe Val Gln Arg Val Glu Asp Val Ile Glu
        195                 200                 205

Ala Lys Glu Leu Ile Lys Gly Arg Ala Pro Leu Leu Val Lys Leu Glu
    210                 215                 220

Lys Pro Ala Ala Ile Glu Asn Leu Glu Ser Ile Leu Ala Ala Thr Asp
225                 230                 235                 240

Ala Val Met Val Ala Arg Gly Asp Leu Gly Val Glu Cys Leu Pro Glu
                245                 250                 255

Ser Val Pro Pro Thr Gln Lys Arg Ile Val Glu Arg Ser Arg Gln Leu
            260                 265                 270

Gly Lys Pro Val Val Ala Thr Ala Met Leu Glu Ser Met Ile Lys
        275                 280                 285

Ala Pro Ala Pro Thr Arg Ala Glu Val Ser Asp Val Ala Asn Ala Ile
    290                 295                 300

Tyr Glu Gly Ala Asp Gly Ile Met Leu Ser Ala Glu Ser Ala Ala Gly
305                 310                 315                 320

Asp Trp Pro His Glu Ala Val Asn Met Met His Arg Ile Ala Ser Tyr
                325                 330                 335

Val Glu Asn Ala Pro Gly Tyr Ile Glu Arg Val Arg Phe Thr Pro Thr
            340                 345                 350

Pro Ala Glu Pro Thr Thr Val Asp Ala Leu Ala Glu Asn Ala Ser Lys
        355                 360                 365

Thr Ala Glu Thr Val Gly Ala Lys Ala Ile Ile Val Phe Thr Glu Thr
    370                 375                 380

Gly Lys Thr Ala Gln Arg Val Ser Arg Ala Arg Pro Val Ala Pro Ile
385                 390                 395                 400

Leu Ser Leu Thr Pro Asp Ala Glu Val Ala Arg Arg Leu Gly Leu Val
                405                 410                 415

Trp Gly Ala Gln Pro Val Gln Val Ser Thr Val Lys Thr Leu Asp Glu
            420                 425                 430

Ala Lys Lys Leu Ala Ala Glu Thr Ala Lys Lys Tyr Gly Phe Ala Lys
        435                 440                 445

Ala Gly Asp Lys Leu Val Val Val Ala Gly Glu Pro Phe Gly Lys Ala
    450                 455                 460

Gly Thr Thr Asn Ile Val Asp Val Ile Glu Ala
465                 470                 475

<210> SEQ ID NO 45
<211> LENGTH: 531
<212> TYPE: PRT
<213> ORGANISM: Oryctolagus cuniculus

<400> SEQUENCE: 45

Met Ser Lys Ser His Ser Glu Ala Gly Ser Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Ala Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Met Asn Phe Ser His Gly Thr
65                  70                  75                  80
```

```
His Glu Tyr His Ala Glu Thr Ile Lys Asn Val Arg Thr Ala Thr Glu
            85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
            115                 120                 125

Thr Ala Glu Val Glu Leu Lys Lys Gly Ala Thr Leu Lys Ile Thr Leu
            130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Asp Val Gly Ser Lys Val Tyr Val
                165                 170                 175

Asp Asp Gly Leu Ile Ser Leu Gln Val Lys Gln Lys Gly Pro Asp Phe
            180                 185                 190

Leu Val Thr Glu Val Glu Asn Gly Gly Phe Leu Gly Ser Lys Lys Gly
            195                 200                 205

Val Asn Leu Pro Gly Ala Ala Val Asp Leu Pro Ala Val Ser Glu Lys
            210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ala Asp Val His Glu Val Arg Lys
                245                 250                 255

Ile Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
            275                 280                 285

Gly Ile Met Val Ala Arg Gly Asp Leu Gly Ile Glu Ile Pro Ala Glu
            290                 295                 300

Lys Val Phe Leu Ala Gln Lys Met Ile Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
            355                 360                 365

Asp Tyr Pro Leu Glu Ala Val Arg Met Gln His Leu Ile Ala Arg Glu
            370                 375                 380

Ala Glu Ala Ala Met Phe His Arg Lys Leu Phe Glu Glu Leu Ala Arg
385                 390                 395                 400

Ala Ser Ser His Ser Thr Asp Leu Met Glu Ala Met Ala Met Gly Ser
                405                 410                 415

Val Glu Ala Ser Tyr Lys Cys Leu Ala Ala Ala Leu Ile Val Leu Thr
            420                 425                 430

Glu Ser Gly Arg Ser Ala His Gln Val Ala Arg Tyr Arg Pro Arg Ala
            435                 440                 445

Pro Ile Ile Ala Val Thr Arg Asn His Gln Thr Ala Arg Gln Ala His
            450                 455                 460

Leu Tyr Arg Gly Ile Phe Pro Val Val Cys Lys Asp Pro Val Gln Glu
465                 470                 475                 480

Ala Trp Ala Glu Asp Val Asp Leu Arg Val Asn Leu Ala Met Asn Val
                485                 490                 495
```

```
Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
        515                 520                 525

Pro Val Pro
    530

<210> SEQ ID NO 46
<211> LENGTH: 592
<212> TYPE: PRT
<213> ORGANISM: Aerococcus viridans

<400> SEQUENCE: 46

Met Ser Asp Asn Lys Ile Asn Ile Gly Leu Ala Val Met Lys Ile Leu
1               5                   10                  15

Glu Ser Trp Gly Ala Asp Thr Ile Tyr Gly Ile Pro Ser Gly Thr Leu
            20                  25                  30

Ser Ser Leu Met Asp Ala Met Gly Glu Glu Asn Asn Val Lys Phe
        35                  40                  45

Leu Gln Val Lys His Glu Val Gly Ala Met Ala Ala Val Met Gln
    50                  55                  60

Ser Lys Phe Gly Gly Asn Leu Gly Val Thr Val Gly Ser Gly Gly Pro
65                  70                  75                  80

Gly Ala Ser His Leu Ile Asn Gly Leu Tyr Asp Ala Ala Met Asp Asn
                85                  90                  95

Ile Pro Val Val Ala Ile Leu Gly Ser Arg Pro Gln Arg Glu Leu Asn
            100                 105                 110

Met Asp Ala Phe Gln Glu Leu Asn Gln Asn Pro Met Tyr Asp His Ile
        115                 120                 125

Ala Val Tyr Asn Arg Arg Val Ala Tyr Ala Glu Gln Leu Pro Lys Leu
    130                 135                 140

Val Asp Glu Ala Ala Arg Met Ala Ile Ala Lys Arg Gly Val Ala Val
145                 150                 155                 160

Leu Glu Val Pro Gly Asp Phe Ala Lys Val Glu Ile Asp Asn Asp Gln
                165                 170                 175

Trp Tyr Ser Ser Ala Asn Ser Leu Arg Lys Tyr Glu Pro Ile Ala Pro
            180                 185                 190

Ala Ala Gln Asp Ile Asp Ala Ala Val Glu Leu Leu Asn Asn Ser Lys
        195                 200                 205

Arg Pro Val Ile Tyr Ala Gly Ile Gly Thr Met Gly His Gly Pro Ala
    210                 215                 220

Val Gln Glu Leu Ala Arg Lys Ile Lys Ala Pro Val Ile Thr Thr Gly
225                 230                 235                 240

Lys Asn Phe Glu Thr Phe Glu Trp Asp Phe Glu Ala Leu Thr Gly Ser
                245                 250                 255

Thr Tyr Arg Val Gly Trp Lys Pro Ala Asn Glu Thr Ile Leu Glu Ala
            260                 265                 270

Asp Thr Val Leu Phe Ala Gly Ser Asn Phe Pro Phe Ser Glu Val Glu
        275                 280                 285

Gly Thr Phe Arg Asn Val Asp Asn Phe Ile Gln Ile Asp Ile Asp Pro
    290                 295                 300

Ala Met Leu Gly Lys Arg His His Ala Asp Val Ala Ile Leu Gly Asp
305                 310                 315                 320

Ala Gly Leu Ala Ile Asp Glu Ile Leu Asn Lys Val Asp Ala Val Glu
                325                 330                 335
```

Glu Ser Ala Trp Trp Thr Ala Asn Leu Lys Asn Ile Ala Asn Trp Arg
            340                 345                 350

Glu Tyr Ile Asn Met Leu Glu Thr Lys Glu Gly Asp Leu Gln Phe
        355                 360                 365

Tyr Gln Val Tyr Asn Ala Ile Asn Asn His Ala Asp Glu Asp Ala Ile
    370                 375                 380

Tyr Ser Ile Asp Val Gly Asn Ser Thr Gln Thr Ser Ile Arg His Leu
385                 390                 395                 400

His Met Thr Pro Lys Asn Met Trp Arg Thr Ser Pro Leu Phe Ala Thr
            405                 410                 415

Met Gly Ile Ala Ile Pro Gly Gly Leu Gly Ala Lys Asn Thr Tyr Pro
            420                 425                 430

Asp Arg Gln Val Trp Asn Ile Ile Gly Asp Gly Ala Phe Ser Met Thr
            435                 440                 445

Tyr Pro Asp Val Val Thr Asn Val Arg Tyr Asn Met Pro Val Ile Asn
    450                 455                 460

Val Val Phe Ser Asn Thr Glu Tyr Ala Phe Ile Lys Asn Lys Tyr Glu
465                 470                 475                 480

Asp Thr Asn Lys Asn Leu Phe Gly Val Asp Phe Thr Val Asp Tyr
            485                 490                 495

Ala Lys Ile Ala Glu Ala Gln Gly Ala Lys Gly Phe Thr Val Ser Arg
            500                 505                 510

Ile Glu Asp Met Asp Arg Val Met Ala Glu Ala Val Ala Ala Asn Lys
            515                 520                 525

Ala Gly His Thr Val Val Ile Asp Cys Lys Ile Thr Gln Asp Arg Pro
            530                 535                 540

Ile Pro Val Glu Thr Leu Lys Leu Asp Ser Lys Leu Tyr Ser Glu Asp
545                 550                 555                 560

Glu Ile Lys Ala Tyr Lys Glu Arg Tyr Glu Ala Ala Asn Leu Val Pro
                565                 570                 575

Phe Arg Glu Tyr Leu Glu Ala Glu Gly Leu Glu Ser Lys Tyr Ile Lys
            580                 585                 590

<210> SEQ ID NO 47
<211> LENGTH: 393
<212> TYPE: PRT
<213> ORGANISM: Cupriavidus necator H16

<400> SEQUENCE: 47

Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val
            20                  25                  30

Val Ile Lys Ala Ala Leu Glu Arg Ala Gly Val Lys Pro Glu Gln Val
        35                  40                  45

Ser Glu Val Ile Met Gly Gln Val Leu Thr Ala Gly Ser Gly Gln Asn
    50                  55                  60

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
                85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser

```
            115                 120                 125
Arg Asp Gly Phe Arg Met Gly Asp Ala Lys Leu Val Asp Thr Met Ile
    130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Gln Lys Ala
            180                 185                 190

Gly Lys Phe Asp Glu Glu Ile Val Pro Val Leu Ile Pro Gln Arg Lys
            195                 200                 205

Gly Asp Pro Val Ala Phe Lys Thr Asp Glu Phe Val Arg Gln Gly Ala
    210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
            275                 280                 285

Met Gly Met Gly Pro Val Pro Ala Ser Lys Arg Ala Leu Ser Arg Ala
    290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
            355                 360                 365

Arg Asp Ala Lys Lys Gly Leu Ala Ser Leu Cys Ile Gly Gly Gly Met
    370                 375                 380

Gly Val Ala Leu Ala Val Glu Arg Lys
385                 390

<210> SEQ ID NO 48
<211> LENGTH: 383
<212> TYPE: PRT
<213> ORGANISM: Enterococcus faecalis

<400> SEQUENCE: 48

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95
```

Gly Ile Gln Pro Phe Ala Arg Ser Phe Glu Ile Lys Glu Ala Cys Tyr
            100                 105                 110

Gly Ala Thr Ala Gly Leu Gln Leu Ala Lys Asn His Val Ala Leu His
        115                 120                 125

Pro Asp Lys Lys Val Leu Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
            260                 265                 270

Val Gly Asn Leu Tyr Thr Ser Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
            340                 345                 350

Glu Thr Leu Asp Thr Asp Ile Asp Gln Thr Leu Glu Asp Glu Leu Lys
        355                 360                 365

Tyr Ser Ile Ser Ala Ile Asn Asn Thr Val Arg Ser Tyr Arg Asn
370                 375                 380

<210> SEQ ID NO 49
<211> LENGTH: 803
<212> TYPE: PRT
<213> ORGANISM: Enterococcus faecalis

<400> SEQUENCE: 49

Met Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

```
Leu Ala Lys Gln Leu Ile Gln Leu Gly Glu Ala Glu Val Leu Ile Ala
             100                 105                 110
Gly Gly Ile Glu Asn Met Ser Gln Ala Pro Lys Leu Gln Arg Phe Asn
             115                 120                 125
Tyr Glu Thr Glu Ser Tyr Asp Ala Pro Phe Ser Ser Met Met Tyr Asp
             130                 135                 140
Gly Leu Thr Asp Ala Phe Ser Gly Gln Ala Met Gly Leu Thr Ala Glu
145                 150                 155                 160
Asn Val Ala Glu Lys Tyr His Val Thr Arg Glu Gln Asp Gln Phe
                 165                 170                 175
Ser Val His Ser Gln Leu Lys Ala Ala Gln Ala Gln Ala Glu Gly Ile
             180                 185                 190
Phe Ala Asp Glu Ile Ala Pro Leu Glu Val Ser Gly Thr Leu Val Glu
             195                 200                 205
Lys Asp Glu Gly Ile Arg Pro Asn Ser Ser Val Glu Lys Leu Gly Thr
210                 215                 220
Leu Lys Thr Val Phe Lys Glu Asp Gly Thr Val Thr Ala Gly Asn Ala
225                 230                 235                 240
Ser Thr Ile Asn Asp Gly Ala Ser Ala Leu Ile Ile Ala Ser Gln Glu
             245                 250                 255
Tyr Ala Glu Ala His Gly Leu Pro Tyr Leu Ala Ile Ile Arg Asp Ser
             260                 265                 270
Val Glu Val Gly Ile Asp Pro Ala Tyr Met Gly Ile Ser Pro Ile Lys
             275                 280                 285
Ala Ile Gln Lys Leu Leu Ala Arg Asn Gln Leu Thr Thr Glu Glu Ile
             290                 295                 300
Asp Leu Tyr Glu Ile Asn Glu Ala Phe Ala Ala Thr Ser Ile Val Val
305                 310                 315                 320
Gln Arg Glu Leu Ala Leu Pro Glu Glu Lys Val Asn Ile Tyr Gly Gly
             325                 330                 335
Gly Ile Ser Leu Gly His Ala Ile Gly Ala Thr Gly Ala Arg Leu Leu
             340                 345                 350
Thr Ser Leu Ser Tyr Gln Leu Asn Gln Lys Glu Lys Tyr Gly Val
             355                 360                 365
Ala Ser Leu Cys Ile Gly Gly Gly Leu Gly Leu Ala Met Leu Leu Glu
             370                 375                 380
Arg Pro Gln Gln Lys Lys Asn Ser Arg Phe Tyr Gln Met Ser Pro Glu
385                 390                 395                 400
Glu Arg Leu Ala Ser Leu Leu Asn Glu Gly Gln Ile Ser Ala Asp Thr
             405                 410                 415
Lys Lys Glu Phe Glu Asn Thr Ala Leu Ser Ser Gln Ile Ala Asn His
             420                 425                 430
Met Ile Glu Asn Gln Ile Ser Glu Thr Glu Val Pro Met Gly Val Gly
             435                 440                 445
Leu His Leu Thr Val Asp Glu Thr Asp Tyr Leu Val Pro Met Ala Thr
             450                 455                 460
Glu Glu Pro Ser Val Ile Ala Ala Leu Ser Asn Gly Ala Lys Ile Ala
465                 470                 475                 480
Gln Gly Phe Lys Thr Val Asn Gln Gln Arg Leu Met Arg Gly Gln Ile
             485                 490                 495
Val Phe Tyr Asp Val Ala Asp Ala Glu Ser Leu Ile Asp Glu Leu Gln
             500                 505                 510
```

Val Arg Glu Thr Glu Ile Phe Gln Gln Ala Glu Leu Ser Tyr Pro Ser
            515                 520                 525

Ile Val Lys Arg Gly Gly Leu Arg Asp Leu Gln Tyr Arg Ala Phe
    530                 535                 540

Asp Glu Ser Phe Val Ser Val Asp Phe Leu Val Asp Val Lys Asp Ala
545                 550                 555                 560

Met Gly Ala Asn Ile Val Asn Ala Met Leu Glu Gly Val Ala Glu Leu
                565                 570                 575

Phe Arg Glu Trp Phe Ala Glu Gln Lys Ile Leu Phe Ser Ile Leu Ser
                580                 585                 590

Asn Tyr Ala Thr Glu Ser Val Val Thr Met Lys Thr Ala Ile Pro Val
            595                 600                 605

Ser Arg Leu Ser Lys Gly Ser Asn Gly Arg Glu Ile Ala Glu Lys Ile
            610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
                645                 650                 655

Gly Asn Asp Thr Arg Ala Val Ser Ala Ser Cys His Ala Phe Ala Val
            660                 665                 670

Lys Glu Gly Arg Tyr Gln Gly Leu Thr Ser Trp Thr Leu Asp Gly Glu
            675                 680                 685

Gln Leu Ile Gly Glu Ile Ser Val Pro Leu Ala Leu Ala Thr Val Gly
            690                 695                 700

Gly Ala Thr Lys Val Leu Pro Lys Ser Gln Ala Ala Asp Leu Leu
705                 710                 715                 720

Ala Val Thr Asp Ala Lys Glu Leu Ser Arg Val Val Ala Ala Val Gly
                725                 730                 735

Leu Ala Gln Asn Leu Ala Ala Leu Arg Ala Leu Val Ser Glu Gly Ile
            740                 745                 750

Gln Lys Gly His Met Ala Leu Gln Ala Arg Ser Leu Ala Met Thr Val
            755                 760                 765

Gly Ala Thr Gly Lys Glu Val Glu Ala Val Ala Gln Gln Leu Lys Arg
            770                 775                 780

Gln Lys Thr Met Asn Gln Asp Arg Ala Leu Ala Ile Leu Asn Asp Leu
785                 790                 795                 800

Arg Lys Gln

<210> SEQ ID NO 50
<211> LENGTH: 301
<212> TYPE: PRT
<213> ORGANISM: Methanosarcina mazei Go1

<400> SEQUENCE: 50

Met Val Ser Cys Ser Ala Pro Gly Lys Ile Tyr Leu Phe Gly Glu His
1               5                   10                  15

Ala Val Val Tyr Gly Glu Thr Ala Ile Ala Cys Ala Val Glu Leu Arg
                20                  25                  30

Thr Arg Val Arg Ala Glu Leu Asn Asp Ser Ile Thr Ile Gln Ser Gln
            35                  40                  45

Ile Gly Arg Thr Gly Leu Asp Phe Glu Lys His Pro Tyr Val Ser Ala
        50                  55                  60

Val Ile Glu Lys Met Arg Lys Ser Ile Pro Ile Asn Gly Val Phe Leu
65                  70                  75                  80

```
Thr Val Asp Ser Asp Ile Pro Val Gly Ser Gly Leu Gly Ser Ser Ala
                85                  90                  95

Ala Val Thr Ile Ala Ser Ile Gly Ala Leu Asn Glu Leu Phe Gly Phe
            100                 105                 110

Gly Leu Ser Leu Gln Glu Ile Ala Lys Leu Gly His Glu Ile Glu Ile
            115                 120                 125

Lys Val Gln Gly Ala Ala Ser Pro Thr Asp Thr Tyr Val Ser Thr Phe
            130                 135                 140

Gly Gly Val Val Thr Ile Pro Glu Arg Arg Lys Leu Lys Thr Pro Asp
145                 150                 155                 160

Cys Gly Ile Val Ile Gly Asp Thr Gly Val Phe Ser Ser Thr Lys Glu
                165                 170                 175

Leu Val Ala Asn Val Arg Gln Leu Arg Glu Ser Tyr Pro Asp Leu Ile
                180                 185                 190

Glu Pro Leu Met Thr Ser Ile Gly Lys Ile Ser Arg Ile Gly Glu Gln
            195                 200                 205

Leu Val Leu Ser Gly Asp Tyr Ala Ser Ile Gly Arg Leu Met Asn Val
    210                 215                 220

Asn Gln Gly Leu Leu Asp Ala Leu Gly Val Asn Ile Leu Glu Leu Ser
225                 230                 235                 240

Gln Leu Ile Tyr Ser Ala Arg Ala Ala Gly Ala Phe Gly Ala Lys Ile
                245                 250                 255

Thr Gly Ala Gly Gly Gly Cys Met Val Ala Leu Thr Ala Pro Glu
            260                 265                 270

Lys Cys Asn Gln Val Ala Glu Ala Val Ala Gly Ala Gly Lys Val
            275                 280                 285

Thr Ile Thr Lys Pro Thr Glu Gln Gly Leu Lys Val Asp
    290                 295                 300

<210> SEQ ID NO 51
<211> LENGTH: 335
<212> TYPE: PRT
<213> ORGANISM: Streptococcus pneumoniae

<400> SEQUENCE: 51

Met Ile Ala Val Lys Thr Cys Gly Lys Leu Tyr Trp Ala Gly Glu Tyr
1               5                   10                  15

Ala Ile Leu Glu Pro Gly Gln Leu Ala Leu Ile Lys Asp Ile Pro Ile
            20                  25                  30

Tyr Met Arg Ala Glu Ile Ala Phe Ser Asp Ser Tyr Arg Ile Tyr Ser
        35                  40                  45

Asp Met Phe Asp Phe Ala Val Asp Leu Arg Pro Asn Pro Asp Tyr Ser
    50                  55                  60

Leu Ile Gln Glu Thr Ile Ala Leu Met Gly Asp Phe Leu Ala Val Arg
65                  70                  75                  80

Gly Gln Asn Leu Arg Pro Phe Ser Leu Ala Ile Tyr Gly Lys Met Glu
                85                  90                  95

Arg Glu Gly Lys Lys Phe Gly Leu Gly Ser Ser Gly Ser Val Val Val
            100                 105                 110

Leu Val Val Lys Ala Leu Leu Ala Leu Tyr Asn Leu Ser Val Asp Gln
            115                 120                 125

Asn Leu Leu Phe Lys Leu Thr Ser Ala Val Leu Leu Lys Arg Gly Asp
        130                 135                 140

Asn Gly Ser Met Gly Asp Leu Ala Cys Ile Ala Ala Glu Asp Leu Val
145                 150                 155                 160
```

```
Leu Tyr Gln Ser Phe Asp Arg Gln Lys Val Ala Ala Trp Leu Glu Glu
                165                 170                 175

Glu Asn Leu Ala Thr Val Leu Glu Arg Asp Trp Gly Phe Ser Ile Ser
            180                 185                 190

Gln Val Lys Pro Thr Leu Glu Cys Asp Phe Leu Val Gly Trp Thr Lys
        195                 200                 205

Glu Val Ala Val Ser Ser His Met Val Gln Gln Ile Lys Gln Asn Ile
    210                 215                 220

Asn Gln Asn Phe Leu Thr Ser Ser Lys Glu Thr Val Val Ser Leu Val
225                 230                 235                 240

Glu Ala Leu Glu Gln Gly Lys Ser Glu Lys Ile Ile Glu Gln Val Glu
                245                 250                 255

Val Ala Ser Lys Leu Leu Glu Gly Leu Ser Thr Asp Ile Tyr Thr Pro
            260                 265                 270

Leu Leu Arg Gln Leu Lys Glu Ala Ser Gln Asp Leu Gln Ala Val Ala
        275                 280                 285

Lys Ser Ser Gly Ala Gly Gly Asp Cys Gly Ile Ala Leu Ser Phe
    290                 295                 300

Asp Ala Gln Ser Thr Lys Thr Leu Lys Asn Arg Trp Ala Asp Leu Gly
305                 310                 315                 320

Ile Glu Leu Leu Tyr Gln Glu Arg Ile Gly His Asp Asp Lys Ser
                325                 330                 335

<210> SEQ ID NO 52
<211> LENGTH: 344
<212> TYPE: PRT
<213> ORGANISM: Streptococcus pneumoniae

<400> SEQUENCE: 52

Met Tyr His Ser Leu Gly Asn Gln Phe Asp Thr Arg Thr Arg Thr Ser
1               5                   10                  15

Arg Lys Ile Arg Arg Glu Arg Ser Cys Ser Asp Met Asp Arg Glu Pro
            20                  25                  30

Val Thr Val Arg Ser Tyr Ala Asn Ile Ala Ile Ile Lys Tyr Trp Gly
        35                  40                  45

Lys Lys Lys Glu Lys Glu Met Val Pro Ala Thr Ser Ser Ile Ser Leu
    50                  55                  60

Thr Leu Glu Asn Met Tyr Thr Glu Thr Thr Leu Ser Pro Leu Pro Ala
65                  70                  75                  80

Asn Val Thr Ala Asp Glu Phe Tyr Ile Asn Gly Gln Leu Gln Asn Glu
                85                  90                  95

Val Glu His Ala Lys Met Ser Lys Ile Ile Asp Arg Tyr Arg Pro Ala
            100                 105                 110

Gly Glu Gly Phe Val Arg Ile Asp Thr Gln Asn Asn Met Pro Thr Ala
        115                 120                 125

Ala Gly Leu Ser Ser Ser Ser Gly Leu Ser Ala Leu Val Lys Ala
    130                 135                 140

Cys Asn Ala Tyr Phe Lys Leu Gly Leu Asp Arg Ser Gln Leu Ala Gln
145                 150                 155                 160

Glu Ala Lys Phe Ala Ser Gly Ser Ser Arg Ser Phe Tyr Gly Pro
                165                 170                 175

Leu Gly Ala Trp Asp Lys Asp Ser Gly Glu Ile Tyr Pro Val Glu Thr
            180                 185                 190

Asp Leu Lys Leu Ala Met Ile Met Leu Val Leu Glu Asp Lys Lys Lys
```

```
                195                 200                 205
Pro Ile Ser Ser Arg Asp Gly Met Lys Leu Cys Val Glu Thr Ser Thr
        210                 215                 220
Thr Phe Asp Asp Trp Val Arg Gln Ser Glu Lys Asp Tyr Gln Asp Met
225                 230                 235                 240
Leu Ile Tyr Leu Lys Glu Asn Asp Phe Ala Lys Ile Gly Glu Leu Thr
                245                 250                 255
Glu Lys Asn Ala Leu Ala Met His Ala Thr Thr Lys Thr Ala Ser Pro
        260                 265                 270
Ala Phe Ser Tyr Leu Thr Asp Ala Ser Tyr Glu Ala Met Asp Phe Val
                275                 280                 285
Arg Gln Leu Arg Glu Lys Gly Glu Ala Cys Tyr Phe Thr Met Asp Ala
        290                 295                 300
Gly Pro Asn Val Lys Val Phe Cys Gln Glu Lys Asp Leu Glu His Leu
305                 310                 315                 320
Ser Glu Ile Phe Gly Gln Arg Tyr Arg Leu Ile Val Ser Lys Thr Lys
                325                 330                 335
Asp Leu Ser Gln Asp Asp Cys Cys
                340
```

<210> SEQ ID NO 53
<211> LENGTH: 297
<212> TYPE: PRT
<213> ORGANISM: Geobacillus stearothermophilus

<400> SEQUENCE: 53

```
Met Ala Gln Leu Ser Val Glu Gln Phe Leu Asn Glu Gln Lys Gln Ala
1               5                   10                  15
Val Glu Thr Ala Leu Ser Arg Tyr Ile Glu Arg Leu Glu Gly Pro Ala
                20                  25                  30
Lys Leu Lys Lys Ala Met Ala Tyr Ser Leu Glu Ala Gly Gly Lys Arg
            35                  40                  45
Ile Arg Pro Leu Leu Leu Leu Ser Thr Val Arg Ala Leu Gly Lys Asp
        50                  55                  60
Pro Ala Val Gly Leu Pro Val Ala Cys Ala Ile Glu Met Ile His Thr
65                  70                  75                  80
Tyr Ser Leu Ile His Asp Asp Leu Pro Ser Met Asp Asn Asp Asp Leu
                85                  90                  95
Arg Arg Gly Lys Pro Thr Asn His Lys Val Phe Gly Glu Ala Met Ala
            100                 105                 110
Ile Leu Ala Gly Asp Gly Leu Leu Thr Tyr Ala Phe Gln Leu Ile Thr
        115                 120                 125
Glu Ile Asp Asp Glu Arg Ile Pro Pro Ser Val Arg Leu Arg Leu Ile
    130                 135                 140
Glu Arg Leu Ala Lys Ala Ala Gly Pro Glu Gly Met Val Ala Gly Gln
145                 150                 155                 160
Ala Ala Asp Met Glu Gly Glu Gly Lys Thr Leu Thr Leu Ser Glu Leu
                165                 170                 175
Glu Tyr Ile His Arg His Lys Thr Gly Lys Met Leu Gln Tyr Ser Val
            180                 185                 190
His Ala Gly Ala Leu Ile Gly Gly Ala Asp Ala Arg Gln Thr Arg Glu
        195                 200                 205
Leu Asp Glu Phe Ala Ala His Leu Gly Leu Ala Phe Gln Ile Arg Asp
    210                 215                 220
```

```
Asp Ile Leu Asp Ile Glu Gly Ala Glu Glu Lys Ile Gly Lys Pro Val
225                 230                 235                 240

Gly Ser Asp Gln Ser Asn Asn Lys Ala Thr Tyr Pro Ala Leu Leu Ser
            245                 250                 255

Leu Ala Gly Ala Lys Glu Lys Leu Ala Phe His Ile Glu Ala Ala Gln
        260                 265                 270

Arg His Leu Arg Asn Ala Asp Val Asp Gly Ala Ala Leu Ala Tyr Ile
    275                 280                 285

Cys Glu Leu Val Ala Ala Arg Asp His
290                 295

<210> SEQ ID NO 54
<211> LENGTH: 789
<212> TYPE: DNA
<213> ORGANISM: Escherichia coli
<220> FEATURE:
<221> NAME/KEY: CDS
<222> LOCATION: (1)..(789)

<400> SEQUENCE: 54 atg caa gtc gac ctg ctg ggt tca gcg caa tct gcg cac gcg tta cac      48
Met Gln Val Asp Leu Leu Gly Ser Ala Gln Ser Ala His Ala Leu His
1               5                   10                  15 ctt ttt cac caa cat tcc cct ctt gtg cac tgc atg acc aat gat gtg     96
Leu Phe His Gln His Ser Pro Leu Val His Cys Met Thr Asn Asp Val
                20                  25                  30 gtg caa acc ttt acc gcc aat acc ttg ctg gcg ctc ggt gca tcg cca    144
Val Gln Thr Phe Thr Ala Asn Thr Leu Leu Ala Leu Gly Ala Ser Pro
            35                  40                  45 gcg atg gtt atc gaa acc gaa gag gcc agt cag ttt gcg gct atc gcc    192
Ala Met Val Ile Glu Thr Glu Glu Ala Ser Gln Phe Ala Ala Ile Ala
        50                  55                  60 agt gcc ttg ttg att aac gtt ggc aca ctg acg cag cca cgc gct cag    240
Ser Ala Leu Leu Ile Asn Val Gly Thr Leu Thr Gln Pro Arg Ala Gln
65                  70                  75                  80 gcg atg cgt gct gcc gtt gag caa gca aaa agc tct caa aca ccc tgg    288
Ala Met Arg Ala Ala Val Glu Gln Ala Lys Ser Ser Gln Thr Pro Trp
                85                  90                  95 acg ctt gat cca gta gcg gtg ggt gcg ctc gat tat cgc cgc cat ttt    336
Thr Leu Asp Pro Val Ala Val Gly Ala Leu Asp Tyr Arg Arg His Phe
                100                 105                 110 tgt cat gaa ctt tta tct ttt aaa ccg gca gcg ata cgt ggt aat gct    384
Cys His Glu Leu Leu Ser Phe Lys Pro Ala Ala Ile Arg Gly Asn Ala
            115                 120                 125 tcg gaa atc atg gca tta gct ggc att gct aat ggc gga cgg gga gtg    432
Ser Glu Ile Met Ala Leu Ala Gly Ile Ala Asn Gly Gly Arg Gly Val
        130                 135                 140 gat acc act gac gcc gca gct aac gcg ata ccc gct gca caa aca ctg    480
Asp Thr Thr Asp Ala Ala Ala Asn Ala Ile Pro Ala Ala Gln Thr Leu
145                 150                 155                 160 gca cgg gaa act ggc gca atc gtc gtg gtc act ggc gag atg gat tat    528
Ala Arg Glu Thr Gly Ala Ile Val Val Val Thr Gly Glu Met Asp Tyr
                165                 170                 175 gtt acc gat gga cat cgt atc att ggt att cac ggt ggt gat ccg tta    576
Val Thr Asp Gly His Arg Ile Ile Gly Ile His Gly Gly Asp Pro Leu
                180                 185                 190 atg acc aaa gtg gta gga act ggc tgt gca tta tcg gcg gtt gtc gct    624
Met Thr Lys Val Val Gly Thr Gly Cys Ala Leu Ser Ala Val Val Ala
            195                 200                 205 gcc tgc tgt gcg tta cca ggc gat acg ctg gaa aat gtc gca tct gcc    672
```

```
Ala Cys Cys Ala Leu Pro Gly Asp Thr Leu Glu Asn Val Ala Ser Ala
    210                 215                 220 tgt cac tgg atg aaa caa gcc gga gaa cgc gca gtc gcc aga agc gag      720
Cys His Trp Met Lys Gln Ala Gly Glu Arg Ala Val Ala Arg Ser Glu
225                 230                 235                 240 ggg cca ggc agt ttt gtt cca cat ttc ctt gat gcg ctc tgg caa ttg      768
Gly Pro Gly Ser Phe Val Pro His Phe Leu Asp Ala Leu Trp Gln Leu
                245                 250                 255 acg cag gag gtg cag gca tga                                          789
Thr Gln Glu Val Gln Ala
            260

<210> SEQ ID NO 55
<211> LENGTH: 262
<212> TYPE: PRT
<213> ORGANISM: Escherichia coli

<400> SEQUENCE: 55

Met Gln Val Asp Leu Leu Gly Ser Ala Gln Ser Ala His Ala Leu His
1               5                   10                  15

Leu Phe His Gln His Ser Pro Leu Val His Cys Met Thr Asn Asp Val
                20                  25                  30

Val Gln Thr Phe Thr Ala Asn Thr Leu Leu Ala Leu Gly Ala Ser Pro
            35                  40                  45

Ala Met Val Ile Glu Thr Glu Ala Ser Gln Phe Ala Ala Ile Ala
    50                  55                  60

Ser Ala Leu Leu Ile Asn Val Gly Thr Leu Thr Gln Pro Arg Ala Gln
65                  70                  75                  80

Ala Met Arg Ala Ala Val Glu Gln Ala Lys Ser Ser Gln Thr Pro Trp
                85                  90                  95

Thr Leu Asp Pro Val Ala Val Gly Ala Leu Asp Tyr Arg Arg His Phe
            100                 105                 110

Cys His Glu Leu Leu Ser Phe Lys Pro Ala Ala Ile Arg Gly Asn Ala
        115                 120                 125

Ser Glu Ile Met Ala Leu Ala Gly Ile Ala Asn Gly Gly Arg Gly Val
130                 135                 140

Asp Thr Thr Asp Ala Ala Ala Asn Ala Ile Pro Ala Ala Gln Thr Leu
145                 150                 155                 160

Ala Arg Glu Thr Gly Ala Ile Val Val Thr Gly Glu Met Asp Tyr
                165                 170                 175

Val Thr Asp Gly His Arg Ile Ile Gly Ile His Gly Gly Asp Pro Leu
            180                 185                 190

Met Thr Lys Val Val Gly Thr Gly Cys Ala Leu Ser Ala Val Val Ala
        195                 200                 205

Ala Cys Cys Ala Leu Pro Gly Asp Thr Leu Glu Asn Val Ala Ser Ala
    210                 215                 220

Cys His Trp Met Lys Gln Ala Gly Glu Arg Ala Val Ala Arg Ser Glu
225                 230                 235                 240

Gly Pro Gly Ser Phe Val Pro His Phe Leu Asp Ala Leu Trp Gln Leu
                245                 250                 255

Thr Gln Glu Val Gln Ala
            260

<210> SEQ ID NO 56
<211> LENGTH: 819
<212> TYPE: DNA
<213> ORGANISM: Bacillus subtilis
```

```
<220> FEATURE:
<221> NAME/KEY: CDS
<222> LOCATION: (1)..(819)

<400> SEQUENCE: 56 atg gat gca caa tca gca gca aaa tgt ctt acg gct gtc cgc cgg cat        48
Met Asp Ala Gln Ser Ala Ala Lys Cys Leu Thr Ala Val Arg Arg His
1               5                   10                  15 agc cca ctg gtg cat agc ata acc aac aat gtc gta acg aat ttc aca        96
Ser Pro Leu Val His Ser Ile Thr Asn Asn Val Val Thr Asn Phe Thr
                20                  25                  30 gca aac ggc ctg ctc gcg ctc ggc gca tcg ccc gtt atg gcg tac gca       144
Ala Asn Gly Leu Leu Ala Leu Gly Ala Ser Pro Val Met Ala Tyr Ala
            35                  40                  45 aaa gaa gag gtc gcc gat atg gcg aaa att gcg ggt gca ctc gtt tta       192
Lys Glu Glu Val Ala Asp Met Ala Lys Ile Ala Gly Ala Leu Val Leu
        50                  55                  60 aat atc gga aca ctg agc aag gag tca gtc gaa gcg atg atc atc gcg       240
Asn Ile Gly Thr Leu Ser Lys Glu Ser Val Glu Ala Met Ile Ile Ala
65                  70                  75                  80 gga aaa tca gct aat gaa cat ggc gtt ccc gtc att ctt gat cct gtc       288
Gly Lys Ser Ala Asn Glu His Gly Val Pro Val Ile Leu Asp Pro Val
                85                  90                  95 ggt gcc gga gca aca ccg ttc cgc act gaa tcg gca cgt gac atc att       336
Gly Ala Gly Ala Thr Pro Phe Arg Thr Glu Ser Ala Arg Asp Ile Ile
            100                 105                 110 cgt gag gtg cgc ctt gct gca atc aga gga aat gcg gcg gaa att gcc       384
Arg Glu Val Arg Leu Ala Ala Ile Arg Gly Asn Ala Ala Glu Ile Ala
        115                 120                 125 cat acc gtc ggc gtg acc gat tgg ctg atc aaa ggt gtt gat gcg ggt       432
His Thr Val Gly Val Thr Asp Trp Leu Ile Lys Gly Val Asp Ala Gly
    130                 135                 140 gaa ggt gga ggc gac atc atc cgg ctg gct cag cag gcg gca caa aag       480
Glu Gly Gly Gly Asp Ile Ile Arg Leu Ala Gln Gln Ala Ala Gln Lys
145                 150                 155                 160 cta aac acg gtc att gcg ata act ggt gaa gtt gat gtc ata gcc gac       528
Leu Asn Thr Val Ile Ala Ile Thr Gly Glu Val Asp Val Ile Ala Asp
                165                 170                 175 acg tca cat gta tac acc ctt cat aac ggc cac aag ctg ctg aca aaa       576
Thr Ser His Val Tyr Thr Leu His Asn Gly His Lys Leu Leu Thr Lys
            180                 185                 190 gtg aca ggc gcc ggt tgc ctg ctg act tcc gtc gtc ggt gcg ttt tgc       624
Val Thr Gly Ala Gly Cys Leu Leu Thr Ser Val Val Gly Ala Phe Cys
        195                 200                 205 gct gtg gaa gaa aat cca ttg ttt gct gct att gcg gcc att tct tcg       672
Ala Val Glu Glu Asn Pro Leu Phe Ala Ala Ile Ala Ala Ile Ser Ser
    210                 215                 220 tat ggg gtc gcc gct cag ctt gcc gca cag cag acg gct gac aaa ggc       720
Tyr Gly Val Ala Ala Gln Leu Ala Ala Gln Gln Thr Ala Asp Lys Gly
225                 230                 235                 240 cct gga agc ttt cag att gaa ttg ctg aac aag ctt tca act gtt act       768
Pro Gly Ser Phe Gln Ile Glu Leu Leu Asn Lys Leu Ser Thr Val Thr
                245                 250                 255 gaa caa gac gtc caa gaa tgg gcg act ata gaa agg gtg act gtc tca       816
Glu Gln Asp Val Gln Glu Trp Ala Thr Ile Glu Arg Val Thr Val Ser
            260                 265                 270 tga                                                                   819

<210> SEQ ID NO 57
<211> LENGTH: 272
```

<212> TYPE: PRT
<213> ORGANISM: Bacillus subtilis

<400> SEQUENCE: 57

```
Met Asp Ala Gln Ser Ala Ala Lys Cys Leu Thr Ala Val Arg Arg His
1               5                   10                  15

Ser Pro Leu Val His Ser Ile Thr Asn Asn Val Val Thr Asn Phe Thr
            20                  25                  30

Ala Asn Gly Leu Leu Ala Leu Gly Ala Ser Pro Val Met Ala Tyr Ala
        35                  40                  45

Lys Glu Glu Val Ala Asp Met Ala Lys Ile Ala Gly Ala Leu Val Leu
    50                  55                  60

Asn Ile Gly Thr Leu Ser Lys Glu Ser Val Glu Ala Met Ile Ile Ala
65                  70                  75                  80

Gly Lys Ser Ala Asn Glu His Gly Val Pro Val Ile Leu Asp Pro Val
                85                  90                  95

Gly Ala Gly Ala Thr Pro Phe Arg Thr Glu Ser Ala Arg Asp Ile Ile
            100                 105                 110

Arg Glu Val Arg Leu Ala Ala Ile Arg Gly Asn Ala Ala Glu Ile Ala
        115                 120                 125

His Thr Val Gly Val Thr Asp Trp Leu Ile Lys Gly Val Asp Ala Gly
    130                 135                 140

Glu Gly Gly Gly Asp Ile Ile Arg Leu Ala Gln Gln Ala Ala Gln Lys
145                 150                 155                 160

Leu Asn Thr Val Ile Ala Ile Thr Gly Glu Val Asp Val Ile Ala Asp
                165                 170                 175

Thr Ser His Val Tyr Thr Leu His Asn Gly His Lys Leu Leu Thr Lys
            180                 185                 190

Val Thr Gly Ala Gly Cys Leu Leu Thr Ser Val Val Gly Ala Phe Cys
        195                 200                 205

Ala Val Glu Glu Asn Pro Leu Phe Ala Ala Ile Ala Ala Ile Ser Ser
    210                 215                 220

Tyr Gly Val Ala Ala Gln Leu Ala Ala Gln Thr Ala Asp Lys Gly
225                 230                 235                 240

Pro Gly Ser Phe Gln Ile Glu Leu Leu Asn Lys Leu Ser Thr Val Thr
                245                 250                 255

Glu Gln Asp Val Gln Glu Trp Ala Thr Ile Glu Arg Val Thr Val Ser
            260                 265                 270
```

<210> SEQ ID NO 58
<211> LENGTH: 783
<212> TYPE: DNA
<213> ORGANISM: Methanocaldococcus jannaschii
<220> FEATURE:
<221> NAME/KEY: CDS
<222> LOCATION: (1)..(783)

<400> SEQUENCE: 58

```
atg ttg act att ctt aag ttg gga ggg agc att ctg tcc gat aaa aac      48
Met Leu Thr Ile Leu Lys Leu Gly Gly Ser Ile Leu Ser Asp Lys Asn
1               5                   10                  15 gtt cca tat agc att aag tgg gat aac tta gaa cgt att gct atg gaa      96
Val Pro Tyr Ser Ile Lys Trp Asp Asn Leu Glu Arg Ile Ala Met Glu
            20                  25                  30 atc aaa aac gcg tta gat tat tac aag aac caa aat aaa gaa att aag     144
Ile Lys Asn Ala Leu Asp Tyr Tyr Lys Asn Gln Asn Lys Glu Ile Lys
        35                  40                  45
```

```
ctt att ctg gta cat ggc ggc ggg gca ttt ggg cat cca gtg gcc aag    192
Leu Ile Leu Val His Gly Gly Gly Ala Phe Gly His Pro Val Ala Lys
 50              55                  60 aaa tac ctg aag att gaa gac ggc aaa aaa att ttc atc aac atg gaa    240
Lys Tyr Leu Lys Ile Glu Asp Gly Lys Lys Ile Phe Ile Asn Met Glu
 65              70                  75                  80 aaa gga ttc tgg gag att cag cgt gcg atg cgc cgt ttt aat aac atc    288
Lys Gly Phe Trp Glu Ile Gln Arg Ala Met Arg Arg Phe Asn Asn Ile
                 85                  90                  95 atc atc gac acg ctt cag agt tac gat atc cca gcg gtc tcg att caa    336
Ile Ile Asp Thr Leu Gln Ser Tyr Asp Ile Pro Ala Val Ser Ile Gln
            100                 105                 110 cct tcc agc ttt gtt gtt ttt ggc gac aaa ttg atc ttc gac acc tct    384
Pro Ser Ser Phe Val Val Phe Gly Asp Lys Leu Ile Phe Asp Thr Ser
                115                 120                 125 gcg atc aaa gag atg ttg aaa cgc aac ctt gta ccc gtt atc cat ggg    432
Ala Ile Lys Glu Met Leu Lys Arg Asn Leu Val Pro Val Ile His Gly
130                 135                 140 gat atc gtc att gac gat aaa aat ggg tac cgt att atc agc ggt gac    480
Asp Ile Val Ile Asp Asp Lys Asn Gly Tyr Arg Ile Ile Ser Gly Asp
145                 150                 155                 160 gac atc gtg cca tat tta gcc aat gaa ctg aag gca gat tta atc ctt    528
Asp Ile Val Pro Tyr Leu Ala Asn Glu Leu Lys Ala Asp Leu Ile Leu
                165                 170                 175 tat gca acc gac gtg gac ggc gta ttg att gac aac aag ccc att aaa    576
Tyr Ala Thr Asp Val Asp Gly Val Leu Ile Asp Asn Lys Pro Ile Lys
                180                 185                 190 cgc att gat aag aat aat atc tac aag att ttg aat tat ctt tcg ggt    624
Arg Ile Asp Lys Asn Asn Ile Tyr Lys Ile Leu Asn Tyr Leu Ser Gly
            195                 200                 205 agc aat tca att gac gtc acg ggg ggg atg aaa tac aag atc gac atg    672
Ser Asn Ser Ile Asp Val Thr Gly Gly Met Lys Tyr Lys Ile Asp Met
210                 215                 220 atc cgt aaa aac aaa tgc cgt ggt ttc gtg ttt aat ggc aac aag gca    720
Ile Arg Lys Asn Lys Cys Arg Gly Phe Val Phe Asn Gly Asn Lys Ala
225                 230                 235                 240 aac aac att tat aag gcg ctg ctt ggg gaa gtc gag ggt acc gaa atc    768
Asn Asn Ile Tyr Lys Ala Leu Leu Gly Glu Val Glu Gly Thr Glu Ile
                245                 250                 255 gac ttt tct gaa taa                                                783
Asp Phe Ser Glu
            260

<210> SEQ ID NO 59
<211> LENGTH: 260
<212> TYPE: PRT
<213> ORGANISM: Methanocaldococcus jannaschii

<400> SEQUENCE: 59

Met Leu Thr Ile Leu Lys Leu Gly Gly Ser Ile Leu Ser Asp Lys Asn
1               5                   10                  15

Val Pro Tyr Ser Ile Lys Trp Asp Asn Leu Glu Arg Ile Ala Met Glu
                20                  25                  30

Ile Lys Asn Ala Leu Asp Tyr Tyr Lys Asn Gln Asn Lys Glu Ile Lys
            35                  40                  45

Leu Ile Leu Val His Gly Gly Gly Ala Phe Gly His Pro Val Ala Lys
        50                  55                  60

Lys Tyr Leu Lys Ile Glu Asp Gly Lys Lys Ile Phe Ile Asn Met Glu
65              70                  75                  80
```

```
Lys Gly Phe Trp Glu Ile Gln Arg Ala Met Arg Arg Phe Asn Asn Ile
             85                  90                  95

Ile Ile Asp Thr Leu Gln Ser Tyr Asp Ile Pro Ala Val Ser Ile Gln
        100                 105                 110

Pro Ser Ser Phe Val Val Phe Gly Asp Lys Leu Ile Phe Asp Thr Ser
        115                 120                 125

Ala Ile Lys Glu Met Leu Lys Arg Asn Leu Val Pro Val Ile His Gly
    130                 135                 140

Asp Ile Val Ile Asp Lys Asn Gly Tyr Arg Ile Ile Ser Gly Asp
145                 150                 155                 160

Asp Ile Val Pro Tyr Leu Ala Asn Glu Leu Lys Ala Asp Leu Ile Leu
                165                 170                 175

Tyr Ala Thr Asp Val Asp Gly Val Leu Ile Asp Asn Lys Pro Ile Lys
            180                 185                 190

Arg Ile Asp Lys Asn Asn Ile Tyr Lys Ile Leu Asn Tyr Leu Ser Gly
        195                 200                 205

Ser Asn Ser Ile Asp Val Thr Gly Gly Met Lys Tyr Lys Ile Asp Met
    210                 215                 220

Ile Arg Lys Asn Lys Cys Arg Gly Phe Val Phe Asn Gly Asn Lys Ala
225                 230                 235                 240

Asn Asn Ile Tyr Lys Ala Leu Leu Gly Glu Val Glu Gly Thr Glu Ile
                245                 250                 255

Asp Phe Ser Glu
            260

<210> SEQ ID NO 60
<211> LENGTH: 744
<212> TYPE: DNA
<213> ORGANISM: Methanothrix themoacetophila
<220> FEATURE:
<221> NAME/KEY: CDS
<222> LOCATION: (1)..(744)

<400> SEQUENCE: 60 tta aag att ttg aaa ttg ggc ggt agc att att acg gat aag agc cgc      48
Leu Lys Ile Leu Lys Leu Gly Gly Ser Ile Ile Thr Asp Lys Ser Arg
1               5                   10                  15 tta gct act gca cgt ctg gat caa att tca cgt atc gca cac gaa atc      96
Leu Ala Thr Ala Arg Leu Asp Gln Ile Ser Arg Ile Ala His Glu Ile
            20                  25                  30 tca ggc atc gag aac ctg att gtt gtt cac gga gcc ggt tct ttt ggt     144
Ser Gly Ile Glu Asn Leu Ile Val Val His Gly Ala Gly Ser Phe Gly
        35                  40                  45 cac atc cat gcc aaa aat ttc ggt ctt ccg gaa cgt ttc tca gga gaa     192
His Ile His Ala Lys Asn Phe Gly Leu Pro Glu Arg Phe Ser Gly Glu
    50                  55                  60 ggg tta ctg aaa aca cat ctg tcg gtc tcg gat ttg aat cgt atc gtc     240
Gly Leu Leu Lys Thr His Leu Ser Val Ser Asp Leu Asn Arg Ile Val
65                  70                  75                  80 gtt gaa gct ctt cat gat gca ggg gtg gac gcg ctg ccc ttg cac ccc     288
Val Glu Ala Leu His Asp Ala Gly Val Asp Ala Leu Pro Leu His Pro
                85                  90                  95 tta tca agt gta gtc ctt cgt gac gga cgc atc cac cat atg tct acc     336
Leu Ser Ser Val Val Leu Arg Asp Gly Arg Ile His His Met Ser Thr
            100                 105                 110 gag gtc att acg gaa atg ctt cgt cgt gat gta gtg ccg gta tta cat     384
Glu Val Ile Thr Glu Met Leu Arg Arg Asp Val Val Pro Val Leu His
        115                 120                 125
```

```
ggg gat gtt gcg atg gac ctg tca aag ggt gcc ggc att gta agt gga      432
Gly Asp Val Ala Met Asp Leu Ser Lys Gly Ala Gly Ile Val Ser Gly
130                 135                 140 gac cag ttg gtt tcg tat atg gca cgt act ctg gga gct ggt atg gtc      480
Asp Gln Leu Val Ser Tyr Met Ala Arg Thr Leu Gly Ala Gly Met Val
145                 150                 155                 160 gct atg ggg acc gat gtc gac ggg gtt atg atc gat ggt cgt gtc ctt      528
Ala Met Gly Thr Asp Val Asp Gly Val Met Ile Asp Gly Arg Val Leu
                165                 170                 175 agt tgc att aca cct aat gac atg cac tct ttg gag agt cac tta tta      576
Ser Cys Ile Thr Pro Asn Asp Met His Ser Leu Glu Ser His Leu Leu
                180                 185                 190 ccc gca aaa ggg gta gac gtc acg ggt gga atg cgc ggt aaa ctg gcg      624
Pro Ala Lys Gly Val Asp Val Thr Gly Gly Met Arg Gly Lys Leu Ala
                195                 200                 205 gaa tta gta gag ctg gca ggc att gga att gat tcg cgt att ttt aat      672
Glu Leu Val Glu Leu Ala Gly Ile Gly Ile Asp Ser Arg Ile Phe Asn
210                 215                 220 gcc ggt gtt gct ggt aat gta cgc cgt gct ttg tct ggg gag tcg tta      720
Ala Gly Val Ala Gly Asn Val Arg Arg Ala Leu Ser Gly Glu Ser Leu
225                 230                 235                 240 gga act ttg att act gga cgc taa                                      744
Gly Thr Leu Ile Thr Gly Arg
                245

<210> SEQ ID NO 61
<211> LENGTH: 247
<212> TYPE: PRT
<213> ORGANISM: Methanothrix themoacetophila

<400> SEQUENCE: 61

Leu Lys Ile Leu Lys Leu Gly Gly Ser Ile Ile Thr Asp Lys Ser Arg
1               5                   10                  15

Leu Ala Thr Ala Arg Leu Asp Gln Ile Ser Arg Ile Ala His Glu Ile
                20                  25                  30

Ser Gly Ile Glu Asn Leu Ile Val Val His Gly Ala Gly Ser Phe Gly
            35                  40                  45

His Ile His Ala Lys Asn Phe Gly Leu Pro Glu Arg Phe Ser Gly Glu
        50                  55                  60

Gly Leu Leu Lys Thr His Leu Ser Val Ser Asp Leu Asn Arg Ile Val
65                  70                  75                  80

Val Glu Ala Leu His Asp Ala Gly Val Asp Ala Leu Pro Leu His Pro
                85                  90                  95

Leu Ser Ser Val Val Leu Arg Asp Gly Arg Ile His His Met Ser Thr
                100                 105                 110

Glu Val Ile Thr Glu Met Leu Arg Arg Asp Val Val Pro Val Leu His
            115                 120                 125

Gly Asp Val Ala Met Asp Leu Ser Lys Gly Ala Gly Ile Val Ser Gly
        130                 135                 140

Asp Gln Leu Val Ser Tyr Met Ala Arg Thr Leu Gly Ala Gly Met Val
145                 150                 155                 160

Ala Met Gly Thr Asp Val Asp Gly Val Met Ile Asp Gly Arg Val Leu
                165                 170                 175

Ser Cys Ile Thr Pro Asn Asp Met His Ser Leu Glu Ser His Leu Leu
                180                 185                 190

Pro Ala Lys Gly Val Asp Val Thr Gly Gly Met Arg Gly Lys Leu Ala
            195                 200                 205
```

```
Glu Leu Val Glu Leu Ala Gly Ile Gly Ile Asp Ser Arg Ile Phe Asn
    210             215                 220

Ala Gly Val Ala Gly Asn Val Arg Arg Ala Leu Ser Gly Glu Ser Leu
225             230                 235                 240

Gly Thr Leu Ile Thr Gly Arg
                245

<210> SEQ ID NO 62
<211> LENGTH: 543
<212> TYPE: DNA
<213> ORGANISM: Escherichia coli
<220> FEATURE:
<221> NAME/KEY: CDS
<222> LOCATION: (1)..(543)

<400> SEQUENCE: 62 atg caa acc gag cat gtc att tta ttg gac gag caa gga gaa cca att      48
Met Gln Thr Glu His Val Ile Leu Leu Asp Glu Gln Gly Glu Pro Ile
1               5                   10                  15 gga act tta gaa aaa tac gct gca cat aca gcg gac acc cgc tta cat      96
Gly Thr Leu Glu Lys Tyr Ala Ala His Thr Ala Asp Thr Arg Leu His
                20                  25                  30 ctt gct ttt tct agt tgg ctg ttt aac gat aag ggt caa tta tta gtg     144
Leu Ala Phe Ser Ser Trp Leu Phe Asn Asp Lys Gly Gln Leu Leu Val
            35                  40                  45 acg cgc cgt gcg ctg agc aaa aaa gca tgg ccg ggt gtt tgg acg aac     192
Thr Arg Arg Ala Leu Ser Lys Lys Ala Trp Pro Gly Val Trp Thr Asn
        50                  55                  60 agt gtt tgc gga cac ccc caa ctg gga gaa tcc aat gag gat gcg gta     240
Ser Val Cys Gly His Pro Gln Leu Gly Glu Ser Asn Glu Asp Ala Val
65                  70                  75                  80 att cgc cgt tgt cgc tat gaa ttg ggt gtg gag att acg cca ccg aca     288
Ile Arg Arg Cys Arg Tyr Glu Leu Gly Val Glu Ile Thr Pro Pro Thr
                85                  90                  95 ccg atc tac cct gat ttc cgt tat cgc gct acg gat cct tca ggt att     336
Pro Ile Tyr Pro Asp Phe Arg Tyr Arg Ala Thr Asp Pro Ser Gly Ile
            100                 105                 110 gtt gaa aat gaa gta tgc cca gtg ttt gcc gcg cgc aca act tct gcg     384
Val Glu Asn Glu Val Cys Pro Val Phe Ala Ala Arg Thr Thr Ser Ala
        115                 120                 125 ctt caa atc aac cca gac gag gtc atg gat tac caa tgg tgt gat ctt     432
Leu Gln Ile Asn Pro Asp Glu Val Met Asp Tyr Gln Trp Cys Asp Leu
    130                 135                 140 gct gac gta ctg cac ggg att gac gcg aca ccg tgg gct ttt agt ccc     480
Ala Asp Val Leu His Gly Ile Asp Ala Thr Pro Trp Ala Phe Ser Pro
145                 150                 155                 160 tgg atg gtt atg caa gcg aca aat gaa gaa gca cgt aag cgc ctt cag     528
Trp Met Val Met Gln Ala Thr Asn Glu Glu Ala Arg Lys Arg Leu Gln
                165                 170                 175 gcg ttt act cag taa                                                  543
Ala Phe Thr Gln
            180

<210> SEQ ID NO 63
<211> LENGTH: 180
<212> TYPE: PRT
<213> ORGANISM: Escherichia coli

<400> SEQUENCE: 63

Met Gln Thr Glu His Val Ile Leu Leu Asp Glu Gln Gly Glu Pro Ile
1               5                   10                  15
```

```
Gly Thr Leu Glu Lys Tyr Ala Ala His Thr Ala Asp Thr Arg Leu His
            20                  25                  30

Leu Ala Phe Ser Ser Trp Leu Phe Asn Asp Lys Gly Gln Leu Leu Val
        35                  40                  45

Thr Arg Arg Ala Leu Ser Lys Lys Ala Trp Pro Gly Val Trp Thr Asn
    50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Thr
                85                  90                  95

Pro Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Pro Asp Glu Val Met Asp Tyr Gln Trp Cys Asp Leu
    130                 135                 140

Ala Asp Val Leu His Gly Ile Asp Ala Thr Pro Trp Ala Phe Ser Pro
145                 150                 155                 160

Trp Met Val Met Gln Ala Thr Asn Glu Glu Ala Arg Lys Arg Leu Gln
                165                 170                 175

Ala Phe Thr Gln
            180

<210> SEQ ID NO 64
<211> LENGTH: 894
<212> TYPE: DNA
<213> ORGANISM: Geobacillus stearothermophilus
<220> FEATURE:
<221> NAME/KEY: CDS
<222> LOCATION: (1)..(894)

<400> SEQUENCE: 64 atg gcg cag ctt tca gtt gaa cag ttt ctc aac gag caa aaa cag gcg      48
Met Ala Gln Leu Ser Val Glu Gln Phe Leu Asn Glu Gln Lys Gln Ala
1               5                   10                  15 gtg gaa aca gcg ctc tcc cgt tat ata gag cgc tta gaa ggg ccg gcg      96
Val Glu Thr Ala Leu Ser Arg Tyr Ile Glu Arg Leu Glu Gly Pro Ala
            20                  25                  30 aag ctg aaa aag gcg atg gcg tac tca ttg gag gcc ggc ggc aaa cga     144
Lys Leu Lys Lys Ala Met Ala Tyr Ser Leu Glu Ala Gly Gly Lys Arg
        35                  40                  45 atc cgt ccg ttg ctg ctt ctg tcc acc gtt cgg gcg ctc ggc aaa gac     192
Ile Arg Pro Leu Leu Leu Leu Ser Thr Val Arg Ala Leu Gly Lys Asp
    50                  55                  60 ccg gcg gtc gga ttg ccc gtc gcc tgc gcg att gaa atg atc cat acg     240
Pro Ala Val Gly Leu Pro Val Ala Cys Ala Ile Glu Met Ile His Thr
65                  70                  75                  80 tac ttt ttg atc cat gat gat ttg ccg agc atg gac aac gat gat ttg     288
Tyr Phe Leu Ile His Asp Asp Leu Pro Ser Met Asp Asn Asp Asp Leu
                85                  90                  95 cgg cgc ggc aag ccg acg aac cat aaa gtg ttc ggc gag gcg atg gcc     336
Arg Arg Gly Lys Pro Thr Asn His Lys Val Phe Gly Glu Ala Met Ala
            100                 105                 110 atc ttg gcg ggg gac ggg ttg ttg acg tac gcg ttt caa ttg atc acc     384
Ile Leu Ala Gly Asp Gly Leu Leu Thr Tyr Ala Phe Gln Leu Ile Thr
        115                 120                 125 gaa atc gac gat gag cgc atc cct cct tcc gtc cgg ctt cgg ctc atc     432
Glu Ile Asp Asp Glu Arg Ile Pro Pro Ser Val Arg Leu Arg Leu Ile
    130                 135                 140
```

```
gaa cgg ctg gcg aaa gcg gcc ggt ccg gaa ggg atg gtc gcc ggt cag    480
Glu Arg Leu Ala Lys Ala Ala Gly Pro Glu Gly Met Val Ala Gly Gln
145                 150                 155                 160 gca gcc gat atg gaa gga gag ggg aaa acg ctg acg ctt tcg gag ctc    528
Ala Ala Asp Met Glu Gly Glu Gly Lys Thr Leu Thr Leu Ser Glu Leu
                165                 170                 175 gaa tac att cat cgg cat aaa acc ggg aaa atg ctg caa tac agc gtg    576
Glu Tyr Ile His Arg His Lys Thr Gly Lys Met Leu Gln Tyr Ser Val
            180                 185                 190 cac gcc ggc gcc ttg atc ggc ggc gct gat gcc cgg caa acg cgg gag    624
His Ala Gly Ala Leu Ile Gly Gly Ala Asp Ala Arg Gln Thr Arg Glu
        195                 200                 205 ctt gac gaa ttc gcc gcc cat cta ggc ctt gcc ttt caa att cgc gat    672
Leu Asp Glu Phe Ala Ala His Leu Gly Leu Ala Phe Gln Ile Arg Asp
    210                 215                 220 gat att ctc gat att gaa ggg gca gaa gaa aaa atc ggc aag ccg gtc    720
Asp Ile Leu Asp Ile Glu Gly Ala Glu Glu Lys Ile Gly Lys Pro Val
225                 230                 235                 240 ggc agc gac caa agc aac aac aaa gcg acg tat cca gcg ttg ctg tcg    768
Gly Ser Asp Gln Ser Asn Asn Lys Ala Thr Tyr Pro Ala Leu Leu Ser
                245                 250                 255 ctt gcc ggc gcg aag gaa aag ttg gcg ttc cat atc gag gcg gcg cag    816
Leu Ala Gly Ala Lys Glu Lys Leu Ala Phe His Ile Glu Ala Ala Gln
            260                 265                 270 cgc cat tta cgg aac gct gac gtt gac ggc gcc gcg ctc gcc tat att    864
Arg His Leu Arg Asn Ala Asp Val Asp Gly Ala Ala Leu Ala Tyr Ile
        275                 280                 285 tgc gaa ctg gtc gcc gcc cgc gac cat taa                            894
Cys Glu Leu Val Ala Ala Arg Asp His
    290                 295
```

<210> SEQ ID NO 65
<211> LENGTH: 297
<212> TYPE: PRT
<213> ORGANISM: Geobacillus stearothermophilus

<400> SEQUENCE: 65

```
Met Ala Gln Leu Ser Val Glu Gln Phe Leu Asn Glu Gln Lys Gln Ala
1               5                   10                  15

Val Glu Thr Ala Leu Ser Arg Tyr Ile Glu Arg Leu Glu Gly Pro Ala
                20                  25                  30

Lys Leu Lys Lys Ala Met Ala Tyr Ser Leu Glu Ala Gly Gly Lys Arg
            35                  40                  45

Ile Arg Pro Leu Leu Leu Leu Ser Thr Val Arg Ala Leu Gly Lys Asp
        50                  55                  60

Pro Ala Val Gly Leu Pro Val Ala Cys Ala Ile Glu Met Ile His Thr
65                  70                  75                  80

Tyr Phe Leu Ile His Asp Asp Leu Pro Ser Met Asp Asn Asp Asp Leu
                85                  90                  95

Arg Arg Gly Lys Pro Thr Asn His Lys Val Phe Gly Glu Ala Met Ala
            100                 105                 110

Ile Leu Ala Gly Asp Gly Leu Leu Thr Tyr Ala Phe Gln Leu Ile Thr
        115                 120                 125

Glu Ile Asp Asp Glu Arg Ile Pro Pro Ser Val Arg Leu Arg Leu Ile
    130                 135                 140

Glu Arg Leu Ala Lys Ala Ala Gly Pro Glu Gly Met Val Ala Gly Gln
145                 150                 155                 160
```

Ala Ala Asp Met Glu Gly Glu Gly Lys Thr Leu Thr Leu Ser Glu Leu
                165                 170                 175

Glu Tyr Ile His Arg His Lys Thr Gly Lys Met Leu Gln Tyr Ser Val
            180                 185                 190

His Ala Gly Ala Leu Ile Gly Gly Ala Asp Ala Arg Gln Thr Arg Glu
        195                 200                 205

Leu Asp Glu Phe Ala Ala His Leu Gly Leu Ala Phe Gln Ile Arg Asp
    210                 215                 220

Asp Ile Leu Asp Ile Glu Gly Ala Glu Glu Lys Ile Gly Lys Pro Val
225                 230                 235                 240

Gly Ser Asp Gln Ser Asn Asn Lys Ala Thr Tyr Pro Ala Leu Leu Ser
                245                 250                 255

Leu Ala Gly Ala Lys Glu Lys Leu Ala Phe His Ile Glu Ala Ala Gln
            260                 265                 270

Arg His Leu Arg Asn Ala Asp Val Asp Gly Ala Ala Leu Ala Tyr Ile
        275                 280                 285

Cys Glu Leu Val Ala Ala Arg Asp His
    290                 295

<210> SEQ ID NO 66
<211> LENGTH: 924
<212> TYPE: DNA
<213> ORGANISM: Artificial Sequence
<220> FEATURE:
<223> OTHER INFORMATION: NphB M23 cDNA

<400> SEQUENCE: 66
atgtccgagg cggccgacgt ggagcgtgtt tatgctgcta tggaagaagc tgcgggtctg      60
ctgggagtgg catgtgctcg tgataagatt tatccccttc tttcaacctt ccaggataca     120
ttggttgaag gtggcagtgt ggtagtgttt agcatggcta gtggacgcca cagcacggaa     180
ctggacttta gtatttcagt acccacgtcc catggtgacc catacgcaac tgtcgtcgaa     240
aaggggctgt ccctgcaac aggccatcct gttgacgatc ttttggctga tacgcagaag     300
cacctgcctg tttctatgtt cgccattgat ggagaagtca ccggaggttt caaaaaaact     360
tatgctttct ttccaactga taatatgcca ggtgtgccg agttgagtgc catccccagt     420
atgccaccgg cggtcgcgga aaacgccgaa ttattcgcgc gttatgggtt agataaggtg     480
cagatgacgt caatggacta caagaagcgc caggtcaatt tgtacttctc tgagttaagt     540
gcacagactt tagaagccga gtctgtcctt gcgcttgttc gtgaactggg tttgcacgtg     600
ccgaacgaac tgggtcttaa attttgcaag cgctcctttt ccgtttatcc gacactgaac     660
tgggaaacag ggaaaattga tcgtttatgt tttgcggtga tttcaaacga ccctaccttg     720
gtaccaagtt cggacgaagg ggacattgaa aaatttcaca actacgcgac gaaggcgccg     780
tacgcatacg tcggcgaaaa gcgtacgctg gtttacgggt tgacgctgag tcccaaagag     840
gaatactata aattaagcgc agcgtaccat atcaccgatg tacaacgcgg actgctgaag     900
gcctttgata gccttgaaga ctaa                                            924

<210> SEQ ID NO 67
<211> LENGTH: 924
<212> TYPE: DNA
<213> ORGANISM: Artificial Sequence
<220> FEATURE:
<223> OTHER INFORMATION: NphB M31 cDNA

<400> SEQUENCE: 67

```
atgtccgagg cggccgacgt ggagcgtgtt tatgctgcta tggaagaagc tgcgggtctg    60 ctggagtgg catgtgctcg tgataagatt tatcccttc tttcaacctt ccaggataca    120
ttggttgaag gtggcagtgt ggtagtgttt agcatggcta gtggacgcca cagcacggaa    180
ctggacttta gtatttcagt acccacgtcc catggtgacc catacgcaac tgtcgtcgaa    240
aaggggctgt tccctgcaac aggccatcct gttgacgatc ttttggctga tacgcagaag    300
cacctgcctg tttctatgtt cgccattgat ggagaagtca ccggaggttt caaaaaaact    360
tatgctttct ttccaactga taatatgcca ggtgtggccg agttgagtgc catccccagt    420
atgccaccgg cggtcgcgga aaacgccgaa ttattcgcgc gttatgggtt agataaggtg    480
cagatgacgt caatggacta agaagcgc caggtcaatt tgtacttctc tgagttaagt    540
gcacagactt tagaagccga gtctgtcctt gcgcttgttc gtgaactggg tttgcacgtg    600
ccgaacgaac tgggtcttaa attttgcaag cgctcctttt ccgtttatcc gacactgaac    660
tgggaaacag gaaaattga tcgtttatgt tttagcgtga tttcaaacga ccctaccttg    720
gtaccaagtt cggacgaagg ggacattgaa aaatttcaca actacgcgac gaaggcgccg    780
tacgcatacg tcggcgaaaa gcgtacgctg gtttacgggt tgacgctgag tcccaaagag    840
gaatactata aattaggcgc agtgtaccat atcaccgatg tacaacgcgg actgctgaag    900
gcctttgata gccttgaaga ctaa                                           924
```

<210> SEQ ID NO 68
<211> LENGTH: 924
<212> TYPE: DNA
<213> ORGANISM: Artificial Sequence
<220> FEATURE:
<223> OTHER INFORMATION: NpHB M31 Pross 10 cDNA
<220> FEATURE:
<221> NAME/KEY: CDS
<222> LOCATION: (1)..(924)

<400> SEQUENCE: 68

```
atg tcg gaa gct gcc gat gta gaa cgt gtc tac gcc gcc atc gaa gaa      48
Met Ser Glu Ala Ala Asp Val Glu Arg Val Tyr Ala Ala Ile Glu Glu
1               5                  10                  15 gcc gca ggt ttg ttg ggg gtc gca tgc gca cgc gat aag att tgg ccc      96
Ala Ala Gly Leu Leu Gly Val Ala Cys Ala Arg Asp Lys Ile Trp Pro
            20                  25                  30 ttg ctg tca aca ttc cag gat acc ttg gtt gag ggt gga agc gta gtt     144
Leu Leu Ser Thr Phe Gln Asp Thr Leu Val Glu Gly Gly Ser Val Val
        35                  40                  45 gtt ttt agc atg gcc tcg ggg cgt cac tca acg gag ctg gac ttc tca     192
Val Phe Ser Met Ala Ser Gly Arg His Ser Thr Glu Leu Asp Phe Ser
    50                  55                  60 att tcc gtc ccg cct agt cat ggc gat ccg tac gcg att gtg gtg gaa     240
Ile Ser Val Pro Pro Ser His Gly Asp Pro Tyr Ala Ile Val Val Glu
65                  70                  75                  80 aag ggc ttg ttc ccg gca act gga cat cca gtt gat gac ctt ctg gcg     288
Lys Gly Leu Phe Pro Ala Thr Gly His Pro Val Asp Asp Leu Leu Ala
                85                  90                  95 gac att cag aag cat ctt ccc gta tct atg ttt gcg att gac ggg gaa     336
Asp Ile Gln Lys His Leu Pro Val Ser Met Phe Ala Ile Asp Gly Glu
            100                 105                 110 gtt acc ggg ggg ttc aaa aaa act tat gcg ttc ttc ccg acc gat aac     384
Val Thr Gly Gly Phe Lys Lys Thr Tyr Ala Phe Phe Pro Thr Asp Asn
        115                 120                 125 atg ccc ggt gtc gcg gaa ctg gcg gcc atc cca tcg atg cct cct gca     432
Met Pro Gly Val Ala Glu Leu Ala Ala Ile Pro Ser Met Pro Pro Ala
```

```
gtc gct gaa aat gct gaa ctg ttc gcg cgt tat ggc ctg gac aag gta    480
Val Ala Glu Asn Ala Glu Leu Phe Ala Arg Tyr Gly Leu Asp Lys Val
145                 150                 155                 160 caa atg acc tcg atg gat tat aaa aaa cgt caa gtg aac ctg tat ttc    528
Gln Met Thr Ser Met Asp Tyr Lys Lys Arg Gln Val Asn Leu Tyr Phe
                165                 170                 175 tcc gaa ctg tcg gct cag acg ctg gag gct gaa tca gta ctt gct tta    576
Ser Glu Leu Ser Ala Gln Thr Leu Glu Ala Glu Ser Val Leu Ala Leu
            180                 185                 190 gtg cgt gaa ctg ggt ctt cat gtc cca aac gag ctg ggt ctg aaa ttt    624
Val Arg Glu Leu Gly Leu His Val Pro Asn Glu Leu Gly Leu Lys Phe
        195                 200                 205 tgc aaa cgc tcc ttc tca gta tac cca aca tta aac tgg gac acc tcg    672
Cys Lys Arg Ser Phe Ser Val Tyr Pro Thr Leu Asn Trp Asp Thr Ser
    210                 215                 220 aag att gac cgc ctt tgc ttc tct gta atc agt aca gat ccg aca ctt    720
Lys Ile Asp Arg Leu Cys Phe Ser Val Ile Ser Thr Asp Pro Thr Leu
225                 230                 235                 240 gta cct agc tca gac gag gga gac att gaa aaa ttt cac aat tac gct    768
Val Pro Ser Ser Asp Glu Gly Asp Ile Glu Lys Phe His Asn Tyr Ala
                245                 250                 255 aca aag gcc ccc tat gca tat gtt gga gaa aag cgt aca ctt gtt tac    816
Thr Lys Ala Pro Tyr Ala Tyr Val Gly Glu Lys Arg Thr Leu Val Tyr
            260                 265                 270 ggc ttg act tta tct ccc aaa gag gag tat tat aaa ttg ggt gcc gtt    864
Gly Leu Thr Leu Ser Pro Lys Glu Glu Tyr Tyr Lys Leu Gly Ala Val
        275                 280                 285 tac cac att act gac gta caa cgc aaa ctt ttg aag gcg ttc gac agc    912
Tyr His Ile Thr Asp Val Gln Arg Lys Leu Leu Lys Ala Phe Asp Ser
290                 295                 300 ctt gag gat taa                                                    924
Leu Glu Asp
305

<210> SEQ ID NO 69
<211> LENGTH: 307
<212> TYPE: PRT
<213> ORGANISM: Artificial Sequence
<220> FEATURE:
<223> OTHER INFORMATION: Synthetic Construct

<400> SEQUENCE: 69

Met Ser Glu Ala Ala Asp Val Glu Arg Val Tyr Ala Ala Ile Glu Glu
1               5                   10                  15

Ala Ala Gly Leu Leu Gly Val Ala Cys Ala Arg Asp Lys Ile Trp Pro
            20                  25                  30

Leu Leu Ser Thr Phe Gln Asp Thr Leu Val Glu Gly Gly Ser Val Val
        35                  40                  45

Val Phe Ser Met Ala Ser Gly Arg His Ser Thr Glu Leu Asp Phe Ser
    50                  55                  60

Ile Ser Val Pro Pro Ser His Gly Asp Pro Tyr Ala Ile Val Val Glu
65                  70                  75                  80

Lys Gly Leu Phe Pro Ala Thr Gly His Pro Val Asp Asp Leu Leu Ala
                85                  90                  95

Asp Ile Gln Lys His Leu Pro Val Ser Met Phe Ala Ile Asp Gly Glu
            100                 105                 110

Val Thr Gly Gly Phe Lys Lys Thr Tyr Ala Phe Phe Pro Thr Asp Asn
        115                 120                 125
```

```
Met Pro Gly Val Ala Glu Leu Ala Ala Ile Pro Ser Met Pro Pro Ala
        130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190

Val Arg Glu Leu Gly Leu His Val Pro Asn Glu Leu Gly Leu Lys Phe
        195                 200                 205

Cys Lys Arg Ser Phe Ser Val Tyr Pro Thr Leu Asn Trp Asp Thr Ser
    210                 215                 220

Lys Ile Asp Arg Leu Cys Phe Ser Val Ile Ser Thr Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Val
        275                 280                 285

Tyr His Ile Thr Asp Val Gln Arg Lys Leu Leu Lys Ala Phe Asp Ser
    290                 295                 300

Leu Glu Asp
305

<210> SEQ ID NO 70
<211> LENGTH: 1632
<212> TYPE: DNA
<213> ORGANISM: Cannabis sativa
<220> FEATURE:
<221> NAME/KEY: CDS
<222> LOCATION: (1)..(1632)

<400> SEQUENCE: 70 atg gaa aag agt ggc tac gga cgc gac ggt att tac cgt agc ctg cgt      48
Met Glu Lys Ser Gly Tyr Gly Arg Asp Gly Ile Tyr Arg Ser Leu Arg
1               5                   10                  15 cct cct tta cac ctg cca aac aat aac aat ttg agt atg gtc tca ttc      96
Pro Pro Leu His Leu Pro Asn Asn Asn Asn Leu Ser Met Val Ser Phe
            20                  25                  30 ctg ttc cgt aac agc agc agc tat cca cag aaa ccg gcg ttg atc gat     144
Leu Phe Arg Asn Ser Ser Ser Tyr Pro Gln Lys Pro Ala Leu Ile Asp
        35                  40                  45 agc gag act aat caa att tta tct ttt agt cat ttt aaa agc acc gtg     192
Ser Glu Thr Asn Gln Ile Leu Ser Phe Ser His Phe Lys Ser Thr Val
    50                  55                  60 atc aag gtc tcc cat ggc ttc tta aac ctg ggg atc aaa aag aat gac     240
Ile Lys Val Ser His Gly Phe Leu Asn Leu Gly Ile Lys Lys Asn Asp
65                  70                  75                  80 gtg gtt tta atc tac gca ccc aat tcg atc cac ttt ccc gta tgc ttc     288
Val Val Leu Ile Tyr Ala Pro Asn Ser Ile His Phe Pro Val Cys Phe
                85                  90                  95 ctt ggc att att gct tct ggg gcg atc gcc act act tca aat cca tta     336
Leu Gly Ile Ile Ala Ser Gly Ala Ile Ala Thr Thr Ser Asn Pro Leu
            100                 105                 110 tac acc gtg agt gag ttg tcg aaa caa gta aag gac tcg aac cct aaa     384
Tyr Thr Val Ser Glu Leu Ser Lys Gln Val Lys Asp Ser Asn Pro Lys
        115                 120                 125
```

```
ttg att atc aca gtc cct cag tta ttg gaa aag gtc aag ggt ttc aat      432
Leu Ile Ile Thr Val Pro Gln Leu Leu Glu Lys Val Lys Gly Phe Asn
    130                 135                 140 ctg cca act atc ctt atc ggc cct gat tct gag cag gaa tcg tct agt      480
Leu Pro Thr Ile Leu Ile Gly Pro Asp Ser Glu Gln Glu Ser Ser Ser
145                 150                 155                 160 gat aaa gta atg act ttc aat gat ctg gtc aat ctg gga gga agt tcg      528
Asp Lys Val Met Thr Phe Asn Asp Leu Val Asn Leu Gly Gly Ser Ser
                165                 170                 175 ggt agc gaa ttc cct atc gtc gac gat ttc aag caa tcc gac acc gcc      576
Gly Ser Glu Phe Pro Ile Val Asp Asp Phe Lys Gln Ser Asp Thr Ala
            180                 185                 190 gca ctg ttg tac tca agt ggc acg aca ggt atg agc aag ggg gtc gtt      624
Ala Leu Leu Tyr Ser Ser Gly Thr Thr Gly Met Ser Lys Gly Val Val
        195                 200                 205 ctg acg cac aaa aat ttt att gcc tca tcg ttg atg gta aca atg gaa      672
Leu Thr His Lys Asn Phe Ile Ala Ser Ser Leu Met Val Thr Met Glu
    210                 215                 220 cag gac ttg gtc ggc gag atg gac aat gtg ttc ctg tgt ttc ctt cct      720
Gln Asp Leu Val Gly Glu Met Asp Asn Val Phe Leu Cys Phe Leu Pro
225                 230                 235                 240 atg ttt cac gtc ttt ggc tta gcc att att acg tat gct cag tta cag      768
Met Phe His Val Phe Gly Leu Ala Ile Ile Thr Tyr Ala Gln Leu Gln
                245                 250                 255 cgc ggt aat acc gtg att tca atg gcc cgc ttt gac ttg gaa aag atg      816
Arg Gly Asn Thr Val Ile Ser Met Ala Arg Phe Asp Leu Glu Lys Met
            260                 265                 270 tta aaa gat gtt gaa aag tac aaa gtt acc cac ctt tgg gtc gta ccc      864
Leu Lys Asp Val Glu Lys Tyr Lys Val Thr His Leu Trp Val Val Pro
        275                 280                 285 cca gtt atc tta gcg ttg tcg aag aac tca atg gtg aaa aaa ttc aat      912
Pro Val Ile Leu Ala Leu Ser Lys Asn Ser Met Val Lys Lys Phe Asn
    290                 295                 300 ttg tca tcc atc aag tat att ggt tca ggc gct gcg cca tta gga aag      960
Leu Ser Ser Ile Lys Tyr Ile Gly Ser Gly Ala Ala Pro Leu Gly Lys
305                 310                 315                 320 gat ctg atg gaa gaa tgc tct aag gtg gtt cct tac gga atc gtg gct     1008
Asp Leu Met Glu Glu Cys Ser Lys Val Val Pro Tyr Gly Ile Val Ala
                325                 330                 335 caa gga tat ggc atg acg gaa acg tgc gga atc gta tcc atg gaa gac     1056
Gln Gly Tyr Gly Met Thr Glu Thr Cys Gly Ile Val Ser Met Glu Asp
            340                 345                 350 atc cgc ggc ggg aaa cgc aat tca ggg tcg gcc gga atg ttg gca agt     1104
Ile Arg Gly Gly Lys Arg Asn Ser Gly Ser Ala Gly Met Leu Ala Ser
        355                 360                 365 ggg gta gaa gct cag atc gtg agt gtg gac acc tta aaa ccc ctt ccc     1152
Gly Val Glu Ala Gln Ile Val Ser Val Asp Thr Leu Lys Pro Leu Pro
    370                 375                 380 ccg aat caa tta ggg gaa atc tgg gta aaa ggt cca aat atg atg caa     1200
Pro Asn Gln Leu Gly Glu Ile Trp Val Lys Gly Pro Asn Met Met Gln
385                 390                 395                 400 ggc tat ttc aac aat cct caa gcg acc aaa ctt acc att gat aaa aag     1248
Gly Tyr Phe Asn Asn Pro Gln Ala Thr Lys Leu Thr Ile Asp Lys Lys
                405                 410                 415 ggt tgg gtt cat act ggc gac ttg ggg tat ttc gac gaa gac gga cac     1296
Gly Trp Val His Thr Gly Asp Leu Gly Tyr Phe Asp Glu Asp Gly His
            420                 425                 430 tta tat gtt gta gac cgt att aag gag ctt att aaa tac aag gga ttc     1344
Leu Tyr Val Val Asp Arg Ile Lys Glu Leu Ile Lys Tyr Lys Gly Phe
```

```
                    435                 440                 445
caa gtt gcg cct gcg gaa ctg gag gga tta tta gtt agt cac ccc gag      1392
Gln Val Ala Pro Ala Glu Leu Glu Gly Leu Leu Val Ser His Pro Glu
450                 455                 460 atc tta gac gcg gta gtt att ccc ttc ccc gat gct gag gca ggc gaa      1440
Ile Leu Asp Ala Val Val Ile Pro Phe Pro Asp Ala Glu Ala Gly Glu
465                 470                 475                 480 gtc ccg gtg gca tac gtt gtt cgc tcg cct aac agt tcg ttg acc gaa      1488
Val Pro Val Ala Tyr Val Val Arg Ser Pro Asn Ser Ser Leu Thr Glu
                485                 490                 495 aat gac gtt aaa aaa ttc atc gcc ggt cag gtc gcc tcc ttt aag cgt      1536
Asn Asp Val Lys Lys Phe Ile Ala Gly Gln Val Ala Ser Phe Lys Arg
            500                 505                 510 ctg cgc aag gtt act ttt att aat tcc gtc ccc aag agc gca agt ggg      1584
Leu Arg Lys Val Thr Phe Ile Asn Ser Val Pro Lys Ser Ala Ser Gly
        515                 520                 525 aag att ctg cgc cgc gag ctt att caa aag gtt cgc tct aac atg taa      1632
Lys Ile Leu Arg Arg Glu Leu Ile Gln Lys Val Arg Ser Asn Met
    530                 535                 540

<210> SEQ ID NO 71
<211> LENGTH: 543
<212> TYPE: PRT
<213> ORGANISM: Cannabis sativa

<400> SEQUENCE: 71

Met Glu Lys Ser Gly Tyr Gly Arg Asp Gly Ile Tyr Arg Ser Leu Arg
1               5                   10                  15

Pro Pro Leu His Leu Pro Asn Asn Asn Leu Ser Met Val Ser Phe
                20                  25                  30

Leu Phe Arg Asn Ser Ser Tyr Pro Gln Lys Pro Ala Leu Ile Asp
        35                  40                  45

Ser Glu Thr Asn Gln Ile Leu Ser Phe Ser His Phe Lys Ser Thr Val
50                  55                  60

Ile Lys Val Ser His Gly Phe Leu Asn Leu Gly Ile Lys Lys Asn Asp
65                  70                  75                  80

Val Val Leu Ile Tyr Ala Pro Asn Ser Ile His Phe Pro Val Cys Phe
                85                  90                  95

Leu Gly Ile Ile Ala Ser Gly Ala Ile Ala Thr Thr Ser Asn Pro Leu
            100                 105                 110

Tyr Thr Val Ser Glu Leu Ser Lys Gln Val Lys Asp Ser Asn Pro Lys
        115                 120                 125

Leu Ile Ile Thr Val Pro Gln Leu Leu Glu Lys Val Lys Gly Phe Asn
130                 135                 140

Leu Pro Thr Ile Leu Ile Gly Pro Asp Ser Glu Gln Glu Ser Ser Ser
145                 150                 155                 160

Asp Lys Val Met Thr Phe Asn Asp Leu Val Asn Leu Gly Gly Ser Ser
                165                 170                 175

Gly Ser Glu Phe Pro Ile Val Asp Phe Lys Gln Ser Asp Thr Ala
            180                 185                 190

Ala Leu Leu Tyr Ser Ser Gly Thr Thr Gly Met Ser Lys Gly Val Val
        195                 200                 205

Leu Thr His Lys Asn Phe Ile Ala Ser Ser Leu Met Val Thr Met Glu
210                 215                 220

Gln Asp Leu Val Gly Glu Met Asp Asn Val Phe Leu Cys Phe Leu Pro
225                 230                 235                 240
```

```
Met Phe His Val Phe Gly Leu Ala Ile Ile Thr Tyr Ala Gln Leu Gln
                245                 250                 255

Arg Gly Asn Thr Val Ile Ser Met Ala Arg Phe Asp Leu Glu Lys Met
            260                 265                 270

Leu Lys Asp Val Glu Lys Tyr Lys Val Thr His Leu Trp Val Val Pro
        275                 280                 285

Pro Val Ile Leu Ala Leu Ser Lys Asn Ser Met Val Lys Lys Phe Asn
290                 295                 300

Leu Ser Ser Ile Lys Tyr Ile Gly Ser Gly Ala Pro Leu Gly Lys
305                 310                 315                 320

Asp Leu Met Glu Glu Cys Ser Lys Val Val Pro Tyr Gly Ile Val Ala
                325                 330                 335

Gln Gly Tyr Gly Met Thr Glu Thr Cys Gly Ile Val Ser Met Glu Asp
            340                 345                 350

Ile Arg Gly Gly Lys Arg Asn Ser Gly Ser Ala Gly Met Leu Ala Ser
        355                 360                 365

Gly Val Glu Ala Gln Ile Val Ser Val Asp Thr Leu Lys Pro Leu Pro
370                 375                 380

Pro Asn Gln Leu Gly Glu Ile Trp Val Lys Gly Pro Asn Met Met Gln
385                 390                 395                 400

Gly Tyr Phe Asn Asn Pro Gln Ala Thr Lys Leu Thr Ile Asp Lys Lys
                405                 410                 415

Gly Trp Val His Thr Gly Asp Leu Gly Tyr Phe Asp Glu Asp Gly His
            420                 425                 430

Leu Tyr Val Val Asp Arg Ile Lys Glu Leu Ile Lys Tyr Lys Gly Phe
        435                 440                 445

Gln Val Ala Pro Ala Glu Leu Glu Gly Leu Leu Val Ser His Pro Glu
    450                 455                 460

Ile Leu Asp Ala Val Val Ile Pro Phe Pro Asp Ala Glu Ala Gly Glu
465                 470                 475                 480

Val Pro Val Ala Tyr Val Val Arg Ser Pro Asn Ser Ser Leu Thr Glu
                485                 490                 495

Asn Asp Val Lys Lys Phe Ile Ala Gly Gln Val Ala Ser Phe Lys Arg
            500                 505                 510

Leu Arg Lys Val Thr Phe Ile Asn Ser Val Pro Lys Ser Ala Ser Gly
        515                 520                 525

Lys Ile Leu Arg Arg Glu Leu Ile Gln Lys Val Arg Ser Asn Met
    530                 535                 540

<210> SEQ ID NO 72
<211> LENGTH: 2163
<212> TYPE: DNA
<213> ORGANISM: Cannabis sativa
<220> FEATURE:
<221> NAME/KEY: CDS
<222> LOCATION: (1)..(2163)

<400> SEQUENCE: 72 atg ggt aag aat tac aag tcc ctg gac tct gtt gtg gcc tct gac ttc     48
Met Gly Lys Asn Tyr Lys Ser Leu Asp Ser Val Val Ala Ser Asp Phe
1               5                   10                  15 ata gcc cta ggt atc acc tct gaa gtt gct gag aca ctc cat ggt aga     96
Ile Ala Leu Gly Ile Thr Ser Glu Val Ala Glu Thr Leu His Gly Arg
            20                  25                  30 ctg gcc gag atc gtg tgt aat tat ggc gct gcc act ccc caa aca tgg    144
Leu Ala Glu Ile Val Cys Asn Tyr Gly Ala Ala Thr Pro Gln Thr Trp
        35                  40                  45
```

```
atc aat att gcc aac cat att ctg tcg cct gac ctc ccc ttc tcc ctg     192
Ile Asn Ile Ala Asn His Ile Leu Ser Pro Asp Leu Pro Phe Ser Leu
 50                  55                  60 cac cag atg ctc ttc tat ggt tgc tat aaa gac ttt gga cct gcc cct     240
His Gln Met Leu Phe Tyr Gly Cys Tyr Lys Asp Phe Gly Pro Ala Pro
 65                  70                  75                  80 cct gct tgg ata ccc gac ccg gag aaa gta aag tcc acc aat ctg ggc     288
Pro Ala Trp Ile Pro Asp Pro Glu Lys Val Lys Ser Thr Asn Leu Gly
                 85                  90                  95 gca ctt ttg gag aag cga gga aaa gag ttt ttg gga gtc aag tat aag     336
Ala Leu Leu Glu Lys Arg Gly Lys Glu Phe Leu Gly Val Lys Tyr Lys
            100                 105                 110 gat ccc att tca agc ttt tct cat ttc caa gaa ttt tct gta aga aac     384
Asp Pro Ile Ser Ser Phe Ser His Phe Gln Glu Phe Ser Val Arg Asn
            115                 120                 125 cct gag gtg tat tgg aga aca gta cta atg gat gag atg aag ata agt     432
Pro Glu Val Tyr Trp Arg Thr Val Leu Met Asp Glu Met Lys Ile Ser
130                 135                 140 ttt tca aag gat cca gaa tgt ata ttg cgt aga gat gat att aat aat     480
Phe Ser Lys Asp Pro Glu Cys Ile Leu Arg Arg Asp Asp Ile Asn Asn
145                 150                 155                 160 cca ggg ggt agt gaa tgg ctt cca gga ggt tat ctt aac tca gca aag     528
Pro Gly Gly Ser Glu Trp Leu Pro Gly Gly Tyr Leu Asn Ser Ala Lys
                165                 170                 175 aat tgc ttg aat gta aat agt aac aag aaa ttg aat gat aca atg att     576
Asn Cys Leu Asn Val Asn Ser Asn Lys Lys Leu Asn Asp Thr Met Ile
            180                 185                 190 gta tgg cgt gat gaa gga aat gat gat ttg cct cta aac aaa ttg aca     624
Val Trp Arg Asp Glu Gly Asn Asp Asp Leu Pro Leu Asn Lys Leu Thr
            195                 200                 205 ctt gac caa ttg cgt aaa cgt gtt tgg tta gtt ggt tat gca ctt gaa     672
Leu Asp Gln Leu Arg Lys Arg Val Trp Leu Val Gly Tyr Ala Leu Glu
            210                 215                 220 gaa atg ggt ttg gag aag ggt tgt gca att gca att gat atg cca atg     720
Glu Met Gly Leu Glu Lys Gly Cys Ala Ile Ala Ile Asp Met Pro Met
225                 230                 235                 240 cat gtg gat gct gtg gtt atc tat cta gct att gtt ctt gcg gga tat     768
His Val Asp Ala Val Val Ile Tyr Leu Ala Ile Val Leu Ala Gly Tyr
                245                 250                 255 gta gtt gtt tct att gct gat agt ttt tct gct cct gaa ata tca aca     816
Val Val Val Ser Ile Ala Asp Ser Phe Ser Ala Pro Glu Ile Ser Thr
            260                 265                 270 aga ctt cga cta tca aaa gca aaa gcc att ttt aca cag gat cat att     864
Arg Leu Arg Leu Ser Lys Ala Lys Ala Ile Phe Thr Gln Asp His Ile
            275                 280                 285 att cgt ggg aag aag cgt att ccc tta tac agt aga gtt gtg gaa gcc     912
Ile Arg Gly Lys Lys Arg Ile Pro Leu Tyr Ser Arg Val Val Glu Ala
            290                 295                 300 aag tct ccc atg gcc att gtt att cct tgt agt ggc tct aat att ggt     960
Lys Ser Pro Met Ala Ile Val Ile Pro Cys Ser Gly Ser Asn Ile Gly
305                 310                 315                 320 gca gaa ttg cgt gat ggc gat att tct tgg gat tac ttt cta gaa aga    1008
Ala Glu Leu Arg Asp Gly Asp Ile Ser Trp Asp Tyr Phe Leu Glu Arg
                325                 330                 335 gca aaa gag ttt aaa aat tgt gaa ttt act gct aga gaa caa cca gtt    1056
Ala Lys Glu Phe Lys Asn Cys Glu Phe Thr Ala Arg Glu Gln Pro Val
            340                 345                 350 gat gcc tat aca aac atc ctc ttc tca tct gga aca aca ggg gag cca    1104
Asp Ala Tyr Thr Asn Ile Leu Phe Ser Ser Gly Thr Thr Gly Glu Pro
```

```
                   355                 360                 365
aag gca att cca tgg act caa gca act cct tta aaa gca gct gca gat    1152
Lys Ala Ile Pro Trp Thr Gln Ala Thr Pro Leu Lys Ala Ala Ala Asp
    370                 375                 380 ggg tgg agc cat ttg gac att agg aaa ggt gat gtc att gtt tgg ccc    1200
Gly Trp Ser His Leu Asp Ile Arg Lys Gly Asp Val Ile Val Trp Pro
385                 390                 395                 400 act aat ctt ggt tgg atg atg ggt cct tgg ctg gtc tat gct tca ctc    1248
Thr Asn Leu Gly Trp Met Met Gly Pro Trp Leu Val Tyr Ala Ser Leu
                405                 410                 415 ctt aat ggg gct tct att gcc ttg tat aat gga tca cca ctt gtt tct    1296
Leu Asn Gly Ala Ser Ile Ala Leu Tyr Asn Gly Ser Pro Leu Val Ser
        420                 425                 430 ggc ttt gcc aaa ttt gtg cag gat gct aaa gta aca atg cta ggt gtg    1344
Gly Phe Ala Lys Phe Val Gln Asp Ala Lys Val Thr Met Leu Gly Val
    435                 440                 445 gtc cct agt att gtt cga tca tgg aaa agt acc aat tgt gtt agt ggc    1392
Val Pro Ser Ile Val Arg Ser Trp Lys Ser Thr Asn Cys Val Ser Gly
450                 455                 460 tat gat tgg tcc acc atc cgt tgc ttt tcc tct tct ggt gaa gca tct    1440
Tyr Asp Trp Ser Thr Ile Arg Cys Phe Ser Ser Ser Gly Glu Ala Ser
465                 470                 475                 480 aat gta gat gaa tac cta tgg ttg atg ggg aga gca aac tac aag cct    1488
Asn Val Asp Glu Tyr Leu Trp Leu Met Gly Arg Ala Asn Tyr Lys Pro
                485                 490                 495 gtt atc gaa atg tgt ggt ggc aca gaa att ggt ggt gca ttt tct gct    1536
Val Ile Glu Met Cys Gly Gly Thr Glu Ile Gly Gly Ala Phe Ser Ala
        500                 505                 510 ggc tct ttc tta caa gct caa tca tta tct tca ttt agt tca caa tgt    1584
Gly Ser Phe Leu Gln Ala Gln Ser Leu Ser Ser Phe Ser Ser Gln Cys
    515                 520                 525 atg ggt tgc act tta tac ata ctt gac aag aat ggt tat cca atg cct    1632
Met Gly Cys Thr Leu Tyr Ile Leu Asp Lys Asn Gly Tyr Pro Met Pro
530                 535                 540 aaa aac aaa cca gga att ggt gaa tta gcg ctt ggt cca gtc atg ttt    1680
Lys Asn Lys Pro Gly Ile Gly Glu Leu Ala Leu Gly Pro Val Met Phe
545                 550                 555                 560 gga gca tcg aag act ctg ttg aat ggt aat cac cat gat gtt tat ttt    1728
Gly Ala Ser Lys Thr Leu Leu Asn Gly Asn His His Asp Val Tyr Phe
                565                 570                 575 aag gga atg cct aca ttg aat gga gag gtt tta agg agg cat ggg gac    1776
Lys Gly Met Pro Thr Leu Asn Gly Glu Val Leu Arg Arg His Gly Asp
        580                 585                 590 att ttt gag ctt aca tct aat ggt tat tat cat gca cat ggt cgt gca    1824
Ile Phe Glu Leu Thr Ser Asn Gly Tyr Tyr His Ala His Gly Arg Ala
    595                 600                 605 gat gat aca atg aat att gga ggc atc aag att agt tcc ata gag att    1872
Asp Asp Thr Met Asn Ile Gly Gly Ile Lys Ile Ser Ser Ile Glu Ile
610                 615                 620 gaa cga gtt tgt aat gaa gtt gat gac aga gtt ttc gag aca act gct    1920
Glu Arg Val Cys Asn Glu Val Asp Asp Arg Val Phe Glu Thr Thr Ala
625                 630                 635                 640 att gga gtg cca cct ttg ggc ggt gga cct gag caa tta gta att ttc    1968
Ile Gly Val Pro Pro Leu Gly Gly Gly Pro Glu Gln Leu Val Ile Phe
                645                 650                 655 ttt gta tta aaa gat tca aat gat aca act att gac tta aat caa ttg    2016
Phe Val Leu Lys Asp Ser Asn Asp Thr Thr Ile Asp Leu Asn Gln Leu
        660                 665                 670 agg tta tct ttc aac ttg ggt tta cag aag aaa cta aat cct ctg ttc    2064
```

```
                Arg Leu Ser Phe Asn Leu Gly Leu Gln Lys Lys Leu Asn Pro Leu Phe
                            675                 680                 685 aag gtc act cgt gtt gtg cct ctt tca tca ctt ccg aga aca gca acc                 2112
Lys Val Thr Arg Val Val Pro Leu Ser Ser Leu Pro Arg Thr Ala Thr
        690                 695                 700 aac aag atc atg aga agg gtt ttg cgc cag caa ttt tct cac ttt gaa                 2160
Asn Lys Ile Met Arg Arg Val Leu Arg Gln Gln Phe Ser His Phe Glu
705                 710                 715                 720 tga                                                                             2163

<210> SEQ ID NO 73
<211> LENGTH: 720
<212> TYPE: PRT
<213> ORGANISM: Cannabis sativa

<400> SEQUENCE: 73

Met Gly Lys Asn Tyr Lys Ser Leu Asp Ser Val Val Ala Ser Asp Phe
1               5                   10                  15

Ile Ala Leu Gly Ile Thr Ser Glu Val Ala Glu Thr Leu His Gly Arg
            20                  25                  30

Leu Ala Glu Ile Val Cys Asn Tyr Gly Ala Ala Thr Pro Gln Thr Trp
        35                  40                  45

Ile Asn Ile Ala Asn His Ile Leu Ser Pro Asp Leu Pro Phe Ser Leu
    50                  55                  60

His Gln Met Leu Phe Tyr Gly Cys Tyr Lys Asp Phe Gly Pro Ala Pro
65                  70                  75                  80

Pro Ala Trp Ile Pro Asp Pro Glu Lys Val Lys Ser Thr Asn Leu Gly
                85                  90                  95

Ala Leu Leu Glu Lys Arg Gly Lys Glu Phe Leu Gly Val Lys Tyr Lys
            100                 105                 110

Asp Pro Ile Ser Ser Phe Ser His Phe Gln Glu Phe Ser Val Arg Asn
        115                 120                 125

Pro Glu Val Tyr Trp Arg Thr Val Leu Met Asp Glu Met Lys Ile Ser
    130                 135                 140

Phe Ser Lys Asp Pro Glu Cys Ile Leu Arg Arg Asp Asp Ile Asn Asn
145                 150                 155                 160

Pro Gly Gly Ser Glu Trp Leu Pro Gly Gly Tyr Leu Asn Ser Ala Lys
                165                 170                 175

Asn Cys Leu Asn Val Asn Ser Asn Lys Lys Leu Asn Asp Thr Met Ile
            180                 185                 190

Val Trp Arg Asp Glu Gly Asn Asp Asp Leu Pro Leu Asn Lys Leu Thr
        195                 200                 205

Leu Asp Gln Leu Arg Lys Arg Val Trp Leu Val Gly Tyr Ala Leu Glu
    210                 215                 220

Glu Met Gly Leu Glu Lys Gly Cys Ala Ile Ala Ile Asp Met Pro Met
225                 230                 235                 240

His Val Asp Ala Val Val Ile Tyr Leu Ala Ile Val Leu Ala Gly Tyr
                245                 250                 255

Val Val Val Ser Ile Ala Asp Ser Phe Ser Ala Pro Glu Ile Ser Thr
            260                 265                 270

Arg Leu Arg Leu Ser Lys Ala Lys Ala Ile Phe Thr Gln Asp His Ile
        275                 280                 285

Ile Arg Gly Lys Lys Arg Ile Pro Leu Tyr Ser Arg Val Val Glu Ala
    290                 295                 300

Lys Ser Pro Met Ala Ile Val Ile Pro Cys Ser Gly Ser Asn Ile Gly
```

|     |     |     |     |     |     |     |     |     |     |     |     |
|-----|-----|-----|-----|-----|-----|-----|-----|-----|-----|-----|-----|
| 305 |     |     |     |     | 310 |     |     |     |     | 315 |     |     |     |     | 320 |

Ala Glu Leu Arg Asp Gly Asp Ile Ser Trp Asp Tyr Phe Leu Glu Arg
              325             330            335

Ala Lys Glu Phe Lys Asn Cys Glu Phe Thr Ala Arg Glu Gln Pro Val
              340             345            350

Asp Ala Tyr Thr Asn Ile Leu Phe Ser Ser Gly Thr Thr Gly Glu Pro
              355             360            365

Lys Ala Ile Pro Trp Thr Gln Ala Thr Pro Leu Lys Ala Ala Ala Asp
370             375             380

Gly Trp Ser His Leu Asp Ile Arg Lys Gly Asp Val Ile Val Trp Pro
385             390             395            400

Thr Asn Leu Gly Trp Met Met Gly Pro Trp Leu Val Tyr Ala Ser Leu
              405             410            415

Leu Asn Gly Ala Ser Ile Ala Leu Tyr Asn Gly Ser Pro Leu Val Ser
              420             425            430

Gly Phe Ala Lys Phe Val Gln Asp Ala Lys Val Thr Met Leu Gly Val
              435             440            445

Val Pro Ser Ile Val Arg Ser Trp Lys Ser Thr Asn Cys Val Ser Gly
              450             455            460

Tyr Asp Trp Ser Thr Ile Arg Cys Phe Ser Ser Ser Gly Glu Ala Ser
465             470             475            480

Asn Val Asp Glu Tyr Leu Trp Leu Met Gly Arg Ala Asn Tyr Lys Pro
              485             490            495

Val Ile Glu Met Cys Gly Gly Thr Glu Ile Gly Gly Ala Phe Ser Ala
              500             505            510

Gly Ser Phe Leu Gln Ala Gln Ser Leu Ser Ser Phe Ser Ser Gln Cys
              515             520            525

Met Gly Cys Thr Leu Tyr Ile Leu Asp Lys Asn Gly Tyr Pro Met Pro
              530             535            540

Lys Asn Lys Pro Gly Ile Gly Glu Leu Ala Leu Gly Pro Val Met Phe
545             550             555            560

Gly Ala Ser Lys Thr Leu Leu Asn Gly Asn His His Asp Val Tyr Phe
              565             570            575

Lys Gly Met Pro Thr Leu Asn Gly Glu Val Leu Arg Arg His Gly Asp
              580             585            590

Ile Phe Glu Leu Thr Ser Asn Gly Tyr Tyr His Ala His Gly Arg Ala
              595             600            605

Asp Asp Thr Met Asn Ile Gly Gly Ile Lys Ile Ser Ser Ile Glu Ile
610             615             620

Glu Arg Val Cys Asn Glu Val Asp Asp Arg Val Phe Glu Thr Thr Ala
625             630             635            640

Ile Gly Val Pro Pro Leu Gly Gly Gly Pro Glu Gln Leu Val Ile Phe
              645             650            655

Phe Val Leu Lys Asp Ser Asn Asp Thr Thr Ile Asp Leu Asn Gln Leu
              660             665            670

Arg Leu Ser Phe Asn Leu Gly Leu Gln Lys Lys Leu Asn Pro Leu Phe
              675             680            685

Lys Val Thr Arg Val Val Pro Leu Ser Ser Leu Pro Arg Thr Ala Thr
              690             695            700

Asn Lys Ile Met Arg Arg Val Leu Arg Gln Gln Phe Ser His Phe Glu
705             710             715            720

<210> SEQ ID NO 74

```
<211> LENGTH: 1695
<212> TYPE: DNA
<213> ORGANISM: Cannabis sativa
<220> FEATURE:
<221> NAME/KEY: CDS
<222> LOCATION: (1)..(1695)

<400> SEQUENCE: 74 atg gaa gta ctg aag gag gtt gcg aag gaa ggt agc gca gcc cgt gaa      48
Met Glu Val Leu Lys Glu Val Ala Lys Glu Gly Ser Ala Ala Arg Glu
1               5                  10                  15 ggt gtc gct att cgc gcc gac cag aaa tcg tac agc tat aag caa ttg      96
Gly Val Ala Ile Arg Ala Asp Gln Lys Ser Tyr Ser Tyr Lys Gln Leu
            20                  25                  30 atc tcc tcc gcg cag tcg atc tgc tca ctg tta tgc ggt act gaa ctt     144
Ile Ser Ser Ala Gln Ser Ile Cys Ser Leu Leu Cys Gly Thr Glu Leu
        35                  40                  45 aaa gcg att cac gaa gcc ggg aaa caa gct cgt cct agc gcg tct atc     192
Lys Ala Ile His Glu Ala Gly Lys Gln Ala Arg Pro Ser Ala Ser Ile
    50                  55                  60 aat ggg gcc ggg ggt cac ggc cac ttg gga gga gct cgt att gga att     240
Asn Gly Ala Gly Gly His Gly His Leu Gly Gly Ala Arg Ile Gly Ile
65                  70                  75                  80 gtt gct aag ccg tcg gca gaa ttt gta gcc ggt gtt tta ggt acg tgg     288
Val Ala Lys Pro Ser Ala Glu Phe Val Ala Gly Val Leu Gly Thr Trp
                85                  90                  95 tta tct ggt gga gtt gcg gtt ccc ctt gca ctg tct tac ccg gag gcg     336
Leu Ser Gly Gly Val Ala Val Pro Leu Ala Leu Ser Tyr Pro Glu Ala
            100                 105                 110 gaa tta ctg cat gtc atg aac gat tca gat atc agc atg atc ttg agc     384
Glu Leu Leu His Val Met Asn Asp Ser Asp Ile Ser Met Ile Leu Ser
        115                 120                 125 acg gaa gac cat caa gaa ctg atg caa aat att gct gcc aag act tcc     432
Thr Glu Asp His Gln Glu Leu Met Gln Asn Ile Ala Ala Lys Thr Ser
    130                 135                 140 gca cag ttt tcc tta att cca tct gtg ccg tcg tcg tgc tca caa gaa     480
Ala Gln Phe Ser Leu Ile Pro Ser Val Pro Ser Ser Cys Ser Gln Glu
145                 150                 155                 160 gta gcg gtc gat cat cgt cag acc ggt gac atc tct acc gac tct atc     528
Val Ala Val Asp His Arg Gln Thr Gly Asp Ile Ser Thr Asp Ser Ile
                165                 170                 175 ttg ctt aac cgc gag atc tct aac gag aat ccc gca ctt atc gtc tat     576
Leu Leu Asn Arg Glu Ile Ser Asn Glu Asn Pro Ala Leu Ile Val Tyr
            180                 185                 190 acg tcg ggg acg aca ggc aag ccg aag ggc gtc gtt cac aca cac caa     624
Thr Ser Gly Thr Thr Gly Lys Pro Lys Gly Val Val His Thr His Gln
        195                 200                 205 tca att tct gca cag gtt cag acg tta gcc aag gca tgg gag tat act     672
Ser Ile Ser Ala Gln Val Gln Thr Leu Ala Lys Ala Trp Glu Tyr Thr
    210                 215                 220 cct gcc gat caa ttc tta cac tgc tta ccg ctg cat cat gtg cat ggg     720
Pro Ala Asp Gln Phe Leu His Cys Leu Pro Leu His His Val His Gly
225                 230                 235                 240 ctg ttt aac gca ctg ttc gcg ccc ctt tac gcg cgt tca aca gtt gaa     768
Leu Phe Asn Ala Leu Phe Ala Pro Leu Tyr Ala Arg Ser Thr Val Glu
                245                 250                 255 ttt ctg ccg aaa ttt tct gtc cgc ggt att tgg caa cgc tgg cgc gaa     816
Phe Leu Pro Lys Phe Ser Val Arg Gly Ile Trp Gln Arg Trp Arg Glu
            260                 265                 270 tcc tac cca acg tca gag acg aaa gcc aat gac tgc att acg gta ttt     864
Ser Tyr Pro Thr Ser Glu Thr Lys Ala Asn Asp Cys Ile Thr Val Phe
```

-continued

```
                    275                 280                 285
aca gga gtt ccc acc atg tac acg cgt ctg att caa gga tat gaa gct      912
Thr Gly Val Pro Thr Met Tyr Thr Arg Leu Ile Gln Gly Tyr Glu Ala
290                 295                 300 atg gat cca gag tta aaa gag gcc tct gca tct gct gct aag cag ctg      960
Met Asp Pro Glu Leu Lys Glu Ala Ser Ala Ser Ala Ala Lys Gln Leu
305                 310                 315                 320 cgc ctt atg atg tgt ggt tcc tct gcg ctg cca gtt cct gtc atg cag     1008
Arg Leu Met Met Cys Gly Ser Ser Ala Leu Pro Val Pro Val Met Gln
                325                 330                 335 cag tgg caa acc atc acc ggc cac cgt ctt ctg gaa cgt tac gga atg     1056
Gln Trp Gln Thr Ile Thr Gly His Arg Leu Leu Glu Arg Tyr Gly Met
            340                 345                 350 acc gaa ttt gtc atg gca att tct aac ccc ttg aaa ggt gag cgc aaa     1104
Thr Glu Phe Val Met Ala Ile Ser Asn Pro Leu Lys Gly Glu Arg Lys
        355                 360                 365 tcc ggt act gtc gga aag ccg ttt cca ggt gta gag gtg cgc att tta     1152
Ser Gly Thr Val Gly Lys Pro Phe Pro Gly Val Glu Val Arg Ile Leu
370                 375                 380 gca gag gat gaa aac ggc gat gat gct acc ggg gtg gga gag ctg tgc     1200
Ala Glu Asp Glu Asn Gly Asp Asp Ala Thr Gly Val Gly Glu Leu Cys
385                 390                 395                 400 gta cgc agt ccg tcc ctt ttc aaa gag tat tgg cgt ttg ccc gag gtc     1248
Val Arg Ser Pro Ser Leu Phe Lys Glu Tyr Trp Arg Leu Pro Glu Val
                405                 410                 415 aca aaa gcc tcc ttt aca gac gac ggc ttt ttc aaa acc ggc gac gca     1296
Thr Lys Ala Ser Phe Thr Asp Asp Gly Phe Phe Lys Thr Gly Asp Ala
            420                 425                 430 ggc aag gtc gat gag gac ggt tac tac gtg att ctg ggc cgt act agc     1344
Gly Lys Val Asp Glu Asp Gly Tyr Tyr Val Ile Leu Gly Arg Thr Ser
        435                 440                 445 gca gat att atg aaa gtt gga ggc tat aag ctg tct gct ctg gaa atc     1392
Ala Asp Ile Met Lys Val Gly Gly Tyr Lys Leu Ser Ala Leu Glu Ile
450                 455                 460 gag tcg gtc ctt ctg gaa cac ccg act gtc gag gaa tgc tgt gtc ttg     1440
Glu Ser Val Leu Leu Glu His Pro Thr Val Glu Glu Cys Cys Val Leu
465                 470                 475                 480 gga ctt ccc gac aag gat tat ggg gaa gcc gta tcc gca atc att gta     1488
Gly Leu Pro Asp Lys Asp Tyr Gly Glu Ala Val Ser Ala Ile Ile Val
                485                 490                 495 ccg gca gcc gag gcg aag aag aaa cgc gaa gag gag tca cgc ccc gcc     1536
Pro Ala Ala Glu Ala Lys Lys Lys Arg Glu Glu Glu Ser Arg Pro Ala
            500                 505                 510 att agt ctg gag gaa ctg ttc tca tgg gca cag cac aaa ctt gcc ccc     1584
Ile Ser Leu Glu Glu Leu Phe Ser Trp Ala Gln His Lys Leu Ala Pro
        515                 520                 525 tac aaa ctg ccc acg cgt tta ttc ctg tgg gac tct tta cct cgc aac     1632
Tyr Lys Leu Pro Thr Arg Leu Phe Leu Trp Asp Ser Leu Pro Arg Asn
530                 535                 540 gca atg ggg aaa gtc aac aaa aaa gag ctg aag aaa aaa ctg aca gtt     1680
Ala Met Gly Lys Val Asn Lys Lys Glu Leu Lys Lys Lys Leu Thr Val
545                 550                 555                 560 gag caa ggt att taa                                                  1695
Glu Gln Gly Ile
```

<210> SEQ ID NO 75
<211> LENGTH: 564
<212> TYPE: PRT
<213> ORGANISM: Cannabis sativa

<400> SEQUENCE: 75

```
Met Glu Val Leu Lys Glu Val Ala Lys Glu Gly Ser Ala Ala Arg Glu
1               5                   10                  15
Gly Val Ala Ile Arg Ala Asp Gln Lys Ser Tyr Ser Tyr Lys Gln Leu
            20                  25                  30
Ile Ser Ala Gln Ser Ile Cys Ser Leu Leu Cys Gly Thr Glu Leu
        35                  40                  45
Lys Ala Ile His Glu Ala Gly Lys Gln Ala Arg Pro Ser Ala Ser Ile
    50                  55                  60
Asn Gly Ala Gly Gly His Gly His Leu Gly Gly Ala Arg Ile Gly Ile
65                  70                  75                  80
Val Ala Lys Pro Ser Ala Glu Phe Val Ala Gly Val Leu Gly Thr Trp
                85                  90                  95
Leu Ser Gly Gly Val Ala Val Pro Leu Ala Leu Ser Tyr Pro Glu Ala
            100                 105                 110
Glu Leu Leu His Val Met Asn Asp Ser Asp Ile Ser Met Ile Leu Ser
        115                 120                 125
Thr Glu Asp His Gln Glu Leu Met Gln Asn Ile Ala Ala Lys Thr Ser
130                 135                 140
Ala Gln Phe Ser Leu Ile Pro Ser Val Pro Ser Ser Cys Ser Gln Glu
145                 150                 155                 160
Val Ala Val Asp His Arg Gln Thr Gly Asp Ile Ser Thr Asp Ser Ile
                165                 170                 175
Leu Leu Asn Arg Glu Ile Ser Asn Glu Asn Pro Ala Leu Ile Val Tyr
            180                 185                 190
Thr Ser Gly Thr Thr Gly Lys Pro Lys Gly Val Val His Thr His Gln
        195                 200                 205
Ser Ile Ser Ala Gln Val Gln Thr Leu Ala Lys Ala Trp Glu Tyr Thr
210                 215                 220
Pro Ala Asp Gln Phe Leu His Cys Leu Pro Leu His His Val His Gly
225                 230                 235                 240
Leu Phe Asn Ala Leu Phe Ala Pro Leu Tyr Ala Arg Ser Thr Val Glu
                245                 250                 255
Phe Leu Pro Lys Phe Ser Val Arg Gly Ile Trp Gln Arg Trp Arg Glu
            260                 265                 270
Ser Tyr Pro Thr Ser Glu Thr Lys Ala Asn Asp Cys Ile Thr Val Phe
        275                 280                 285
Thr Gly Val Pro Thr Met Tyr Thr Arg Leu Ile Gln Gly Tyr Glu Ala
290                 295                 300
Met Asp Pro Glu Leu Lys Glu Ala Ser Ala Ser Ala Ala Lys Gln Leu
305                 310                 315                 320
Arg Leu Met Met Cys Gly Ser Ser Ala Leu Pro Val Pro Val Met Gln
                325                 330                 335
Gln Trp Gln Thr Ile Thr Gly His Arg Leu Leu Glu Arg Tyr Gly Met
            340                 345                 350
Thr Glu Phe Val Met Ala Ile Ser Asn Pro Leu Lys Gly Glu Arg Lys
        355                 360                 365
Ser Gly Thr Val Gly Lys Pro Phe Pro Gly Val Glu Val Arg Ile Leu
370                 375                 380
Ala Glu Asp Glu Asn Gly Asp Asp Ala Thr Gly Val Gly Glu Leu Cys
385                 390                 395                 400
Val Arg Ser Pro Ser Leu Phe Lys Glu Tyr Trp Arg Leu Pro Glu Val
                405                 410                 415
```

```
Thr Lys Ala Ser Phe Thr Asp Gly Phe Lys Thr Gly Asp Ala
            420             425             430

Gly Lys Val Asp Glu Asp Gly Tyr Tyr Val Ile Leu Gly Arg Thr Ser
        435                 440                 445

Ala Asp Ile Met Lys Val Gly Gly Tyr Lys Leu Ser Ala Leu Glu Ile
450                 455                 460

Glu Ser Val Leu Leu Glu His Pro Thr Val Glu Glu Cys Cys Val Leu
465                 470                 475                 480

Gly Leu Pro Asp Lys Asp Tyr Gly Glu Ala Val Ser Ala Ile Ile Val
                485                 490                 495

Pro Ala Ala Glu Ala Lys Lys Lys Arg Glu Glu Glu Ser Arg Pro Ala
                500                 505                 510

Ile Ser Leu Glu Glu Leu Phe Ser Trp Ala Gln His Lys Leu Ala Pro
            515                 520                 525

Tyr Lys Leu Pro Thr Arg Leu Phe Leu Trp Asp Ser Leu Pro Arg Asn
        530                 535                 540

Ala Met Gly Lys Val Asn Lys Lys Glu Leu Lys Lys Lys Leu Thr Val
545                 550                 555                 560

Glu Gln Gly Ile
```

<210> SEQ ID NO 76
<211> LENGTH: 1158
<212> TYPE: DNA
<213> ORGANISM: Cannabis sativa
<220> FEATURE:
<221> NAME/KEY: CDS
<222> LOCATION: (1)..(1158)

<400> SEQUENCE: 76

```
atg aat cat ctg cgt gct gaa gga cca gct tcc gta ttg gca att gga        48
Met Asn His Leu Arg Ala Glu Gly Pro Ala Ser Val Leu Ala Ile Gly
1               5                   10                  15 aca gct aac cct gag aac att ctt ctt cag gat gag ttt ccc gac tat       96
Thr Ala Asn Pro Glu Asn Ile Leu Leu Gln Asp Glu Phe Pro Asp Tyr
            20                  25                  30 tac ttc cgc gtg aca aag agc gaa cac atg aca cag ctt aaa gag aag      144
Tyr Phe Arg Val Thr Lys Ser Glu His Met Thr Gln Leu Lys Glu Lys
        35                  40                  45 ttc cgt aag atc tgt gac aaa agc atg atc cgc aaa cgt aac tgc ttc      192
Phe Arg Lys Ile Cys Asp Lys Ser Met Ile Arg Lys Arg Asn Cys Phe
    50                  55                  60 ctt aac gag gag cat ctg aag cag aat ccc cgt ctt gtt gaa cat gag      240
Leu Asn Glu Glu His Leu Lys Gln Asn Pro Arg Leu Val Glu His Glu
65                  70                  75                  80 atg cag acc ttg gat gct cgc cag gac atg ttg gtt gtt gag gtc cct      288
Met Gln Thr Leu Asp Ala Arg Gln Asp Met Leu Val Val Glu Val Pro
                85                  90                  95 aag ctg ggc aaa gat gcg tgt gca aaa gcg att aaa gag tgg ggc cag      336
Lys Leu Gly Lys Asp Ala Cys Ala Lys Ala Ile Lys Glu Trp Gly Gln
            100                 105                 110 cct aaa agc aaa att act cat ctg att ttc aca agc gcc agt aca acc      384
Pro Lys Ser Lys Ile Thr His Leu Ile Phe Thr Ser Ala Ser Thr Thr
        115                 120                 125 gat atg ccc ggt gcg gac tac cat tgt gca aaa tta ttg ggt tta tcg      432
Asp Met Pro Gly Ala Asp Tyr His Cys Ala Lys Leu Leu Gly Leu Ser
    130                 135                 140 cct tca gta aaa cgt gtt atg atg tac cag tta gga tgc tac ggt ggt      480
Pro Ser Val Lys Arg Val Met Met Tyr Gln Leu Gly Cys Tyr Gly Gly
145                 150                 155                 160
```

```
                145                 150                 155                 160
ggc acc gta ctt cgt att gcg aag gac atc gcc gag aac aac aaa gga        528
Gly Thr Val Leu Arg Ile Ala Lys Asp Ile Ala Glu Asn Asn Lys Gly
                165                 170                 175 gcc cgt gta ctt gct gta tgt tgt gat atc atg gcg tgc ctt ttt cgc        576
Ala Arg Val Leu Ala Val Cys Cys Asp Ile Met Ala Cys Leu Phe Arg
                180                 185                 190 ggc ccc agc gag agt gac ctt gag tta ctt gtg ggg cag gcc atc ttc        624
Gly Pro Ser Glu Ser Asp Leu Glu Leu Leu Val Gly Gln Ala Ile Phe
                195                 200                 205 gga gac ggt gcc gca gcc gtc att gtt ggc gca gag ccc gat gaa tcc        672
Gly Asp Gly Ala Ala Ala Val Ile Val Gly Ala Glu Pro Asp Glu Ser
        210                 215                 220 gtt ggc gag cgc ccg atc ttt gag ctt gta agt aca gga caa act atc        720
Val Gly Glu Arg Pro Ile Phe Glu Leu Val Ser Thr Gly Gln Thr Ile
225                 230                 235                 240 ttg ccc aac tct gag ggg act atc ggc gga cat att cgt gag gcg ggc        768
Leu Pro Asn Ser Glu Gly Thr Ile Gly Gly His Ile Arg Glu Ala Gly
                245                 250                 255 ttg att ttt gac ctt cac aag gat gtt cca atg ctt atc tcc aat aat        816
Leu Ile Phe Asp Leu His Lys Asp Val Pro Met Leu Ile Ser Asn Asn
            260                 265                 270 att gaa aaa tgt ctt atc gaa gca ttc act ccg att ggt atc tcc gat        864
Ile Glu Lys Cys Leu Ile Glu Ala Phe Thr Pro Ile Gly Ile Ser Asp
        275                 280                 285 tgg aat tcg att ttt tgg atc acc cat cct ggt ggg aaa gct att tta        912
Trp Asn Ser Ile Phe Trp Ile Thr His Pro Gly Gly Lys Ala Ile Leu
        290                 295                 300 gac aag gtg gag gag aaa tta cat ctt aag tca gat aag ttt gtc gac        960
Asp Lys Val Glu Glu Lys Leu His Leu Lys Ser Asp Lys Phe Val Asp
305                 310                 315                 320 agt cgc cac gtg ttg tcg gaa cat ggc aac atg tca tcg tca acc gtc       1008
Ser Arg His Val Leu Ser Glu His Gly Asn Met Ser Ser Ser Thr Val
                325                 330                 335 ttg ttc gtt atg gac gaa tta cgt aaa cgc agt tta gaa gag ggt aag       1056
Leu Phe Val Met Asp Glu Leu Arg Lys Arg Ser Leu Glu Glu Gly Lys
                340                 345                 350 agt acg acg ggg gac ggg ttc gag tgg gga gtc tta ttc ggg ttc ggt       1104
Ser Thr Thr Gly Asp Gly Phe Glu Trp Gly Val Leu Phe Gly Phe Gly
                355                 360                 365 cca gga ttg aca gtg gaa cgc gtc gtg gtt cgc agt gtc ccc att aag       1152
Pro Gly Leu Thr Val Glu Arg Val Val Val Arg Ser Val Pro Ile Lys
        370                 375                 380 tac taa                                                                1158
Tyr
385

<210> SEQ ID NO 77
<211> LENGTH: 385
<212> TYPE: PRT
<213> ORGANISM: Cannabis sativa

<400> SEQUENCE: 77

Met Asn His Leu Arg Ala Glu Gly Pro Ala Ser Val Leu Ala Ile Gly
1               5                   10                  15

Thr Ala Asn Pro Glu Asn Ile Leu Leu Gln Asp Glu Phe Pro Asp Tyr
            20                  25                  30

Tyr Phe Arg Val Thr Lys Ser Glu His Met Thr Gln Leu Lys Glu Lys
        35                  40                  45
```

```
Phe Arg Lys Ile Cys Asp Lys Ser Met Ile Arg Lys Arg Asn Cys Phe
 50                  55                  60

Leu Asn Glu Glu His Leu Lys Gln Asn Pro Arg Leu Val Glu His Glu
 65                  70                  75                  80

Met Gln Thr Leu Asp Ala Arg Gln Asp Met Leu Val Val Glu Val Pro
                 85                  90                  95

Lys Leu Gly Lys Asp Ala Cys Ala Lys Ala Ile Lys Glu Trp Gly Gln
                100                 105                 110

Pro Lys Ser Lys Ile Thr His Leu Ile Phe Thr Ser Ala Ser Thr Thr
                115                 120                 125

Asp Met Pro Gly Ala Asp Tyr His Cys Ala Lys Leu Leu Gly Leu Ser
130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
                180                 185                 190

Gly Pro Ser Glu Ser Asp Leu Glu Leu Leu Val Gly Gln Ala Ile Phe
                195                 200                 205

Gly Asp Gly Ala Ala Ala Val Ile Val Gly Ala Glu Pro Asp Glu Ser
210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
                260                 265                 270

Ile Glu Lys Cys Leu Ile Glu Ala Phe Thr Pro Ile Gly Ile Ser Asp
                275                 280                 285

Trp Asn Ser Ile Phe Trp Ile Thr His Pro Gly Gly Lys Ala Ile Leu
                290                 295                 300

Asp Lys Val Glu Glu Lys Leu His Leu Lys Ser Asp Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
                340                 345                 350

Ser Thr Thr Gly Asp Gly Phe Glu Trp Gly Val Leu Phe Gly Phe Gly
                355                 360                 365

Pro Gly Leu Thr Val Glu Arg Val Val Arg Ser Val Pro Ile Lys
                370                 375                 380

Tyr
385

<210> SEQ ID NO 78
<211> LENGTH: 306
<212> TYPE: DNA
<213> ORGANISM: Cannabis sativa
<220> FEATURE:
<221> NAME/KEY: CDS
<222> LOCATION: (1)..(306)

<400> SEQUENCE: 78 atg gca gtc aaa cac ttg atc gtg tta aag ttc aaa gat gaa atc aca        48
Met Ala Val Lys His Leu Ile Val Leu Lys Phe Lys Asp Glu Ile Thr
```

```
                1               5                    10                    15
    gag gct cag aag gaa gaa ttt ttc aag acg tat gta aac ctt gtt aat        96
    Glu Ala Gln Lys Glu Glu Phe Phe Lys Thr Tyr Val Asn Leu Val Asn
                    20                   25                   30 atc atc ccc gct atg aag gat gtg tat tgg ggt aaa gac gtg aca cag       144
    Ile Ile Pro Ala Met Lys Asp Val Tyr Trp Gly Lys Asp Val Thr Gln
                35                   40                   45 aag aac aaa gag gaa ggc tac acg cac atc gta gag gtc aca ttt gag       192
    Lys Asn Lys Glu Glu Gly Tyr Thr His Ile Val Glu Val Thr Phe Glu
        50                   55                   60 agc gtc gaa act att cag gat tac atc att cat ccc gca cac gtt gga       240
    Ser Val Glu Thr Ile Gln Asp Tyr Ile Ile His Pro Ala His Val Gly
    65                   70                   75                   80 ttc ggg gat gtg tat cgc tct ttc tgg gaa aaa ttg ctg atc ttc gac       288
    Phe Gly Asp Val Tyr Arg Ser Phe Trp Glu Lys Leu Leu Ile Phe Asp
                    85                   90                   95 tat aca ccg cgt aag taa                                               306
    Tyr Thr Pro Arg Lys
                100

<210> SEQ ID NO 79
<211> LENGTH: 101
<212> TYPE: PRT
<213> ORGANISM: Cannabis sativa

<400> SEQUENCE: 79

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
                20                  25                  30

Ile Ile Pro Ala Met Lys Asp Val Tyr Trp Gly Lys Asp Val Thr Gln
            35                  40                  45

Lys Asn Lys Glu Glu Gly Tyr Thr His Ile Val Glu Val Thr Phe Glu
        50                  55                  60

Ser Val Glu Thr Ile Gln Asp Tyr Ile Ile His Pro Ala His Val Gly
65                  70                  75                  80

Phe Gly Asp Val Tyr Arg Ser Phe Trp Glu Lys Leu Leu Ile Phe Asp
                85                  90                  95

Tyr Thr Pro Arg Lys
            100

<210> SEQ ID NO 80
<211> LENGTH: 654
<212> TYPE: DNA
<213> ORGANISM: Geobacillus thermodenitrificans
<220> FEATURE:
<221> NAME/KEY: CDS
<222> LOCATION: (1)..(654)

<400> SEQUENCE: 80 atg aat tta gtg ctg atg ggg ctg cca ggt gcc ggc aaa ggc acg caa        48
Met Asn Leu Val Leu Met Gly Leu Pro Gly Ala Gly Lys Gly Thr Gln
1               5                   10                  15 gcc gag aaa atc gta gaa aca tat gga atc cca cat att tca acc ggg        96
Ala Glu Lys Ile Val Glu Thr Tyr Gly Ile Pro His Ile Ser Thr Gly
                20                  25                  30 gat atg ttt cgg gcg gcg atg aaa gaa ggc aca ccg tta gga ttg cag       144
Asp Met Phe Arg Ala Ala Met Lys Glu Gly Thr Pro Leu Gly Leu Gln
            35                  40                  45 gca aaa gaa tat atc gac cgt ggt gat ctt gtt ccg gat gag gtg acg       192
Ala Lys Glu Tyr Ile Asp Arg Gly Asp Leu Val Pro Asp Glu Val Thr
```

```
                                                    -continued

Ala Lys Glu Tyr Ile Asp Arg Gly Asp Leu Val Pro Asp Glu Val Thr
    50                  55                  60 atc ggt atc gtc cgt gaa cgg tta agc aaa gac gac tgc caa aac ggc    240
Ile Gly Ile Val Arg Glu Arg Leu Ser Lys Asp Asp Cys Gln Asn Gly
65                  70                  75                  80 ttt ttg ctt gac gga ttc cca cgc acg gtt gcc caa gcg gag gcg ctg    288
Phe Leu Leu Asp Gly Phe Pro Arg Thr Val Ala Gln Ala Glu Ala Leu
                85                  90                  95 gaa gcg atg ctg gct gaa atc ggc cgc aag ctt gac tat gtc atc cat    336
Glu Ala Met Leu Ala Glu Ile Gly Arg Lys Leu Asp Tyr Val Ile His
            100                 105                 110 atc gat gtt cgc caa gat gtg tta atg gag cgc ctc aca gga aga cga    384
Ile Asp Val Arg Gln Asp Val Leu Met Glu Arg Leu Thr Gly Arg Arg
        115                 120                 125 att tgt cgc aac tgc gga gcg aca tac cat ctt gtt ttt cac cca ccg    432
Ile Cys Arg Asn Cys Gly Ala Thr Tyr His Leu Val Phe His Pro Pro
    130                 135                 140 gct cag cca ggc gta tgt gat aaa tgc ggt ggc gag ctt tat cag cgc    480
Ala Gln Pro Gly Val Cys Asp Lys Cys Gly Gly Glu Leu Tyr Gln Arg
145                 150                 155                 160 cct gac gat aat gaa gca aca gtg gcg aat cgg ctt gag gtg aat acg    528
Pro Asp Asp Asn Glu Ala Thr Val Ala Asn Arg Leu Glu Val Asn Thr
                165                 170                 175 aaa caa atg aag cca ttg ctc gat ttc tat gag caa aaa ggc tat ttg    576
Lys Gln Met Lys Pro Leu Leu Asp Phe Tyr Glu Gln Lys Gly Tyr Leu
            180                 185                 190 cgt cac att aac ggc gaa caa gaa atg gaa aaa gtg ttt agc gac att    624
Arg His Ile Asn Gly Glu Gln Glu Met Glu Lys Val Phe Ser Asp Ile
        195                 200                 205 cgc gaa ttg ctc ggg gga ctt act cga taa                            654
Arg Glu Leu Leu Gly Gly Leu Thr Arg
    210                 215

<210> SEQ ID NO 81
<211> LENGTH: 217
<212> TYPE: PRT
<213> ORGANISM: Geobacillus thermodenitrificans

<400> SEQUENCE: 81

Met Asn Leu Val Leu Met Gly Leu Pro Gly Ala Gly Lys Gly Thr Gln
1               5                   10                  15

Ala Glu Lys Ile Val Glu Thr Tyr Gly Ile Pro His Ile Ser Thr Gly
            20                  25                  30

Asp Met Phe Arg Ala Ala Met Lys Glu Gly Thr Pro Leu Gly Leu Gln
        35                  40                  45

Ala Lys Glu Tyr Ile Asp Arg Gly Asp Leu Val Pro Asp Glu Val Thr
    50                  55                  60

Ile Gly Ile Val Arg Glu Arg Leu Ser Lys Asp Asp Cys Gln Asn Gly
65                  70                  75                  80

Phe Leu Leu Asp Gly Phe Pro Arg Thr Val Ala Gln Ala Glu Ala Leu
                85                  90                  95

Glu Ala Met Leu Ala Glu Ile Gly Arg Lys Leu Asp Tyr Val Ile His
            100                 105                 110

Ile Asp Val Arg Gln Asp Val Leu Met Glu Arg Leu Thr Gly Arg Arg
        115                 120                 125

Ile Cys Arg Asn Cys Gly Ala Thr Tyr His Leu Val Phe His Pro Pro
    130                 135                 140

Ala Gln Pro Gly Val Cys Asp Lys Cys Gly Gly Glu Leu Tyr Gln Arg
```

-continued

```
            145                 150                 155                 160
Pro Asp Asp Asn Glu Ala Thr Val Ala Asn Arg Leu Glu Val Asn Thr
                    165                 170                 175
Lys Gln Met Lys Pro Leu Leu Asp Phe Tyr Glu Gln Lys Gly Tyr Leu
                180                 185                 190
Arg His Ile Asn Gly Glu Gln Glu Met Glu Lys Val Phe Ser Asp Ile
            195                 200                 205
Arg Glu Leu Leu Gly Gly Leu Thr Arg
    210                 215

<210> SEQ ID NO 82
<211> LENGTH: 1512
<212> TYPE: DNA
<213> ORGANISM: Rhodopseudomonas palustris
<220> FEATURE:
<221> NAME/KEY: CDS
<222> LOCATION: (1)..(1512)

<400> SEQUENCE: 82 atg aac gcc aac ctg ttc gcc cgc ctg ttc gat aag ctc gac gac ccc        48
Met Asn Ala Asn Leu Phe Ala Arg Leu Phe Asp Lys Leu Asp Asp Pro
1               5                   10                  15 cac aag ctc gcg atc gaa acc gcg gcc ggg gac aag atc agc tac gcc        96
His Lys Leu Ala Ile Glu Thr Ala Ala Gly Asp Lys Ile Ser Tyr Ala
            20                  25                  30 gag ctg gtg gcg cgg gcg ggc cgc gtc gcc aac gtg ctg gtg gca cgc       144
Glu Leu Val Ala Arg Ala Gly Arg Val Ala Asn Val Leu Val Ala Arg
        35                  40                  45 ggc ctg cag gtc ggc gac cgc gtt gcg gcg caa acc gag aag tcg gtg       192
Gly Leu Gln Val Gly Asp Arg Val Ala Ala Gln Thr Glu Lys Ser Val
    50                  55                  60 gaa gcg ctg gtg ctg tat ctc gcc acg gtg cgg gcc ggc ggc gtg tat       240
Glu Ala Leu Val Leu Tyr Leu Ala Thr Val Arg Ala Gly Gly Val Tyr
65                  70                  75                  80 ctg ccg ctc aac acc gcc tat acg ctg cac gag ctc gat tac ttc atc       288
Leu Pro Leu Asn Thr Ala Tyr Thr Leu His Glu Leu Asp Tyr Phe Ile
                85                  90                  95 acc gat gcc gag ccg aag atc gtg gtg tgc gat ccg tcc aag cgc gac       336
Thr Asp Ala Glu Pro Lys Ile Val Val Cys Asp Pro Ser Lys Arg Asp
            100                 105                 110 ggg atc gcg gcg att gcc gcc aag gtc ggc gcc acg gtg gag acg ctt       384
Gly Ile Ala Ala Ile Ala Ala Lys Val Gly Ala Thr Val Glu Thr Leu
        115                 120                 125 ggc ccc gac ggt cgg ggc tcg ctc acc gat gcg gca gct gga gcc agc       432
Gly Pro Asp Gly Arg Gly Ser Leu Thr Asp Ala Ala Ala Gly Ala Ser
    130                 135                 140 gag gcg ttc gcc acg atc gac cgc ggc gcc gat gat ctg gcg gcg atc       480
Glu Ala Phe Ala Thr Ile Asp Arg Gly Ala Asp Asp Leu Ala Ala Ile
145                 150                 155                 160 ctc tac acc tca ggg acg acc ggc cgc tcc aag ggc gcg atg ctc agc       528
Leu Tyr Thr Ser Gly Thr Thr Gly Arg Ser Lys Gly Ala Met Leu Ser
                165                 170                 175 cac gac aat ttg gcg tcg aac tcg ctg acg ctg gtc gat tac tgg cgc       576
His Asp Asn Leu Ala Ser Asn Ser Leu Thr Leu Val Asp Tyr Trp Arg
            180                 185                 190 ttc acg ccg gat gac gtg ctg atc cac gcg ctg ccg atc tat cac acc       624
Phe Thr Pro Asp Asp Val Leu Ile His Ala Leu Pro Ile Tyr His Thr
        195                 200                 205 cat gga ttg ttc gtg gcc agc aac gtc acg ctg ttc gcg cgc gga tcg       672
His Gly Leu Phe Val Ala Ser Asn Val Thr Leu Phe Ala Arg Gly Ser
```

```
                 210                 215                 220
atg atc ttc ctg ccg aag ttc gat ccc gac aag atc ctc gac ctg atg        720
Met Ile Phe Leu Pro Lys Phe Asp Pro Asp Lys Ile Leu Asp Leu Met
225                 230                 235                 240 gcg cgc gcc acc gtg ctg atg ggt gtg ccg acg ttc tac acg cgg ctc        768
Ala Arg Ala Thr Val Leu Met Gly Val Pro Thr Phe Tyr Thr Arg Leu
                245                 250                 255 ttg cag agc ccg cgg ctg acc aag gag acg acg ggc cac atg agg ctg        816
Leu Gln Ser Pro Arg Leu Thr Lys Glu Thr Thr Gly His Met Arg Leu
            260                 265                 270 ttc atc tcc ggg tcg gcg ccg ctg ctc gcc gat acg cat cgc gaa tgg        864
Phe Ile Ser Gly Ser Ala Pro Leu Leu Ala Asp Thr His Arg Glu Trp
        275                 280                 285 tcg gcg aag acc ggt cac gcc gtg ctc gag cgc tac ggc atg acc gag        912
Ser Ala Lys Thr Gly His Ala Val Leu Glu Arg Tyr Gly Met Thr Glu
    290                 295                 300 acc aac atg aac acc tcg aac ccg tat gac ggc gac cgc gtc ccc ggc        960
Thr Asn Met Asn Thr Ser Asn Pro Tyr Asp Gly Asp Arg Val Pro Gly
305                 310                 315                 320 gcg gtc ggc ccg gcg ctg ccc ggc gtt tcg gcg cgc gtg acc gat ccg       1008
Ala Val Gly Pro Ala Leu Pro Gly Val Ser Ala Arg Val Thr Asp Pro
                325                 330                 335 gaa acc ggc aag gaa ctg ccg cgc ggc gac atc ggg atg atc gag gtg       1056
Glu Thr Gly Lys Glu Leu Pro Arg Gly Asp Ile Gly Met Ile Glu Val
            340                 345                 350 aag ggc ccg aac gtg ttc aag ggc tac tgg cgg atg ccg gag aag acc       1104
Lys Gly Pro Asn Val Phe Lys Gly Tyr Trp Arg Met Pro Glu Lys Thr
        355                 360                 365 aag tct gaa ttc cgc gac gac ggc ttc ttc atc acc ggc gac ctc ggc       1152
Lys Ser Glu Phe Arg Asp Asp Gly Phe Phe Ile Thr Gly Asp Leu Gly
    370                 375                 380 aag atc gac gag cgc ggc tac gtc cac atc ctc ggc cgc ggc aag gat       1200
Lys Ile Asp Glu Arg Gly Tyr Val His Ile Leu Gly Arg Gly Lys Asp
385                 390                 395                 400 ctg gtg atc acc ggc ggc ttc aac gtc tat ccg aag gaa atc gag agc       1248
Leu Val Ile Thr Gly Gly Phe Asn Val Tyr Pro Lys Glu Ile Glu Ser
                405                 410                 415 gag atc gac gcc atg ccg ggc gtg gtc gaa tcc gcg gtg atc ggc gtg       1296
Glu Ile Asp Ala Met Pro Gly Val Val Glu Ser Ala Val Ile Gly Val
            420                 425                 430 ccg cac gcc gat ttc ggc gag ggc gtc act gcc gtg gtg gtg cgc gac       1344
Pro His Ala Asp Phe Gly Glu Gly Val Thr Ala Val Val Val Arg Asp
        435                 440                 445 aag ggt gcc acg atc gac gaa gcg cag gtg ctg cac ggc ctc gac ggt       1392
Lys Gly Ala Thr Ile Asp Glu Ala Gln Val Leu His Gly Leu Asp Gly
    450                 455                 460 cag ctc gcc aag ttc aag atg ccg aag aaa gtg atc ttc gtc gac gac       1440
Gln Leu Ala Lys Phe Lys Met Pro Lys Lys Val Ile Phe Val Asp Asp
465                 470                 475                 480 ctg ccg cgc aac acc atg ggc aag gtc cag aag aac gtc ctg cgc gag       1488
Leu Pro Arg Asn Thr Met Gly Lys Val Gln Lys Asn Val Leu Arg Glu
                485                 490                 495 acc tac aag gac atc tac aag taa                                        1512
Thr Tyr Lys Asp Ile Tyr Lys
            500

<210> SEQ ID NO 83
<211> LENGTH: 503
<212> TYPE: PRT
<213> ORGANISM: Rhodopseudomonas palustris
```

<400> SEQUENCE: 83

Met Asn Ala Asn Leu Phe Ala Arg Leu Phe Asp Lys Leu Asp Asp Pro
1               5                   10                  15

His Lys Leu Ala Ile Glu Thr Ala Ala Gly Asp Lys Ile Ser Tyr Ala
            20                  25                  30

Glu Leu Val Ala Arg Ala Gly Arg Val Ala Asn Val Leu Val Ala Arg
        35                  40                  45

Gly Leu Gln Val Gly Asp Arg Val Ala Ala Gln Thr Glu Lys Ser Val
    50                  55                  60

Glu Ala Leu Val Leu Tyr Leu Ala Thr Val Arg Ala Gly Gly Val Tyr
65                  70                  75                  80

Leu Pro Leu Asn Thr Ala Tyr Thr Leu His Glu Leu Asp Tyr Phe Ile
                85                  90                  95

Thr Asp Ala Glu Pro Lys Ile Val Val Cys Asp Pro Ser Lys Arg Asp
            100                 105                 110

Gly Ile Ala Ala Ile Ala Ala Lys Val Gly Ala Thr Val Glu Thr Leu
        115                 120                 125

Gly Pro Asp Gly Arg Gly Ser Leu Thr Asp Ala Ala Gly Ala Ser
    130                 135                 140

Glu Ala Phe Ala Thr Ile Asp Arg Gly Ala Asp Leu Ala Ala Ile
145                 150                 155                 160

Leu Tyr Thr Ser Gly Thr Thr Gly Arg Ser Lys Gly Ala Met Leu Ser
                165                 170                 175

His Asp Asn Leu Ala Ser Asn Ser Leu Thr Leu Val Asp Tyr Trp Arg
            180                 185                 190

Phe Thr Pro Asp Asp Val Leu Ile His Ala Leu Pro Ile Tyr His Thr
        195                 200                 205

His Gly Leu Phe Val Ala Ser Asn Val Thr Leu Phe Ala Arg Gly Ser
    210                 215                 220

Met Ile Phe Leu Pro Lys Phe Asp Pro Asp Lys Ile Leu Asp Leu Met
225                 230                 235                 240

Ala Arg Ala Thr Val Leu Met Gly Val Pro Thr Phe Tyr Thr Arg Leu
                245                 250                 255

Leu Gln Ser Pro Arg Leu Thr Lys Glu Thr Thr Gly His Met Arg Leu
            260                 265                 270

Phe Ile Ser Gly Ser Ala Pro Leu Leu Ala Asp Thr His Arg Glu Trp
        275                 280                 285

Ser Ala Lys Thr Gly His Ala Val Leu Glu Arg Tyr Gly Met Thr Glu
    290                 295                 300

Thr Asn Met Asn Thr Ser Asn Pro Tyr Asp Gly Asp Arg Val Pro Gly
305                 310                 315                 320

Ala Val Gly Pro Ala Leu Pro Gly Val Ser Ala Arg Val Thr Asp Pro
                325                 330                 335

Glu Thr Gly Lys Glu Leu Pro Arg Gly Asp Ile Gly Met Ile Glu Val
            340                 345                 350

Lys Gly Pro Asn Val Phe Lys Gly Tyr Trp Arg Met Pro Glu Lys Thr
        355                 360                 365

Lys Ser Glu Phe Arg Asp Asp Gly Phe Phe Ile Thr Gly Asp Leu Gly
    370                 375                 380

Lys Ile Asp Glu Arg Gly Tyr Val His Ile Leu Gly Arg Gly Lys Asp
385                 390                 395                 400

Leu Val Ile Thr Gly Gly Phe Asn Val Tyr Pro Lys Glu Ile Glu Ser

```
                    405                 410                 415
Glu Ile Asp Ala Met Pro Gly Val Val Glu Ser Ala Val Ile Gly Val
            420                 425                 430

Pro His Ala Asp Phe Gly Glu Gly Val Thr Ala Val Val Val Arg Asp
        435                 440                 445

Lys Gly Ala Thr Ile Asp Glu Ala Gln Val Leu His Gly Leu Asp Gly
        450                 455                 460

Gln Leu Ala Lys Phe Lys Met Pro Lys Lys Val Ile Phe Val Asp Asp
465                 470                 475                 480

Leu Pro Arg Asn Thr Met Gly Lys Val Gln Lys Asn Val Leu Arg Glu
                485                 490                 495

Thr Tyr Lys Asp Ile Tyr Lys
            500
```

BIOSYNTHETIC PLATFORM FOR THE PRODUCTION OF CANNABINOIDS AND OTHER PRENYLATED COMPOUNDS

CROSS REFERENCE TO RELATED APPLICATIONS

This application claims priority under 35 U.S.C. § 371 to International Application No. PCT/US2019/044752, filed Aug. 1, 2019, which application claims priority to U.S. Provisional Application Ser. No. 62/713,348, filed Aug. 1, 2018, the disclosures of which are incorporated herein by reference in their entirety.

STATEMENT REGARDING FEDERALLY SPONSORED RESEARCH

This invention was made with government support under Grant Number DE-FC02-02ER63421, awarded by the U.S. Department of Energy, and Grant Number GM008496, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 1, 2019, is named Sequence ST25.txt and is 287,021 bytes in size.

TECHNICAL FIELD

Provided are methods of producing cannabinoids and other prenylated chemicals and compounds by contacting a suitable substrate with a metabolically-modified microorganism or enzymatic preparations of the disclosure.

BACKGROUND

Prenylation of natural compounds adds structural diversity, alters biological activity, and enhances therapeutic potential. Prenylated compounds often have low natural abundance or are difficult to isolate. Some prenylated natural products include a large class of bioactive molecules with demonstrated medicinal properties. Examples include prenyl-flavanoids, prenyl-stilbenoids, and cannabinoids Cannabinoids are a large class of bioactive plant derived natural products that regulate the cannabinoid receptors (CB1 and CB2) of the human endocannabinoid system. Cannabinoids are promising pharmacological agents with over 100 ongoing clinical trials investigating their therapeutic benefits as antiemetics, anticonvulsants, analgesics and antidepressants. Further, three cannabinoid therapies have been FDA approved to treat chemotherapy induced nausea, MS spasticity and seizures associated with severe epilepsy.

Despite their therapeutic potential, the production of pharmaceutical grade (>99%) cannabinoids still face major technical challenges. Cannibis plants like marijuana and hemp produce high levels of tetrahydrocannabinolic (THCA) and cannibidiolic acid (CBDA), along with a variety of lower abundance cannabinoids. However, even highly expressed cannabinoids like CBDA and THCA, are challenging to isolate due to the high structural similarity of contaminating cannabinoids and the variability of cannabinoid composition with each crop. These problems are magnified when attempting to isolate rare cannabinoids. Moreover, current *cannabis* farming practices present serious environmental challenges. Consequently, there is considerable interest in developing alternative methods for the production of cannabinoids and cannabinoid analogs.

SUMMARY

The disclosure provides a recombinant polypeptide comprising a sequence selected from the group consisting of: (a) SEQ ID NO:30 and having at least a Y288X mutation, wherein X is A, N, S, V or a non-natural amino acid; (b) SEQ ID NO:30 having at least a Y288X mutation, wherein X is A, N, S, V or a non-natural amino acid and at least one other mutation selected from $V49Z_1$, $F213Z_2$, A232S, I234T, $V271Z_3$ and/or G286S, wherein $Z_1$ S, N, T or G, $Z_2$ is H, N or G and $Z_3$ is N or H; (c) any of the mutations combination set forth in Table 1; (d) any of (a), (b) or (c) comprising from 1-20 conservative amino acid substitutions and having NphB prenyltransferase activity; (e) a sequence that is at least 85%, 90%, 95%, 98% or 99% identical to SEQ ID NO:30 and which has at least the mutations recited in (a), (b) or (c), (f) a sequence recited in SEQ ID NOs:1-28 or 29 beginning at amino acid 21; and (g) any sequence that is at least 99% identical to any of SEQ ID NOs: 1-28 or 29, wherein the polypeptide of any of (a)-(g) perform prenylation reactions. In one embodiment, the prenylation reaction comprises the production of CBGA from GPP and Olivetolate or CBGVA from GPP and divarinic acid or CBGXA from a 2,4-dihydroxy benzoic acid or derivative thereof with a chemical group at the C6 position (see, e.g., Formula I).

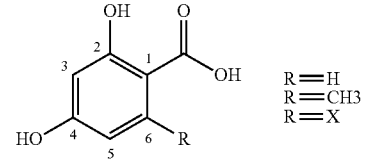

2,4-dihydroxy benzoic acid derivative (XA)

Formula I

Where 'X' can be a halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted ($C_1$-$C_{10}$)alkyl, an optionally substituted ($C_2$-$C_{10}$)alkenyl, an optionally substituted ($C_2$-$C_{10}$)alkynyl, an optionally substituted ($C_1$-$C_{10}$)hetero-alkyl, an optionally substituted ($C_2$-$C_{10}$)hetero-alkenyl, an optionally substituted ($C_2$-$C_{10}$)hetero-alkynyl, an optionally substituted ($C_3$-$C_{10}$)cycloalkyl, an optionally substituted aryl, and an optionally substituted heterocycle. In one embodiment, X is a substituted or unsubstituted alkyl containing 2 to 10 carbons.

The disclosure also provides a recombinant pathway comprising a polypeptide having a sequence a sequence selected from the group consisting of: (a) SEQ ID NO:30 and having at least a Y288X mutation, wherein X is A, N, S, V or a non-natural amino acid; (b) SEQ ID NO:30 having at least a Y288X mutation, wherein X is A, N, S, V, or a non-natural amino acid and at least one other mutation selected from $V49Z_1$, $F213Z_2$, A232S, I234T, $V271Z_3$ and/or G286S, wherein $Z_1$ S, N, T or G, $Z_2$ is H, N or G and $Z_3$ is N or H; (c) any of the mutations combination set forth in Table 1; (d) any of (i), (ii) or (iii) comprising from 1-20 conservative amino acid substitutions and having NphB activity; (e) a sequence that is at least 85%, 90%, 95%, 98% or 99% identical to SEQ ID NO:30 and which has at least the mutations recited in (i), (ii) or (iii); (f) a sequence recited in SEQ ID NOs:1-28 or 29 beginning at amino acid 21; (g) any sequence that is at least 99% identical to any of SEQ ID NOs: 1-28 or 29, and a plurality of enzymes that convert glucose to Geranylpyrophosphate; and (h) any sequence that is at least 99% identical to any of SEQ ID NOs:1-28 or 29 and a plurality of enzymes that convert (iso)prenol to geranylpyrophosphate. In another embodiment, the method further comprises a pyruvate dehydrogenase bypass enzymatic pathway comprising a pyruvate oxidase and an acetyl phosphate transferase. In another or further embodiment, the pathway comprises a "purge valve" that recycles NADH/NAD and NADPH/NADP. In another or further embodiment of any of the foregoing, the pathway comprises the following enzymes: (i) hexokinase (Hex); (ii) Glucose-6-phosphate isomerase (Pgi); (iii) Phosphofructokinase (Pfk); (iv) Fructose-1,6-bisphosphate aldolase (Fba); (v) Triose phosphate isomerase (Tpi); (vi) Gald-3-P dehydrogenase (Gap); (vii) a mutant Gald-3-P dehydrogenase (mGap); (viii) NADH Oxidase (Nox); (ix) Phosphoglycerate Kinase (Pgk); (x) Phosphoglycerate Mutase (2,3 BPG dependent) (dPgm); (xi) Enolase (eno); (xii) Pyruvate Kinase (FBP dependent); (xiii) Pyruvate Oxidase (PyOx); (xiv) Acetyl-phosphate transferase (PTA); (xv) Acetyl-CoA acetyltransferase (PhaA); (xvi) HMG-CoA Synthase (HMGS); (xvii) HMG-CoA Reductase (HMGR); (xviii) Mevalonate Kinase (MVK); (xix) Phosphomevalonate Kinase (PMVK); (xx) Diphosphomevalonate decarboxylase (MDC); (xxi) isopentenyl diphosphate isomerase (IDI); (xxii) geranyl-PP synthase (GPPS); and; (xxiii) a mutant aromatic prenyltransferase. In yet a further embodiment of any of the foregoing embodiments, the pathway comprises the enzymes (i) to (xviii) and (xxii) to (xxiii) above in addition to phosphomevalonate decarboxylase (PMDC) and isopentenyl-phosphate kinase (IPK). In yet another or further embodiment, the pathway comprises a 4-step pathway to convert isoprenol or prenol to GPP using ATP and one or more steps to recycle ADP/ATP. In another or further embodiment of any of the foregoing, the pathway comprises (a) (iso)prenol kinase (PRK); (b) isopentenyl phosphate kinase (IPK); (c) isopentenyl diphosphate isomerase (IDI); and (d) geranyl pyrophosphate synthase (GPPS). In still another or further embodiment, the pathway is supplemented with ATP and olivetolate (or 2,4-dihydroxy benzoic acid or derivative thereof) and the pathway produces a cannabinoid precursor. In a further embodiment, the pathway further comprises a cannabidiolic acid synthase. In still another or further embodiment, the pathway produces cannabidiolic acid.

The disclosure also provides a method of producing a prenylated compound comprising contacting a substrate with a prenyl-group having the general structure:

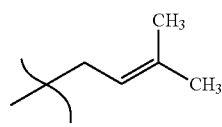

in the presence of a recombinant polypeptide having a sequence selected from the group consisting of: (a) SEQ ID NO:30 and having at least a Y288X mutation, wherein X is A, N, S, V or a non-natural amino acid; (b) SEQ ID NO:30 having at least a Y288X mutation, wherein X is A, N, S, V or a non-natural amino acid, and at least one other mutation selected from V49$Z_1$, F213$Z_2$, A232S, I234T, V271$Z_3$ and/or G286S, wherein $Z_1$ S, N, T or G, $Z_2$ is H, N or G and $Z_3$ is N or H; (c) any of the mutations combination set forth in Table 1; (d) any of (i), (ii) or (iii) comprising from 1-20 conservative amino acid substitutions and having NphB activity; (e) a sequence that is at least 85%, 90%, 95%, 98% or 99% identical to SEQ ID NO:30 and which has at least the mutations recited in (i), (ii) or (iii); (f) a sequence recited in SEQ ID NOs:1-28 or 29 beginning at amino acid 21; and (g) any sequence that is at least 99% identical to any of SEQ ID NOs: 1-28 or 29, wherein the prenyl group is added to the substrate.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

DETAILED DESCRIPTION

Figure 1A:
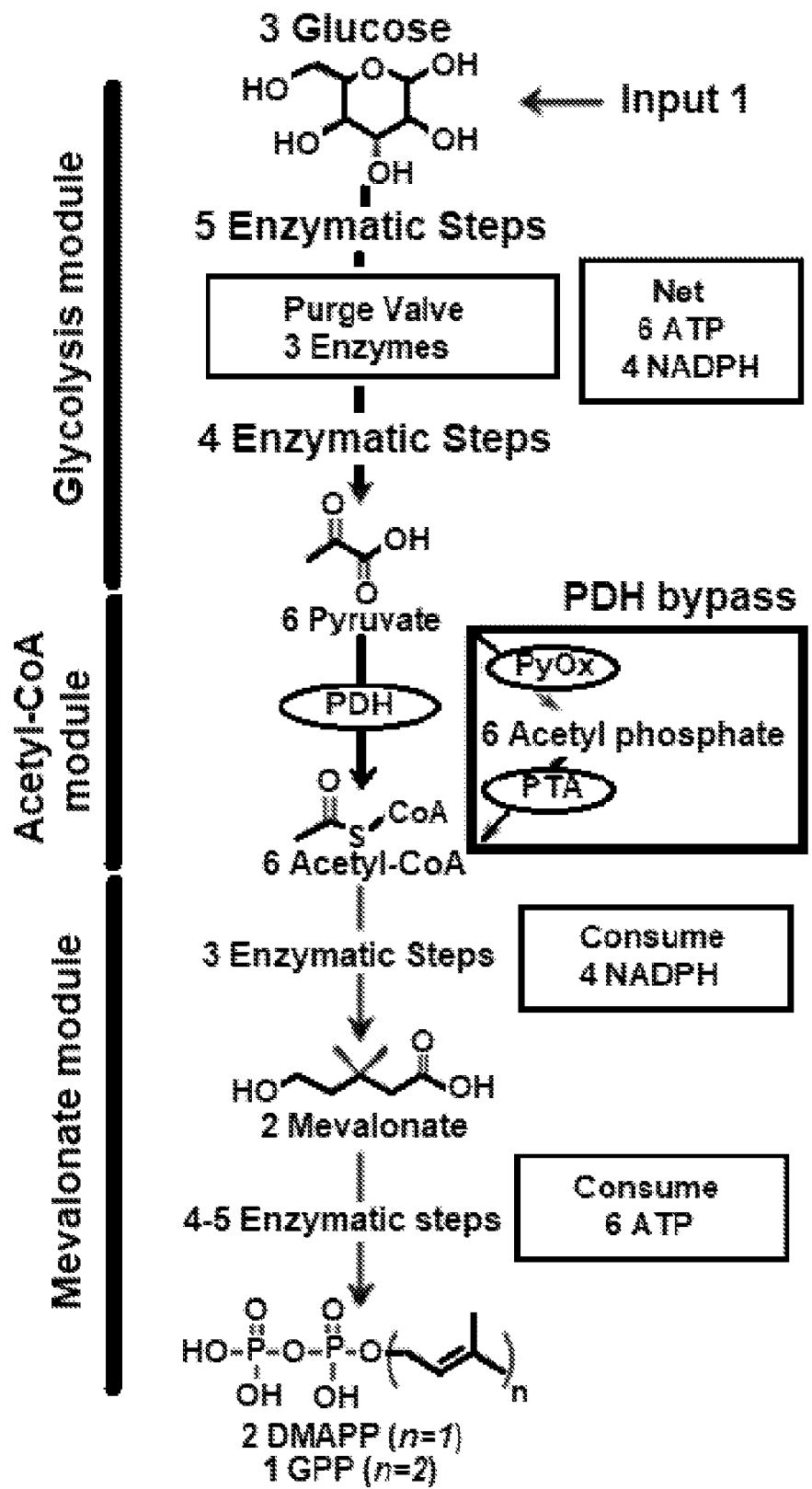
FIG. 1A-B depicts exemplary biosynthetic pathways of the disclosure. (A) The synthetic biochemistry platform for the production of prenylnatural products. First, glucose is broken down into pyruvate through a glycolysis pathway modified to regulate NADPH levels (12 enzymatic steps). Then, either PDH or the PDH bypass converts pyruvate into acetyl-CoA. Acetyl-CoA is converted into GPP via the mevalonate pathway (eight enzymatic steps). By varying the aromatic prenyltransferase (aPT) and aromatic substrate various prenyl-flavonoids and prenyl-stilbenoids using the same central pathway can be produced. Variants of the prenyltransferase NphB (dNphB) were developed to produce CBGA or CBGVA. CBGA is converted to cannabidiolic acid (CBDA) and CBGVA is converted to cannabidivaric acid (CBDVA) via cannabidiolic acid synthase (CBDAS). It is possible to produce other cannabinoids by using different cannabinoid synthases (THCAS and CBCAS). (B) Depicts a more detailed view of the pathway of (A). Glucose is broken down into pyruvate through glycolysis (dark blue). The purge valve outlined in dark blue allows carbon flux to continue through the glycolysis pathway without building up excess NADPH. Pyruvate is converted to acetyl-CoA through the PDH bypass outlined in light blue. Acetyl-CoA is built up into high energy phosphate molecules through the mevalonate pathway (aqua) to produce GPP. Then, the GPP from the mevalonate pathway is used to prenylate an aromatic polyketide. Shown here is the prenylation of olivetolate to produce CBGA; however, olivetolate could be replaced with a wide range of substrates (aromatic and non-aromatic) to generate various prenylated products. Finally, CBGA is converted to CBDA with CBDAS. A spontaneous decarboxylation completes the biosynthetic pathway to CBDA. The production of CBDA completes the cannabinoid module shown in green.

As used herein and in the appended claims, the singular forms "a," "an," and "the" include plural referents unless the context clearly dictates otherwise. Thus, for example, reference to "a polynucleotide" includes a plurality of such polynucleotides and reference to "the enzyme" includes reference to one or more enzymes, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

Prenylation (also known as isoprenylation or lipidation) is the addition of hydrophobic molecules to a protein or chemical compound. It is usually assumed that prenyl groups (3-methylbut-2-en-1-yl) facilitate attachment to cell membranes, similar to lipid anchors like the GPI anchor. Prenyl groups have been shown to be important for protein-protein binding through specialized prenyl-binding domains.

Prenylated natural products are a large class of bioactive molecules with demonstrated medicinal properties. Examples include prenyl-flavanoids, prenyl-stilbenoids, and cannabinoids. Plant-derived prenylcompounds are difficult to isolate due to the structural similarity of contaminating molecules, and the variable composition between crops. These challenges are further exacerbated when attempting to isolate low abundance compounds. Many chemical syntheses have been developed to address the challenges associated with making prenylated natural products, but they are generally impractical for drug manufacturing due to the degree of complexity and low yields.

Microbial production is a useful alternative to natural extraction for prenylated natural products, but comes with many challenges such as the need to divert carbon flux from central metabolism and product toxicity to name a few. For example, prenyl-natural products like prenyl-naringenin, prenyl-resveratrol, and cannabidiolic acid (CBDA) are derived from a combination of the metabolic pathways for fatty acid, isoprenoid, and polyketide biosynthesis. So, high-level production requires efficient rerouting of long, essential and highly regulated pathways. Despite the challenges, many groups have engineered microbes to produce unprenylated polyketides, like naringenin, resveratrol, and olivetolate, but at relatively low levels (110, 391, and 80 mg/L, respectively). Obtaining prenylated products is even more challenging because geranyl-pyrophosphate (GPP) is an essential metabolite that is toxic to cells at moderate concentrations, creating a significant barrier for high-level microbial production.

Cannabinoids in particular show immense therapeutic potential with over 100 ongoing clinical trials as antiemetics, anticonvulsants, antidepressants, and analgesics. Nevertheless, despite the therapeutic potential of prenyl-natural products, their study and use is limited by the lack of cost-effective production methods.

The two main alternatives to plant-based cannabinoid production are organic synthesis and production in a metabolically engineered host (e.g., plant, yeast, or bacteria). Total syntheses have been elucidated for the production of some cannabinoids, such as THCA and CBDA, but they are often not practical for drug manufacturing. Additionally, the synthetic approach is not modular, requiring a unique synthesis for each cannabinoid. A modular approach could be achieved by using the natural biosynthetic pathway.

The three major cannabinoids (THCA, CBDA and cannibichromene or CBCA) are derived from a single precursor, CBGA. Additionally, three low abundance cannabinoids are derived from CBGVA (FIG. 1A). Thus, the ability to make CBGA and CBGVA in a heterologous host would open the door to the production of an array of cannabinoids. Unfortunately, engineering microorganisms to produce CBGA and CBGVA has proven extremely challenging.

Cannabinoids are derived from a combination of fatty acid, polyketide, and terpene biosynthetic pathways that generate the key building blocks geranyl pyrophosphate (GPP) and olivetolic acid (OA) (FIG. 1A). High level CBGA biosynthesis requires the re-routing of long, essential and highly regulated pathways. Moreover, GPP is toxic to cells, creating a notable barrier to high level production in microbes. While Gagne et al. (Proc. Natl. Acad. Sci., 109: 12811, 2012) engineered a pathway to produce OA in yeast, the titers were very low (0.5 mg $L^{-1}$), suggesting that high level production of intermediates on the pathway is not straightforward. In a separate study, Zirpel et al. produced THCA in a yeast lysate containing the promiscuous prenyltransferase (NphB) and THCA synthase, supplemented with GPP and olivetolic acid (OA) (J. Biotechnol., 259:204-212, 2017). Yet, there are still no published reports of cannabinoid production in engineered live cells from low cost feedstocks.

Synthetic biochemistry, in which complex biochemical conversions are performed cell-free using a mixture of enzymes, affords potential advantages over traditional metabolic engineering including: a higher level of flexibility in pathway design; greater control over component optimization; more rapid design-build-test cycles; and freedom from cell toxicity of intermediates or products. The disclosure provides a cell-free system for the production of cannabinoids.

This disclosure provides enzyme variants and pathways comprising such variants for the prenylation of compounds including the production of cannabinoids. In addition, the biosynthetic pathways described herein use "purge valves" to regulate NAD(P)H levels. Such "purge valves" have demonstrated high level production of monoterpenes from glucose indicating that significant GPP can be produced cell-free (see, International Pat. Publ. WO2017/015429, the disclosure of which is incorporated herein by reference). These purge valves were used to upgrade and diversify the original system to produce complex natural products like cannabinoids. A synthetic biochemistry approach is outlined in FIGS. 1A, 1B, 5A and 5B. In one embodiment, the disclosure provides a cell-free system for prenylation using GPP derived from glucose (see, FIGS. 1A, 1B, 5A, 5B and 7). In another embodiment, the disclosure provides a cell-free system for prenylation using GPP derived from (iso) prenol or prenol (see, FIG. 6). The pathway of FIG. 6 can be coupled to any ATP generating system to produce the ATP needed for a reaction. For example, the pathway can be coupled with a creatine kinase ATP generating system; an acetate kinase system; a glycolysis system as well as others. Enzymes (nucleic acid coding sequences and polypeptides) of FIG. 6 are provided in SEQ ID NOs: 54-65 (e.g., PRK enzymes are provided in SEQ ID NOs: 54-57; IPK enzymes are provided in SEQ ID NOs: 58-61; IDI enzymes are provided in SEQ ID NOs:62-63; and FPPS enzymes are provided in SEQ ID NOs: 64-65).

NphB is an aromatic prenyltransferase that catalyzes the attachment of a 10-carbon geranyl group to aromatic substrates. NphB exhibits a rich substrate selectivity and product regioselectivity. NphB, identified from *Streptomyces*, catalyzes the addition of a 10-carbon geranyl group to a number of small organic aromatic substrates. NphB has a spacious and solvent accessible binding pocket in to which two substrates molecules, geranyl diphosphate (GPP) and 1,6-dihydroxynaphthalene (1,6-DHN), can be bound. GPP is stabilized via interactions between its negatively charged diphosphate moiety and several amino acid sidechains, including Lys119, Thr171, Arg228, Tyr216 and Lys284, in addition to $Mg^{2+}$. A $Mg^{2+}$ cofactor is required for the activity of NphB. NphB from *Streptomyces* has a sequence as set forth in SEQ ID NO:30.

NovQ (accession no. AAF67510, incorporated herein by reference) is a member of the CloQ/NphB class of prenyltransferases. The novQ gene can be cloned from *Streptomyces niveus*, which produces an aminocoumarin antibiotic, novobiocin. Recombinant NovQ can be expressed in *Escherichia coli* and purified to homogeneity. The purified enzyme is a soluble monomeric 40-kDa protein that catalyzed the transfer of a dimethylallyl group to 4-hydroxyphenylpyruvate (4-HPP) independently of divalent cations to yield 3-dimethylallyl-4-HPP, an intermediate of novobiocin. In addition to the prenylation of 4-HPP, NovQ catalyzed carbon-carbon-based and carbon-oxygen-based prenylations of a diverse collection of phenylpropanoids, flavonoids and dihydroxynaphthalenes. Despite its catalytic promiscuity, the NovQ-catalyzed prenylation occurred in a regiospecific manner. NovQ is the first reported prenyltransferase capable of catalyzing the transfer of a dimethylallyl group to both phenylpropanoids, such as p-coumaric acid and caffeic acid, and the B-ring of flavonoids. NovQ can serve as a useful biocatalyst for the synthesis of prenylated phenylpropanoids and prenylated flavonoids.

*Aspergillus terreus* aromatic prenyltransferase (AtaPT; accession no. AMB20850, incorporated herein by reference), which has recently been discovered and characterized, is responsible for the prenylation of various aromatic compounds. Recombinant AtaPT can be overexpressed in *Escherichia coli* and purified. *Aspergillus terreus* aromatic prenyltransferase (AtaPT) catalyzes predominantly C-monoprenylation of acylphloroglucinols in the presence of different prenyl diphosphates.

Figure 2A:
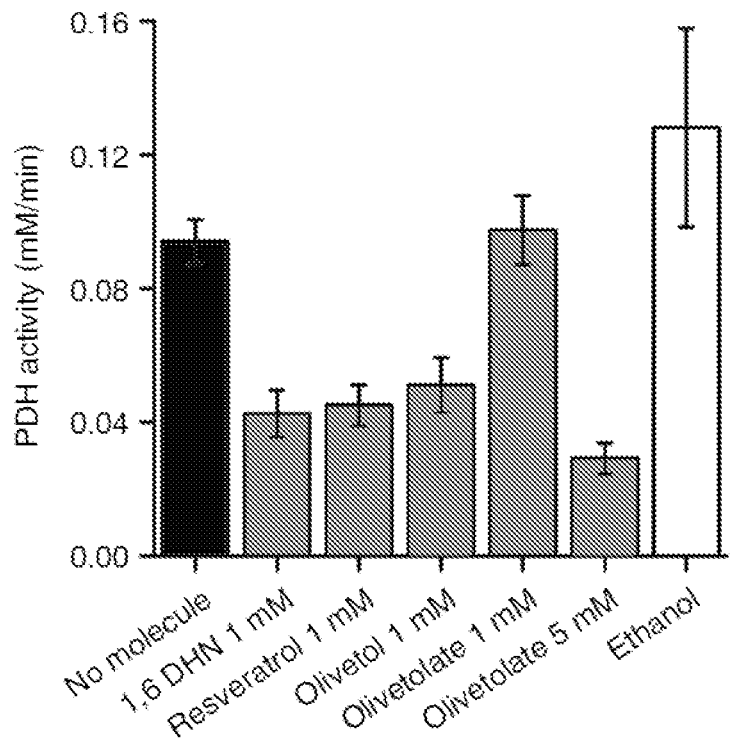
FIG. 2A-D shows development of PDH bypass for the prenylation of aromatic polyketides. (A) The activity of pyruvate dehydrogenase (Ec PDH) was measured in the presence of various aromatic polyketides and 2% ethanol (vehicle) (n=3). (B) A comparison of the final titers achieved with the full pathway utilizing PDH (PDH system—gray trace) and the PDH bypass system (blue trace) at different concentrations of 1,6 DHN. Error bars represent the standard deviation between samples (n=3). (C) The amount of 5-prenyl-1,6-DHN blue trace and CBGA green trace produced over time with the PDH bypass system using WT NphB. The error bars represent the standard deviation between samples (n=3). (D) Various aromatic substrates were added to the pathway with either NphB, AtaPT, or NovQ prenyltransferase (biological replicates, n=3). The result is a variety of C5 and C10 prenyl-natural products. (* Indicates titer not determined).
Figure 2B:
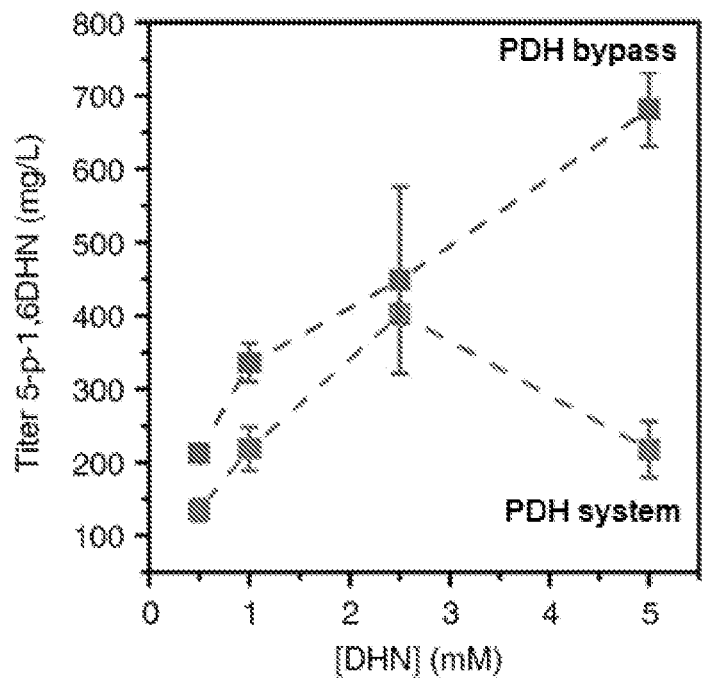
Figure 2C:
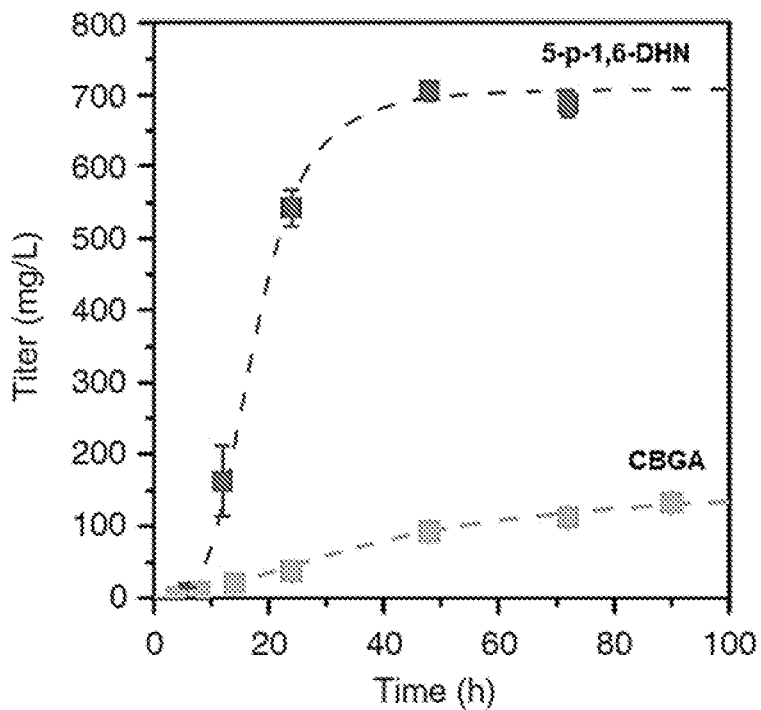
Figure 2D:
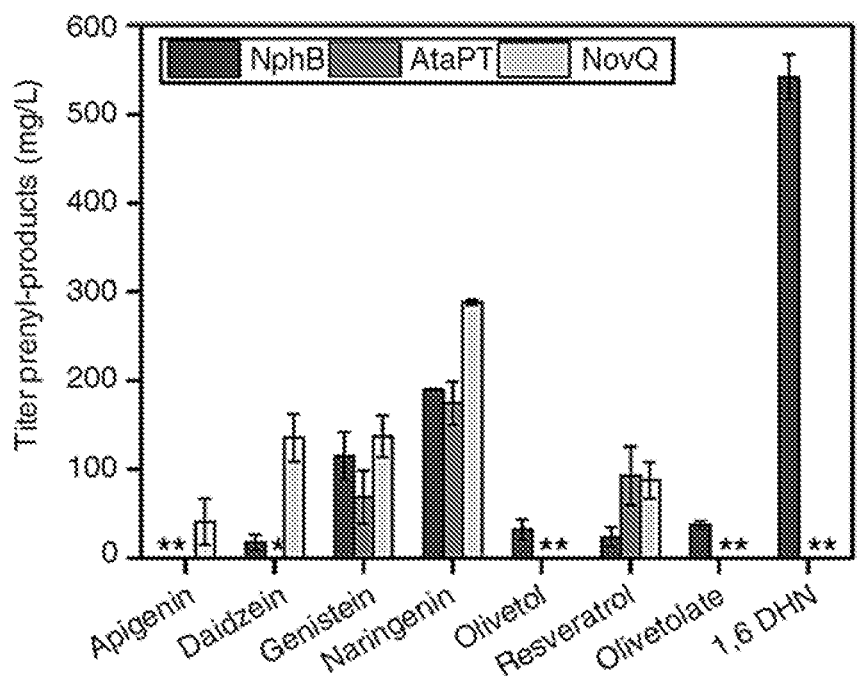

Olivetolic acid (OA) is a relatively poor substrate for wild-type NphB. As a result, the ability of the cell-free system to prenylate a co-substrate was tested by using a more preferred NphB substrate, 1,6 dihydroxynapthalene (1,6 DHN). About 400 mg/L (1.3 mM) of prenylated product was obtained when starting with 2.5 mM 1,6 DHN and 500 mM glucose. However, when the starting 1,6 DHN concentration was increased from 2.5 to 5 mM, final titers decreased 2-fold suggesting that 1,6 DHN was inhibiting one or more enzymes. Enzyme assays revealed that *E. coli* pyruvate dehydrogenase (EcPDH) was inhibited by not only 1,6 DHN, but several other aromatic polyketides (FIG. 2B). At 1 mM of either 1,6 DHN, olivetol, or resveratrol the activity of PDH decreased 2-fold (FIG. 2B). Thus, experiments were designed to eliminate PDH by implementing a PDH bypass (see FIGS. 1A and 2B). In the PDH bypass, pyruvate was converted to acetyl-CoA using pyruvate oxidase (PyOx) and acetyl-phosphate transferase (PTA) thereby eliminating PDH (FIG. 1A). As shown in FIG. 2A the new system removed the inhibition seen at higher concentrations of 1,6 DHN and increased titers of 5-prenyl-1,6 DHN 4-fold over the PDH system when starting at 5 mM 1,6 DHN (FIG. 2B). FIG. 2C shows a time course of 5-prenyl-1,6 DHN biosynthesis starting with 5 mM 1,6 DHN utilizing the PDH bypass. Approximately 50% of the 1,6 DHN was converted in the first 24 hours, ultimately reaching a final titer of 705±12 mg/L.

Figure 3A:
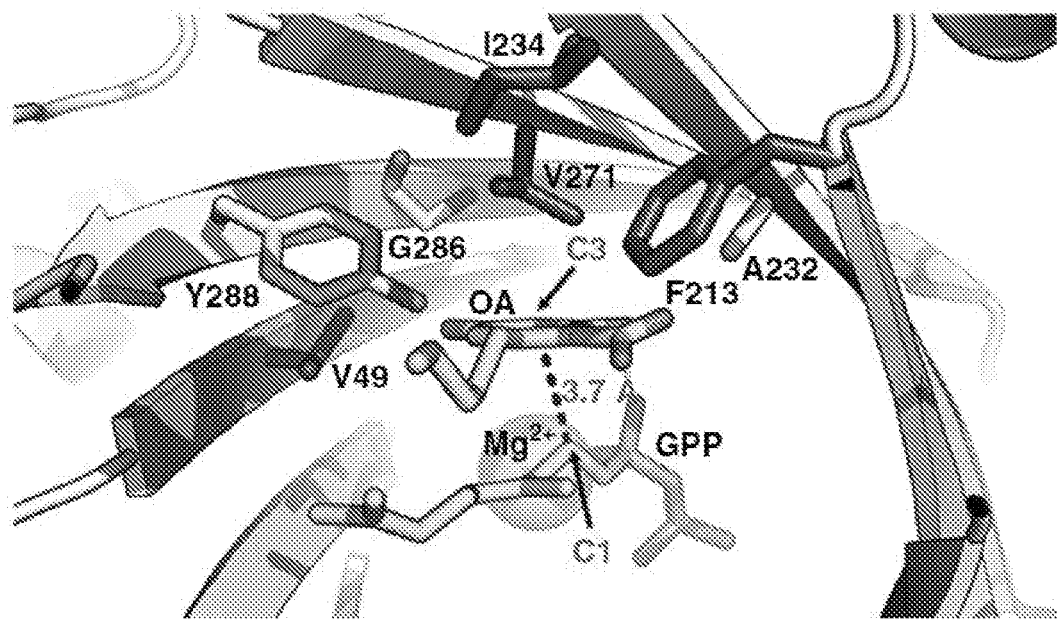
FIG. 3A-C shows the engineering of NphB to improve CBGA production. (A) A model of olivetolate in the active site of WT NphB. Residues A288, G286 and A232 and I234, V271 and V49 were allowed to vary during the design process. Residues A288, G286 and A232 had the largest effects on activity with OA and were the positions targeted in the focused library. (B) The results of an activity assay to determine the approximate activity of NphB mutants with olivetolate as the substrate. The fold-improvement is an average of triplicate reactions with GPP (2.5 mM) olivetolate (5 mM), $MgCl_2$ (5 mM) and 1 mg/mL of WT NphB and mutants. (C) GC-MS chromatograms of the full pathway reaction products using of M23 and WT NphB compared to a CBGA standard. The M23 mutant dramatically improves specificity for the correct product.

The prenylation of aromatic polyketides by NphB is thought to proceed through a carbocation intermediate in which the first step is dissociation of diphosphate from GPP to create a carbocation on the C1 carbon of GPP, which subsequently attacks a nearby nucleophile. To improve the regiospecificity of prenyl-transfer, OA was modeled into the active site of NphB using the crystal structure of NphB in complex with 1,6 DHN, $Mg^{2+}$ and a nonhydrolyzable analog of GPP (geranyl S-thiolodiphosphate) as a starting point (PDBID 1ZB6; Protein Data Bank reference 1ZB6). For the design, OA was placed into the binding pocket using 1,6 DHN as a guide, situating the desired prenylation site, the C3 carbon of OA, 3.7 Å above the nascent geranyl C1 carbocation (FIG. 3A). The distance chosen was based on the distance of the C5 carbon of 1,6 DHN to the C1 carbon of GPP. Residues in contact with OA were then varied using ROSETTA software to optimize the active site of NphB for binding OA. Side chains in contact with GPP or that potentially provide catalytic function were left fixed. The result was an ensemble of suggested NphB variants.

To reduce the number of variants to test experimentally, changes likely to have the most significant impact on OA binding were ranked using a scoring system. A representative group of variants were picked (Table 1) and each residue was systematically changed back to the wild-type side chain in the background of the other mutations, and the change evaluated in the energy score (Table 2). Y288 replacements had the largest impact on the energy score so Y288A or the Y288N mutation were used in every construct evaluated experimentally. The frequency of mutation, how multiple mutations might work in concert, and the computational energy score to further shape the NphB library were all considered. With these considerations, a library comprised of 29 constructs ranging from a single point mutant to up to 6 mutations per construct was generated as set forth in Table 1 (see also SEQ ID NOs: 1-29; note SEQ ID NOs: 1-29 include a hexahistidine leader from the expression construct, i.e., amino acids 1-20, which are not necessary for biological activity).

TABLE 1 provides exemplary mutations and the fold improvement relative to wild type (i.e., a polypeptide of SEQ ID NO: 30). NphB library constructs and mutations (amino acid positions referenced to SEQ ID NO: 30).

| NphB Construct | Mutations | Fold Improvement over WT |
|---|---|---|
| M1 | Y288A | 26 |
| M2 | Y288N | 11 |
| M3 | Y288A, F213H | 12 |
| M4 | Y288A, F213N | 2 |
| M5 | Y288N, V49S | 5 |

TABLE 1-continued provides exemplary mutations and the fold improvement relative to wild type (i.e., a polypeptide of SEQ ID NO: 30). NphB library constructs and mutations (amino acid positions referenced to SEQ ID NO: 30).

| NphB Construct | Mutations | Fold Improvement over WT |
|---|---|---|
| M6 | Y288S, V49N | 11 |
| M7 | Y288A, V49S | 9 |
| M8 | Y288N, V49T | 1 |
| M9 | Y288N, I234T | 1 |
| M10 | Y288N, G286S | 150 |
| M11 | Y288N, F213N, V49G | 3 |
| M12 | Y288A, F213N, I234T | 3 |
| M13 | Y288S, F213N, V49N | 2 |
| M14 | Y288N, F213G, I234T | 1 |
| M15 | Y288A, F213N, A232S | 17 |
| M16 | Y288N, F213N, A232S | 2 |
| M17 | Y288N, F213G, V49T | 2 |
| M18 | Y288N, V49S, V271N | 1 |
| M19 | Y288N, F213N, V49S, V271N | 2 |
| M20 | Y288N, F213G, V49T, V271H | 4 |
| M21 | Y288N, F213N, V49S, I234T, A232S, V271N | 0.5 |
| M22 | Y288N, F213G, V49T, I234T, V271H, L298I | 0.5 |
| M23* | Y288A, G286S | 185 |
| M24* | Y288A, G286S, A232S | 150 |
| M25* | Y288A, G286S, A232S, F213H | 110 |
| M27* | Y288V, G286S | 155 |
| M28* | Y288V, G286S, A232S | 1.5 |
| M30* | Y288A, A232S | 175 |
| M31* | Y288V, A232S | 180 |
| M32b | V49I | ND |
| M33b | M162C | ND |
| M34b | M162R | ND |
| M35b | A232N | ND |
| M36b | V271S | ND |
| M37b | V271A | ND |
| M38b | Y288D | ND |
| M39b | Y288H | ND |
| M40b | L298R | ND |
| M41b | L298A | ND |
| M42b | L298G | ND |
| M43b | L298V | ND |
| M44b | L298N | ND |

*Second round focused library
[b]Mutation predicted by Rosetta, but not tested
ND—Not determined

TABLE 2

Kinetic parameters for NphB mutants

| Construct | $k_{cat}$ (min$^{-1}$) | $K_M$ (mM) | $k_{cat}/K_M$ (min$^{-1}$ mM$^{-1}$) |
|---|---|---|---|
| WT NphB | 0.0021 ± 0.00008 | 0.64 ± 0.08 | 0.0033 ± 0.0005 |
|  | 0.0047 ± 0.0003[b] | 0.88 ± 0.2[b] | 0.005 ± 0.001[b] |
| NphB M1 | 0.061 ± 0.003 | 0.58 ± 0.11 | 0.11 ± 0.02 |
| NphB M10 | 0.79 ± 0.02 | 0.34 ± 0.02 | 2.4 ± 0.2 |
| NphB M23 | 1.58 ± 0.05 | 0.45 ± 0.05 | 3.5 ± 0.4 |
|  | 0.48 ± 0.07[b] | 2.4 ± 0.6[b] | 0.2 ± 0.06[b] |
| NphB M30 | 1.07 ± 0.05 | 0.25 ± 0.05 | 4.2 ± 0.9 |
| NphB M31 | 1.30 ± 0.05 | 0.12 ± 0.02* | 10.8 ± 2.1 |
|  | 6.0 ± 0.8[b] | 1.8 ± 0.5[b] | 3.3 ± 1[b] |

[b]Kinetic parameters for divarinic acid

Recombinant methods for producing and isolating modified NphB polypeptides of the disclosure are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) J. Am. Chem. Soc. 85: 2149-2154;

each of which is incorporated by reference). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

Figure 3B:
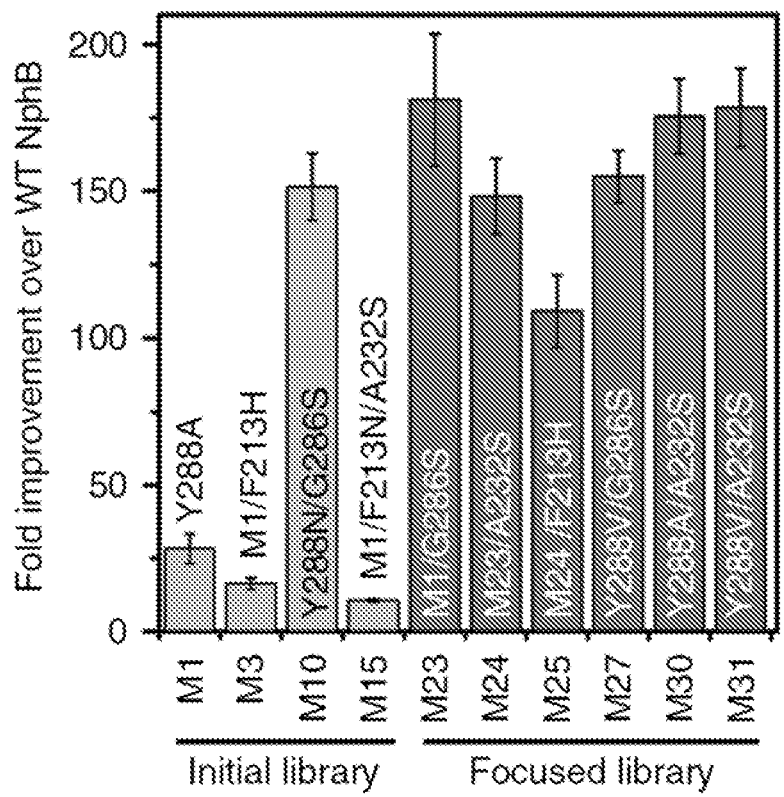

Crudely purified NphB mutants were obtained and an initial screen was performed for CBGA production using GPP and OA at concentrations that were saturating for wild-type NphB. Six constructs were identified that had >10-fold apparent increase in activity (M1, M2, M3, M6, M10 and M15) and 4 constructs that had 2-10-fold apparent improvement (M5, M7, M12 and M20) when compared to WT NphB, while the remaining constructs had similar activity to WT NphB. The top hits from the initial screen (M1, M3, M10 and M15) were purified and more carefully characterized (FIG. 3B). Several observations were apparent from the initial screen: (1) Y288A (M1) and Y288N (M2) by themselves dramatically enhanced activity, as predicted by computation; (2) the presence of Y288N in any construct decreased the purification yield suggesting Y288N may be a destabilizing mutation making Y288A a more desirable mutation; (3) the addition of G286S in the Y288N (M10) background appeared to improve activity further over Y288N (M2), suggesting that G286S could be another favorable mutation; (4) a slight activity improvement of Y288A/F213N/A232S (M15) over Y288A (M1), even though F213N had a neutral or deleterious effect in the Y288A/F213N (M5) construct suggesting that A232S may also be a favorable mutation.

From these initial observations a focused library was designed that included variants Y288A, GS86S and A232S in various combinations. Other combinations with Y288V were added with the rationale that it may improve stability while still reducing the size of the Y288 side chain. All but one of the constructs in the second library exhibited activity at least 100-fold higher than WT NphB in a one hour endpoint assay. A comparison of the best mutants from round one and the best mutants from round two are shown in FIG. 3B. Clearly, the combination of beneficial mutations from round 1 improved CBGA production. Additionally the Y288A and Y288V constructs improved expression of NphB compared to Y288N without sacrificing activity.

The best two mutants from the initial screen were further characterized as well as the best three constructs from the focused library. The kinetic parameters are summarized in Table 2. While all of the mutants have relatively modest effects on $K_m$, a dramatic improvements in $k_{cat}$ values was observed. M23 (the NphB of SEQ ID NO:23) in particular improved $k_{cat}$ 750-fold from $0.0021\pm0.00008$ min$^{-1}$ to $1.58\pm0.05$ min$^{-1}$. The catalytic efficiency ($k_{cat}/K_m$) for both M23 and M31 were improved over 1000-fold compared to the wild-type enzyme. Although M31 had a higher $k_{cat}/K_m$ than M23, M23 was employed rather than M31 because M23 had a higher $k_{cat}$ and the synthetic biochemistry system generally operates at saturating OA conditions.

Figure 3C:
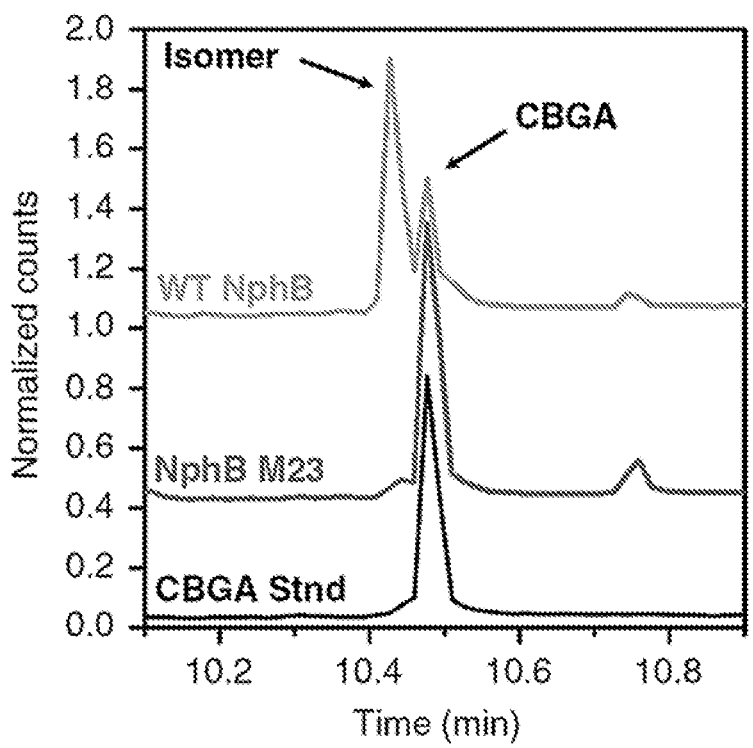

The designed mutant M23 not only shows dramatically improved catalytic efficiency for prenylation of OA, it is also extremely specific, producing only the correct CBGA product. WT NphB produces CBGA, but the dominant product is a prenylated isomer (FIG. 3C). In contrast the designed mutant M23 makes CBGA almost exclusively. Overall, the designed enzyme is a much more effective CBGA synthase than the non-specific prenylating wild-type enzyme.

The disclosure thus provides mutant NphB variants comprising (i) SEQ ID NO:30 and having at least a Y288X mutation, wherein X is A, N, S, V or a non-natural amino acid; (ii) SEQ ID NO:30 having at least a Y288X mutation, wherein X is A, N, S, V or a non-natural amino acid, and at least one other mutation selected from V49$Z_1$, F213$Z_2$, A232S, I234T, V271$Z_3$ and/or G286S, wherein $Z_1$ S, N, T or G, $Z_2$ is H, N or G and $Z_3$ is N or H; (iii) any of the mutations combination set forth in Table 1; (iv) any of (i), (ii) or (iii) comprising from 1-20 (e.g., 2, 5, 10, 15 or 20; or any value between 1 and 20) conservative amino acid substitutions and having NphB activity; (v) a sequence that is at least 85%, 90%, 95%, 98% or 99% identical to SEQ ID NO:1-29 or 30 and which has at least the mutations recited in (i), (ii) or (iii); (vi) an NphB mutation comprising any of the sequence recited in SEQ ID NOs:1-28 or 29 beginning at amino acid 21; or (vii) any sequence that is at least 99% identical to any of SEQ ID NOs: 1-28 or 29 and having NphB activity. By "NphB activity" means the ability of the enzyme to prenylate a substrate and more specifically to generate CBGA from OA.

As used herein a non-natural amino acid refers to amino acids that do not occur in nature such as N-methyl amino acids (e.g., N-methyl L-alanine, N-methyl L-valine etc.) or alpha-methyl amino acids, beta-homo amino acids, homo-amino acids and D-amino acids. In a particular embodiment, a non-natural amino acid useful in the disclosure includes a small hydrophobic non-natural amino acid (e.g., N-methyl L-alanine, N-methyl L-valine etc.).

In addition, the disclosure provides polynucleotides encoding any of the foregoing NphB variants. Due to the degeneracy of the genetic code, the actual coding sequences can vary, while still arriving at the recited polypeptide for NphB mutants and variants. Examplary polynucleotide sequence are provided in SEQ ID NOs: 66, 67 and 68 (corresponding to the polypeptide sequences of SEQ ID NO:23, 29 and 69 respectively). It will again be readily apparent that the degeneracy of the genetic code will allow for wide variation in the percent identity to SEQ ID NOs: 66, 67 and 68, while still encoding a polypeptide of SEQ ID NO:23, 29 and 69.

The disclosure also provide recombinant host cells and cell free systems comprising any of the NphB variant enzymes of the disclosure. In some embodiments, the recombinant cells and cell free systems are used carry out prenylation processes.

One objective of the disclosure is to produce the precursor GPP from glucose or prenol and/or isoprenol, which can then be used to prenylate added OA with a mutant NphB of the disclosure, thereby generating CBGA.

The disclosure thus provides a cell-free system comprising a plurality of enzymatic steps that converts glucose to geranyl pyrophosphate, wherein the pathway includes a purge valve and a PDH bypass enzymatic process.

Figure 1A:
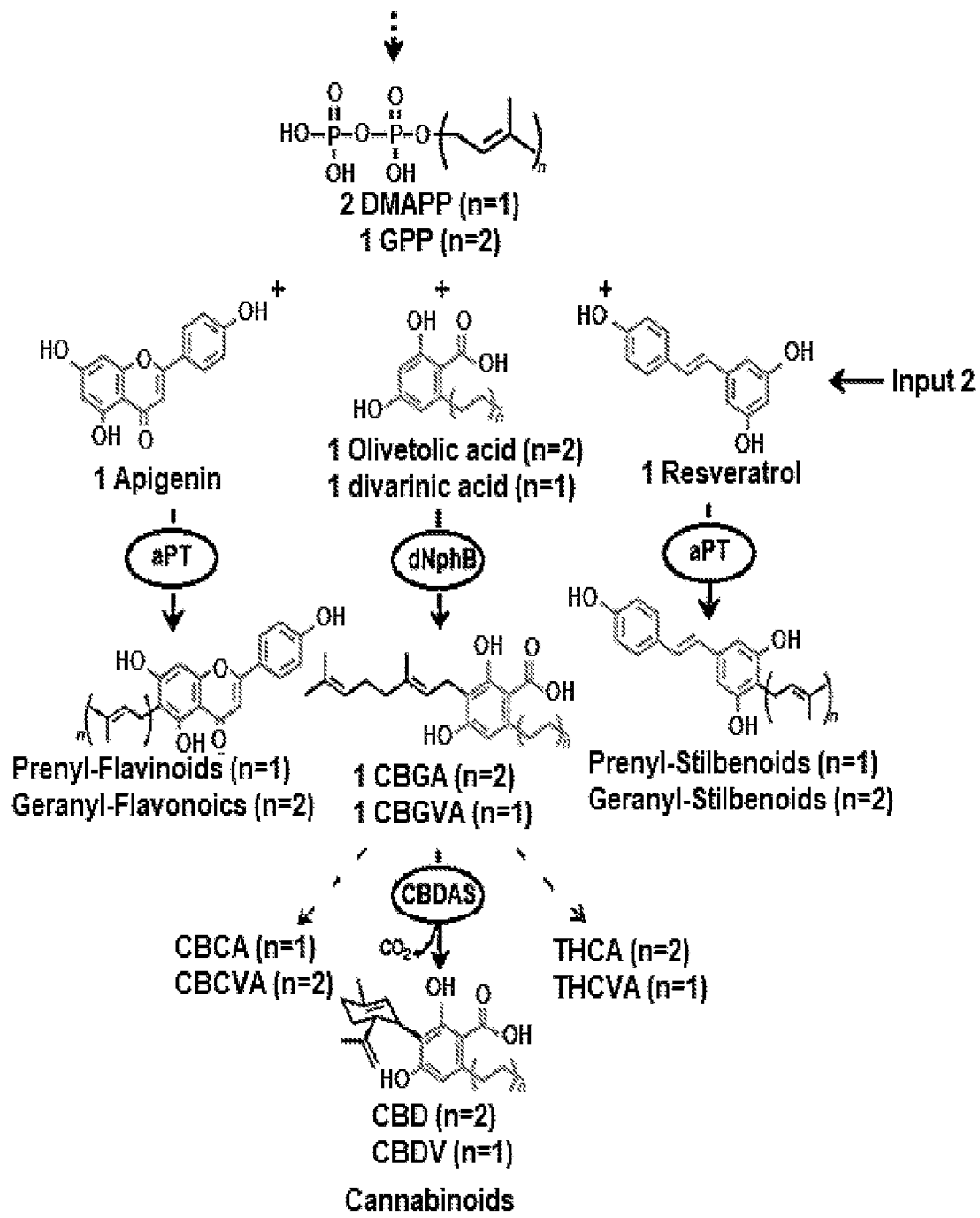
Figure 1B:
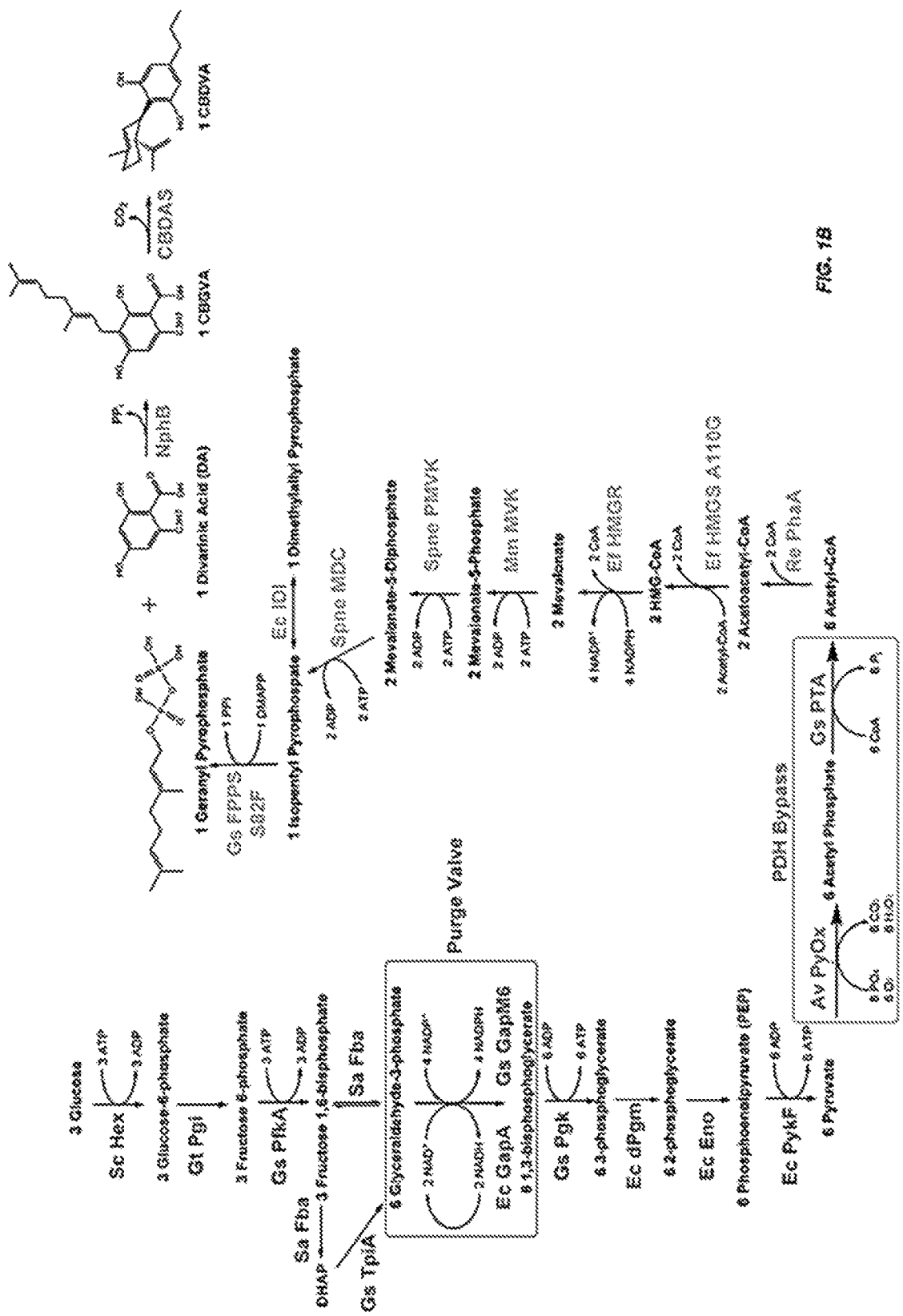

As depicted in FIG. 1B, one pathway of the disclosure comprises converting glucose to glucose-6-phosphate using a hexokinase. A hexokinase (EC 2.7.1.1) is an enzyme that phosphorylates hexoses (six-carbon sugars), forming hexose phosphate. Hexokinase possesses the ability to transfer an inorganic phosphate group from ATP to a substrate. Numerous hexokinase proteins from various organisms have been cloned and expressed. In some embodiments, the hexokinase comprises the sequence set forth in UniProtKB accession number P04806 from *Saccharomyces cerevisiae* (Sc) (incorporated herein by reference) as well as sequences that are at least 60%, 70%, 80%, 85%, 90%, 95%, 98%, 99% identical thereto and have hexokinase activity.

The glucose-6-phosphate is then converted to fructose-6-phosphate by phosphoglucoseisomerase (Pgi) (EC 5.3.1.9). Accordingly, in addition to the foregoing, the terms "phosphoglucoisomerase" or "Pgi" refer to proteins that are capable of catalyzing the formation of fructose-6-phosphate from glucose-6-phosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:31, or at least about 50%, 60%, 70%, 80%, 90%, 95%, 96%, 97%, 98%, 99% or greater sequence similarity, as calculated by NCBI BLAST, using default parameters and wherein the enzyme has phosphoglucoisomerase activity.

In another or further embodiment, a system or recombinant microorganism provided herein includes expression of a phosphofructokinase (Pfk, polyphosphate-dependent Pfk or homolog or variants thereof). This expression may be combined with other enzymes in the metabolic pathway. The Pfk can be derived from *G. stearothermophilus* (SEQ ID NO:32). In another embodiment, an engineered variant of Pfk can be used so long as it has phosphofructokinase activity and can convert fructose-6-phosphate to fructose-1, 6-bisphosphate. Such engineered variants can be obtained by site-directed mutagenesis, directed evolutions and the like. Thus included within the disclosure are polypeptides that are at least 85-99% identical to a sequence as set forth in SEQ ID NO:32 and having phosphofructokinase activity (see, e.g., SEQ ID NOs:33-34).

In addition to the foregoing, the terms "fructose 1,6 bisphosphate aldolase" or "Fba" refer to proteins that are capable of catalyzing the formation of dihydroxyacetone phosphate and glyceraldehyde-3-phosphate from fructose 1,6-bisphosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:35. Additional homologs include: *Synechococcus elongatus* PCC 6301 YP_170823.1 having 26% identity to SEQ ID NO:35; *Vibrio nigripulchritudo* ATCC 27043 ZP_08732298.1 having 80% identity to SEQ ID NO:35; *Methylomicrobium album* BG8 ZP_09865128.1 having 76% identity to SEQ ID NO:35; *Pseudomonas fluorescens* Pf0-1 YP 350990.1 having 25% identity to SEQ ID NO:35; and *Methylobacterium nodulans* ORS 2060 YP_002502325.1 having 24% identity to SEQ ID NO:35. Thus, the disclosure includes the use of polypeptides having from 26% to 100% identity to SEQ ID NO:35, wherein the polypeptide has bisophosphate aldolase activity. The sequences associated with the foregoing accession numbers are incorporated herein by reference.

In addition to the foregoing, the terms "triose phosphate isomerase" or "Tpi" refer to proteins that are capable of catalyzing the formation of glyceraldehyde-3-phosphate from dihydroxyacetone phosphate (DHAP), and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:36. Additional homologs include: *Rattus norvegicus* AAA42278.1 having 45% identity to SEQ ID NO:36; *Homo sapiens* AAH17917.1 having 45% identity to SEQ ID NO:36; *Bacillus subtilis* BEST7613 NP_391272.1 having 40% identity to SEQ ID NO:36; *Synechococcus elongatus* PCC 6301 YP_171000.1 having 40% identity to SEQ ID NO:36; and *Salmonella enterica* subsp. *enterica* serovar *Typhi* str. AG3 ZP_06540375.1 having 98% identity to SEQ ID NO:36. Thus, the disclosure incudes the use of polypeptides that have from 40% to 100% identity to SEQ ID NO:36 and have triose phosphate isomerase activity. The sequences associated with the foregoing accession numbers are incorporated herein by reference.

In a further step of the pathway, glyceraldehyde-3-phosphate can be converted to 1,3-bisphosphoglycerate. This enzymatic step can include a "purge valve system" (as discussed elsewhere herein). For example, glyceraldehyde-3-phosphate dehydrogenase (Gap, Tdh) converts glyceraldehyde-3-phosphate to 1,3-bisphospho-glycerate. In one embodiment, a wild-type Gap is used that uses NAD$^+$ as a cofactor (see, e.g., SEQ ID NO:37) or a mutant Gap comprising a P191D mutation (relative to the sequence of SEQ ID NO:37 and as shown in SEQ ID NO:38). In another embodiment, a mutant Gap (mGap; e.g., having a D34A/L35R/T35K mutation; relative to the sequence of SEQ ID NO:37 and as shows in SEQ ID NO:39) is used that uses NADP$^+$ as a cofactor. In yet another embodiment, a combination of Gap and mGap (GapM6) are used. A molecular purge valve comprising a water generating NADH oxidase (NoxE) that specifically oxidizes NADH, but not NADPH can be used to recycle ("purge") NADH when a wild-type gap or P118D mutant gap is used that preferentially uses NAD$^+$.

In addition to the foregoing, the terms "NADH oxidase" or "NoxE" refer to proteins that are capable of oxidizing NADH to NAD$^+$, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:18.

The pathway can further convert 1,3-bisphosphoglycerate to 3-phosphoglycerate by use of phosphoglycerate kinase (EC 2.7.2.3) (PGK; e.g., as provided in SEQ ID NO:40, or a homolog or variant thereof that is at least 80% identical thereto) which catalyzes the reversible transfer of a phosphate group from 1,3-bisphosphoglycerate (1,3-BPG) to ADP producing 3-phosphoglycerate (3-PG) and ATP. A molecular purge valve for ATP can be present to recycle ADP using, for example, a GTPase or other enzyme or a homolog or variant thereof).

The 3-phosphoglycerate can then be converted by a phosphoglycerate mutase (pgm; e.g., as provided in SEQ ID NO:41, or a homolog or variant thereof that is at least 80% identical thereto) to 2-phosphoglycerate.

An enolase (eno; e.g., as provided in SEQ ID NO:42, or a homolog or variant thereof that is at least 80% identical thereto) can then convert the 2-phosphoglycerate to phosphenolpyruvate (PEP).

A pyruvate kinase (pyk; e.g., as provided in SEQ ID NOs:43, 44, and 45, or a homolog or variant thereof that is at least 80% identical to any of SEQ ID NO:43, 44 or 45) converts PEP to pyruvate.

As mentioned above pyruvate dehydrogenase (PDH) is inhibited by products of the pathway. Thus, a PDH Bypass can be used to covert pyruvate to acetyl-coA. The PDH Bypass comprises two enzymatic steps: (i) pyruvate→acetyl phosphate catalyzed by pyruvate oxidase (e.g., PyOx from *Aerococcus viridans*; EC 1.2.3.3; see SEQ ID NO:46); and (ii) acetyal phosphate→acetyl-coA catalyzed by an acetyl phosphate transferase (aka phosphate acetyltransferase) (e.g., PTA from *G. stearothermophilus*).

As used herein a PyOx used in the composition and methods of the disclosure include sequences that are at least 85%, 90%, 95%, 98%, 99% identical to SEQ ID NO:46 and have pyruvate oxidase activity.

Phosphate acetyltransferase (EC 2.3.1.8) is an enzyme that catalyzes the chemical reaction of acetyl-CoA+phosphate to CoA+acetyl phosphate and vice versa. Phosphate acetyltransferase is encoded in *E. coli* by pta. PTA is involved in conversion of acetate to acetyl-CoA. Specifically, PTA catalyzes the conversion of acetyl-coA to acetyl-phosphate. PTA homologs and variants are known. There are approximately 1075 bacterial phosphate acetyltransferases available on NCBI. For example, such homologs and variants include phosphate acetyltransferase Pta (*Rickettsia felis* URRWXCal2) gi|67004021|gb|AAY60947.1| (67004021); phosphate acetyltransferase (*Buchnera aphidicola* str. Cc (*Cinara cedri*)) gi|116256910|gb|ABJ90592.1| (116256910); pta (*Buchnera aphidicola* str. Cc (*Cinara cedri*)) gi|116515056|ref|YP_802685.1| (116515056); pta (*Wigglesworthia glossinidia* endosymbiont of *Glossina brevipalpis*) gi|25166135|dbj|BAC24326.1|(25166135); Pta (*Pasteurella multocida* subsp. *multocida* str. Pm70) gi|12720993|gb|AAK02789.1|(12720993); Pta (*Rhodospirillum rubrum*) gi|25989720|gb|AAN75024.11 (25989720); pta (*Listeria welshimeri* serovar 6b str. SLCC5334) gi|116742418|emb|CAK21542.1|(116742418); Pta (*Mycobacterium avium* subsp. paratuberculosis K-10) gi|41398816|gb|AAS06435.1|(41398816); phosphate acetyltransferase (pta) (*Borrelia burgdorferi* B31) gi|15594934|ref|NP_212723.1|(15594934); phosphate acetyltransferase (pta) (*Borrelia burgdorferi* B31) gi|2688508|gb|AAB91518.1|(2688508); phosphate acetyltransferase (pta) (*Haemophilus influenzae* Rd KW20) gi|1574131|gb|AAC22857.1|(1574131); Phosphate acetyltransferase Pta (*Rickettsia bellii* RML369-C) gi|91206026|ref|YP_538381.1|(91206026); Phosphate acetyltransferase Pta (*Rickettsia bellii* RML369-C) gi|91206025|ref|YP_538380.1|(91206025); phosphate acetyltransferase pta (*Mycobacterium tuberculosis* F11) gi|148720131|gb|ABR04756.1|(148720131); phosphate acetyltransferase pta (*Mycobacterium tuberculosis* str. Haarlem) gi|134148886|gb|EBA40931.11 (134148886); phosphate acetyltransferase pta (*Mycobacterium tuberculosis* C) gi|124599819|gb|EAY58829.1|(124599819); Phosphate acetyltransferase Pta (*Rickettsia bellii* RML369-C) gi|91069570|gb|ABE05292.1|(91069570); Phosphate acetyltransferase Pta (*Rickettsia bellii* RML369-C) gi|91069569|gb|ABE05291.1|(91069569); phosphate acetyltransferase (pta) (*Treponema pallidum* subsp. *pallidum* str. Nichols) gi|15639088|ref|NP_218534.1| (15639088); and phosphate acetyltransferase (pta) (*Treponema pallidum* subsp. *pallidum* str. Nichols) gi|3322356|gb|AAC65090.11 (3322356), each sequence associated with the accession number is incorporated herein by reference in its entirety.

Turning again to FIG. 1B, the pathway includes the conversion of acetyl-coA to acetoacetyl-coA. The conversion of acetyl-coA to acetoacetyl-CoA is performed by an acetyl-CoA acetyltransferase (e.g., PhaA). Numerous acetyl-coA acetyltransferases are known in the art. For example, acetyl-coA acetyltransferase from *R. eutropha*. In another embodiment, the acetyl-coA acetyl transferase has an amino acid sequence that is at least 85%, 90%, 95%, 98%, 99% or 100% identical to SEQ ID NO:47.

Acetoacetyl-CoA and acetyl-Coa can be converted to HMG-CoA by the enzyme HMG-CoA synthase having an A110G mutation (see, e.g., SEQ ID NO:48) or a homolog or variant thereof having 85%-99% sequence identity thereto.

The HMG-CoA is then reduced to mevalonate by the actions of NADPH and HMG-CoA reductase (see, e.g., SEQ ID NO:49) or a homolog or variant thereof having from 85%-99% sequence identity thereto.

Mevalonate is then phosphorylated by ATP and the action of mevalonate kinase (MVK) to produce mevalonate-5-phosphate and ADP. Melavonate kinases are known in the art and include sequence that are at least 85-100% (e.g., 85%, 90%, 95%, 98%, 99%) identical to the sequence of SEQ ID NO:50 and which have mevalonate kinase activity.

The mevalonate-5-phosphate is further phosphorylated by ATP and the actions of phosphomevalonate kinase (PMVK) to produce mevalonate-5-diphosphate and ADP. Phosphomevalonate kinases are known in the art and include sequence that are at least 85-100% (e.g., 85%, 90%, 95%, 98%, 99%) identical to the sequence of SEQ ID NO:51 and which have phophomevalonate kinase activity.

Mevalonate-5-diphosphate is decarboxylated by ATP and the actions of diphosphomevalonate decarboxylase (MDC) to produce ADP, $CO_2$ and isopentyl pyrophosphate. Diphosphomevalonate decarboxylases are known in the art and include sequence that are at least 85-100% (e.g., 85%, 90%, 95%, 98%, 99%) identical to the sequence of SEQ ID NO:52 and which have diphosphomevalonate kinase activity.

Figure 7:
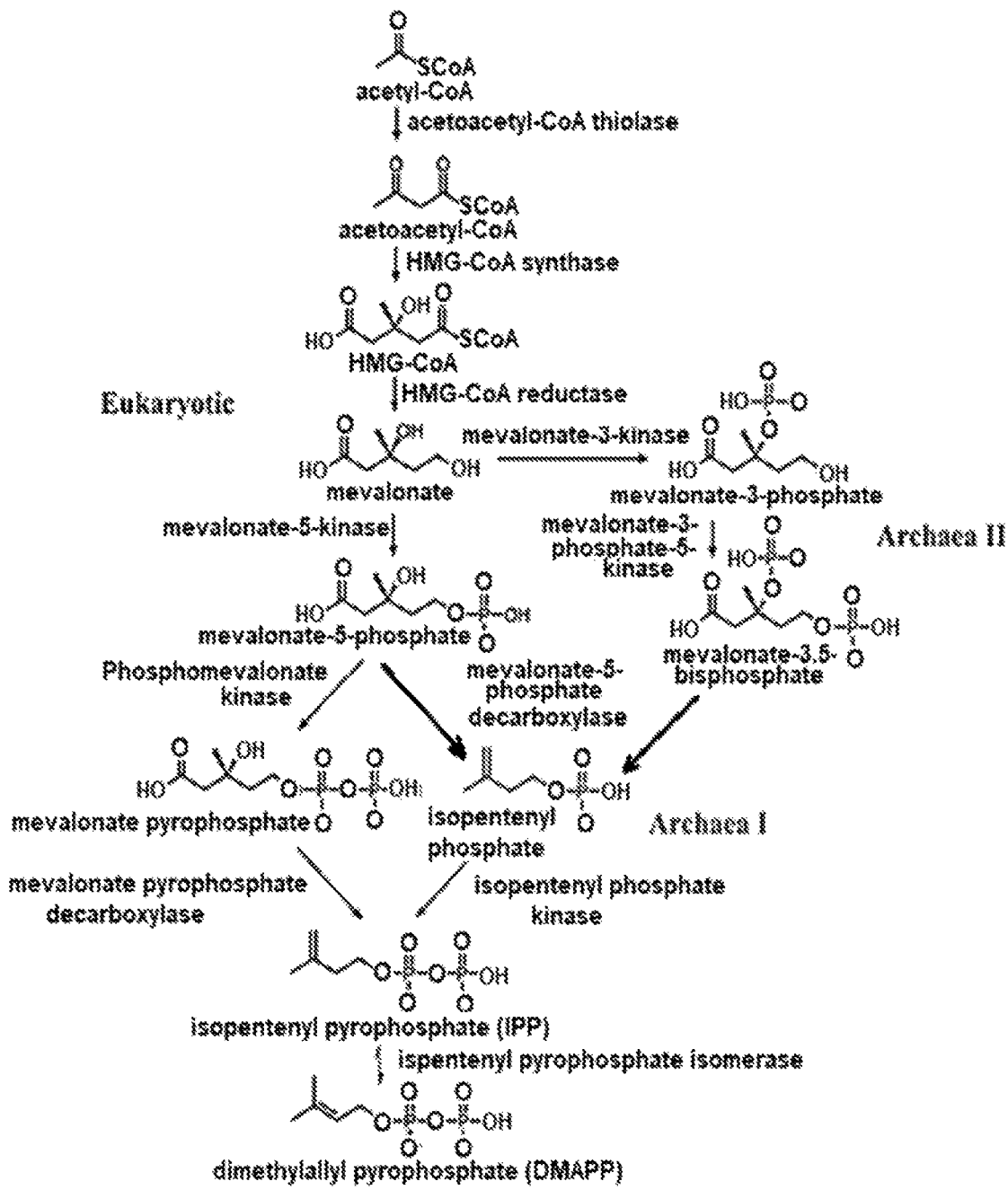
FIG. 7 shows the various canonical (Eukaryotic) and non-canonical (Archael I and II) mevalonate pathways that can be used to generate IPP/DMAPP from acetyl-CoA (or mevalonate).

Various other mevalonate pathways can be used (see, e.g., FIG. 7).

Geranyl pyrophosphate (GPP) is then formed from the combination of DMAPP and isopentyl pyrophosphate in the presence of farnesyl-PP synthase having an S82F mutation relative to SEQ ID NO:53. In one embodiment, the farnesyl-diphosphate synthase has a sequence that is at least 95%, 98%, 99% or 100% identical to SEQ ID NO:53 having an S82F mutation and which is capable of forming geranyl pyrophosphate from DMAPP and isopentyl pyrophosphate.

GPP can then be used as a substrate for a number of pathways leading to prenyl-flavinoids, geranyl-flavonoics, prenyl-stilbenoids, geranyl-stilbenoids, CBGA, CBGVA, CBDA, CBDVA, CBGVA, CBCVA, THCA and THCVA (see, e.g., FIG. 1A)

For example, with the NphB mutant, as described above, in hand (e.g., an M23 mutant), the ability to produce CBGA directly from glucose and OA was tested using the full synthetic biochemistry system, including the PDH bypass (see, FIG. 1A and FIG. 1B). The initial productivity using M23 in the system was 67 mg $L^{-1}$ $hr^{-1}$ with a final titer of 744±34 mg $L^{-1}$ of CBGA. This was 100-fold faster than CBGA production using WT NphB, and reached a titer 21-fold higher. It is noted that with the mutant NphB enzyme, maximum titers were reached within 24 hours and the production stopped, yet with the wild-type enzyme, the system ran continuously for up to 4 days suggesting that enzymes and cofactors remain active and viable for longer periods of time. It was noted that once ~500 mg $L^{-1}$ CBGA was produced, the reactions turned cloudy. The precipitate was collected and a mix of enzymes was identified in the precipitate by SDS-PAGE analysis, indicating that high-levels of CBGA in solution causes enzymes to precipitate. A more effective system was developed to remove product during the reaction.

Figure 4A:
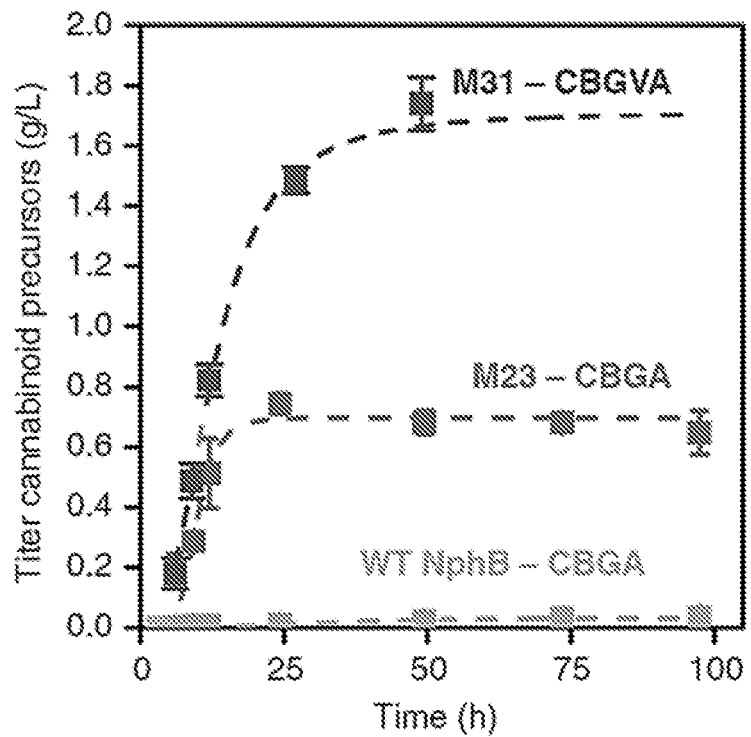
FIG. 4A-C shows the evaluation of the cell-free prenylation system for the production of various cannabinoids. (A) The cell-free enzymatic production (from glucose) of cannabinoid precursors over time. CBGA production using M23 is shown in the light green trace and WT NphB in the dark green trace. The production of CBGVA using M31 is shown in the light blue trace. The concentration of NphB for WT, M23 and M31 was fixed at 0.5 mg/mL (n=3). (B) Using a nonane flow CBGA capture system, a higher titer of CBGA (1.2 g/L) was obtained. The nonane layer was exchanged using a peristaltic pump, which circulated the nonane in the direction indicated by the arrows. This system is able to dilute the CBGA into multiple milliliters of nonane and buffer, which decreases the amount of CBGA in the reaction. (C) Production of cannabinoids over time using CBDAS. CBDA production is shown in the dark purple trace, and CBDVA production is shown in the light purple trace.
Figure 4B:
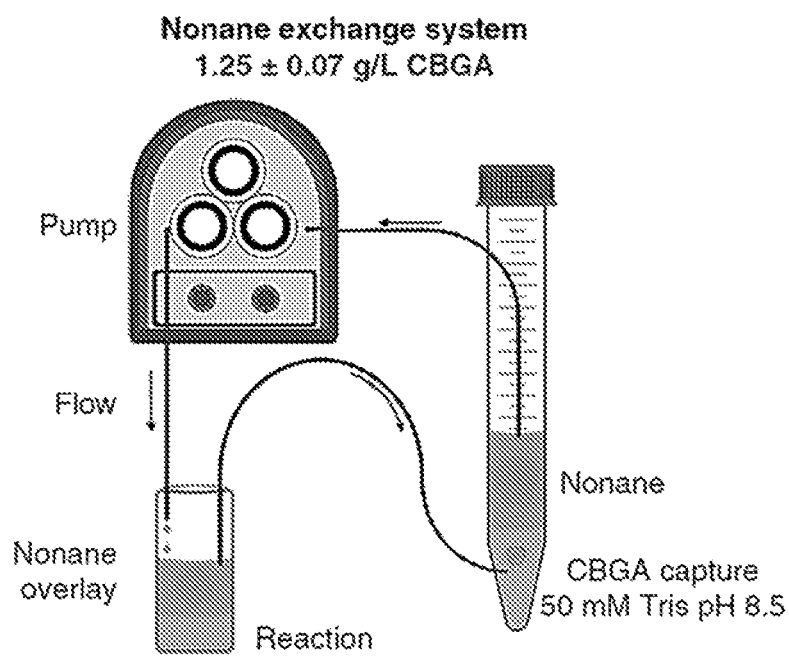
Figure 4C:
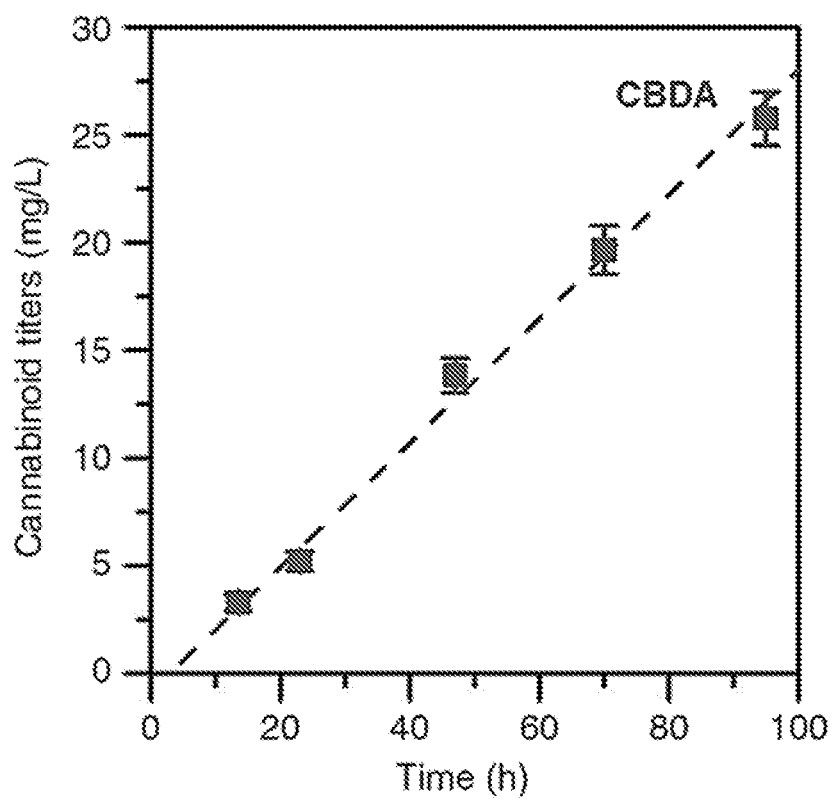

Although a nonane overlay was used in the reactions to extract CBGA, CBGA is more soluble in water than nonane, which limits the amount of CBGA that can be extracted with a simple overlay. Thus, a flow system was designed that would capture CBGA from the nonane layer and trap it in a separate water reservoir (FIG. 4*b*). By implementing this flow system a lower concentration of CBGA was maintained in the reaction vessel to mitigate enzyme precipitation. The flow system indeed improved the final titers to 1.2 g/L.

Experiments were then performed to produce the precursor of many rare cannabinoids, CBGVA, by replacing OA in the system with divirinic acid (DA) (see, e.g., FIG. 1B). The designed enzymes were first tested to determine if they would be active on a DA substrate. The two best mutants M23 and M31 were tested as well as WT NphB for their ability to produce CBGVA. The kinetic data shown in Table 2 indicated that M31 was far superior, with catalytic efficiencies 15-fold higher than M23 and 650-fold higher than WT NphB. Thus, further efforts utilized M31 to produce CBGVA from glucose and divarinic acid. As shown in FIG. 4A, CBGVA was produced at a max productivity of ~107 mg $L^{-1}$ $hr^{-1}$, and reached a final titer of 1.74±0.09 g $L^{-1}$, converting 92% of the divarinic acid added to CBGVA. The nonane flow system was not needed for the production of CBGVA because CBGVA was less potent in precipitating enzymes.

To demonstrate that the approach can ultimately be used to prepare additional cannabinoids, CBDA synthase was employed to convert CBGA into CBDA and CBGVA into CBDVA. For CBDA, the nonane overlay contained a significant quantity of CBGA, so by simply transferring the nonane overlay to a solution containing CBDA synthase, CBGA was converted into CBDA at a constant rate of 14.4±0.8 mg $L^{-1}$ $hr^{-1}$ mg total $protein^{-1}$ for 4 days.

Due to the limited solubility of CBGVA in nonane, the CBGVA was extracted and added to a reaction containing CBDA synthase. The product of the CBDA synthase was in fact CBDVA using GC-MS.

The disclosure thus provides a cell free system for the production of GPP. Further the disclosure provides a cell free approach for the production of an array of pure cannabinoids and other prenylated natural products using the GPP pathway in combination with a mutant NphB or using substrates for the mutant NphB of the disclosure. The success of this method uses the engineered prenyltransferase of the disclosure (e.g., NphB mutants as described above), which was active, highly specific and eliminated the need for the native transmembrane prenyltransferase. The modularity and flexibility of the synthetic biochemistry platform provided herein has the benefits of a bio-based approach, but removes the complexities of satisfying living systems. For example, GPP toxicity did not factor into the design process. Moreover, OA is not taken up by yeast so the approach of adding it exogenously would not necessarily be possible in cells. Indeed, the flexibility of cell free systems can greatly facilitate the design-build-test cycles required for further optimization, additional pathway enzymes and reagent and co-factor modifications.

Turning to the overall pathway of FIG. 1, the disclosure provides a number of steps catalyzed by enzymes to covert a "substrate" to a product. In some instances a step may utilize a co-factor, but some steps do not use co-factors (e.g., NAD(P)H, ATP/ADP etc.). Table 3 provides a list of enzymes, organisms and reaction amounts used as well as accession numbers (the sequences associated with such accession numbers are incorporated herein by reference).

TABLE 3

Enzymes used in the enzymatic platform

| | Enzyme Abb. | Full Name | Organism | Amount Added to Rxn (mg/mL) | Acquisition Number |
|---|---|---|---|---|---|
| 1 | Hex | Hexokinase | S. cerevisiae | 0.02 | Sigma Aldrich |
| 2 | Pgi | Glucose-6-phosphate isomerase | G. thermodenitrificans | 0.48 | ABO6822 or ARA98689.1 |
| 3 | PfkA | Phosphofructokinase | G. stearothermophilus | 0.18 | KOR92562 or P00512.2 |
| 4 | Fba | Fructose-1,6-bisphosphate aldolase | S. aureus | 0.03 | BAR10119 or PSN28048.1 |
| 5 | TpiA | Triose phosphate isomerase | G. stearothermophilus | 0.16 | KOR95273 or P00943.2 |
| 6 | Gap | Gald-3-P dehydrogenase | E. coli K12 | 0.07 | NP_416293 |
| 7 | mGap | Gald-3-P dehydrogenase D34A/L35R/T36K | G. stearothermophilus | 0.18 | NP_416293 |
| 8 | NoxE | NADH Oxidase | L. lactis | 0.25 | WP_015425842 |
| 9 | Pgk | Phosphoglycerate Kinase | G. stearothermophilus | 0.06 | NP_415276 |
| 10 | dPgm | Phosphoglycerate Mutase (2,3 BPG dependent) | E. coli K12 | 0.29 | NP_417259 |
| 11 | Eno | Enolase | E. coli K12 | 0.08 | KOR95272 or BAE76853.1 |
| 12 | PykF | Pyruvate Kinase (FBP dependent) | E. coli K12 | 0.37 | NP_416191 |
| | PDH AceE AceF Lpd | Pyruvate Dehydrogenase | E. coli K12 | 0.99 | NP_414656 NP_414657 NP_414658 |
| 13 | PyOx | Pyruvate Oxidase | A. viridans | 1 U | AG Scientific |
| 14 | PTA | Acetyl-phosphate transferase | G. stearothermophilus | 0.06 | WP_053532564 |
| 15 | PhaA | Acetyl-CoA acetyltransferase | R. eutropha | 0.12 | CAJ92573 |
| 16 | HMGS A110G | HMG-CoA Synthase A110G | E. faecalis | 0.18 | WP_010785222 |
| 17 | HMGR | HMG-CoA Reductase | E. faecalis | 0.16 | AAG02439 |
| 18 | MVK | Mevalonate Kinase | M. mazei | 0.14 | AAM31458 |
| 19 | PMVK | Phosphomevalonate Kinase | S. pneumonia | 0.2 | WP_000562411 |
| 20 | MDC | Diphosphomevalonate Kinase | S. pneumonia | 0.19 | NP_357933 |

TABLE 3-continued

Enzymes used in the enzymatic platform

| | Enzyme Abb. | Full Name | Organism | Amount Added to Rxn (mg/mL) | Acquisition Number |
|---|---|---|---|---|---|
| 21 | IDI | Isopentyl-PP Isomerase | *E. coli K12* | 0.3 | NP_417365 |
| 22 | FPPS S82F | Farnesyl-PP synthase S82F | *G. stearothermophilus* | 0.09 | KOR95521 |
| 23 | NphB | Aromatic prenyltransferase | *Streptomyces* sp. CL190 | Variable | BAE00106.1 |
| 24B | CBDAS | Cannabidiolic Acid Synthase | *C. sativa* | | AKC34419 |
| 25 | Ppase | Pyrophosphatase | *G. stearothermophilus* | 0.11 | O05724 |
| 26 | Cat | Catalase | *C. glutamicum* | 0.1 U | Sigma Aldrich |
| | GorA | Glutathione Reductase | *E. coli K12* | 0.06 | NP_417957 |

As described above, prenylation of olivetolate by GPP is carried out by the activity of the mutant NphB polypeptides described herein and above.

The disclosure provides an in vitro method of producing prenylated compounds and moreover, an in vitro method for producing cannabinoids and cannabinoid precursors (e.g., CBGA, CBGVA or CBGXA where 'X' refers to any chemical group). In one embodiment, of the disclosure cell-free preparations can be made through, for example, three methods. In one embodiment, the enzymes of the pathway, as described herein, are purchased and mixed in a suitable buffer and a suitable substrate is added and incubated under conditions suitable for production of the prenylated compound or the cannabinoids or cannabinoid precursor (as the case may be). In some embodiments, the enzyme can be bound to a support or expressed in a phage display or other surface expression system and, for example, fixed in a fluid pathway corresponding to points in the metabolic pathway's cycle.

Figure 5A:
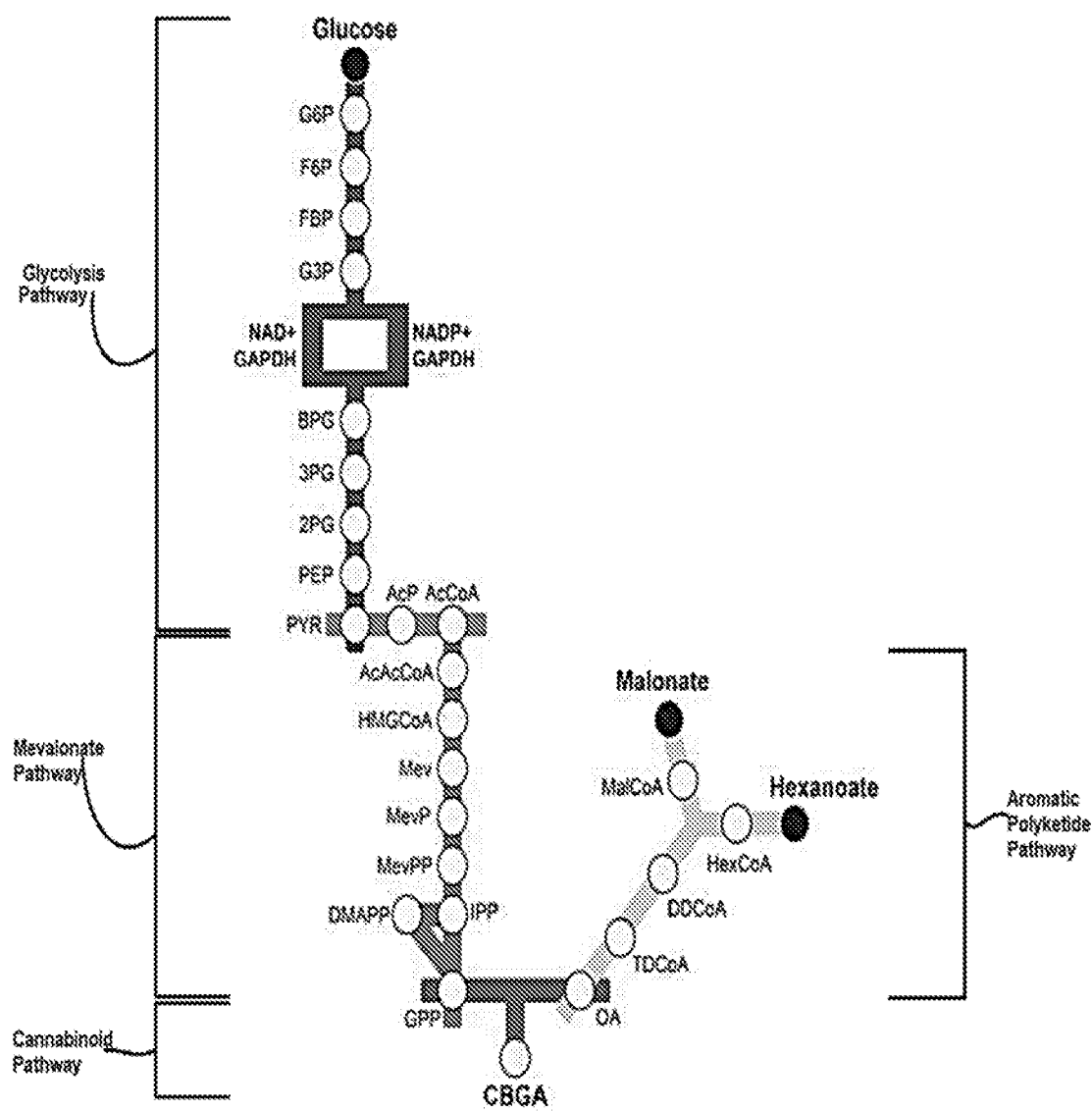
FIG. 5A-C shows Pathway schematics for the MatB and MdcA (transferase) paths. (A) This is the schematic for the MatB path. The malonyl-CoA production is ATP dependent, but otherwise not connected with the pathway. A titer is the the pathway is 12 mg/L. (B) This is the schematic for the MdcA transferase path. The malonyl-CoA production is no longer ATP dependent, and is tied in to the pyruvate oxidation path, and the mevalonate path. A titer for the system is 42 mg/L. (C) shows additional detail of exemplary steps in the polyketide module of the pathway shows in (A) and (B).
Figure 5B:
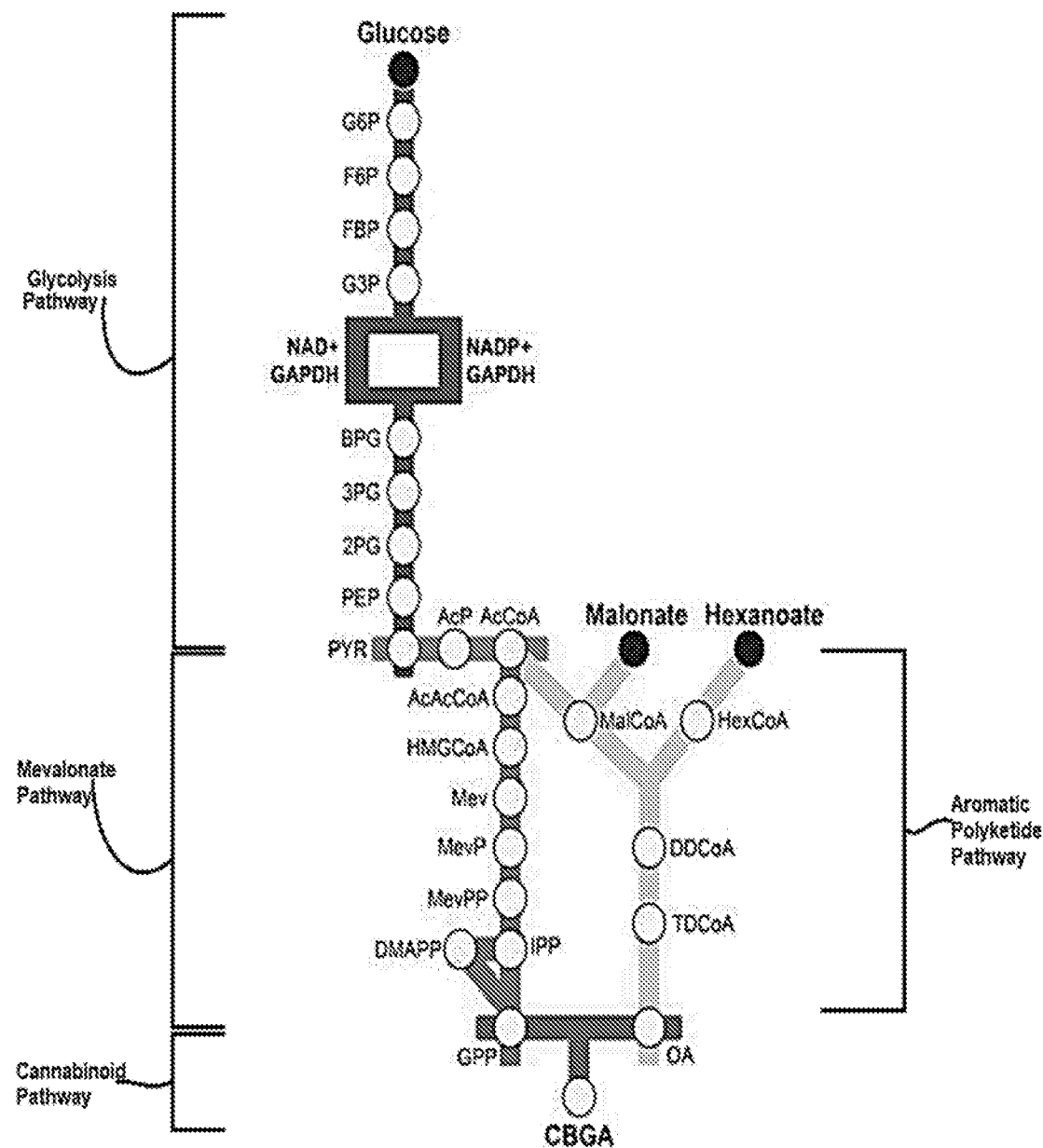
Figure 5C:
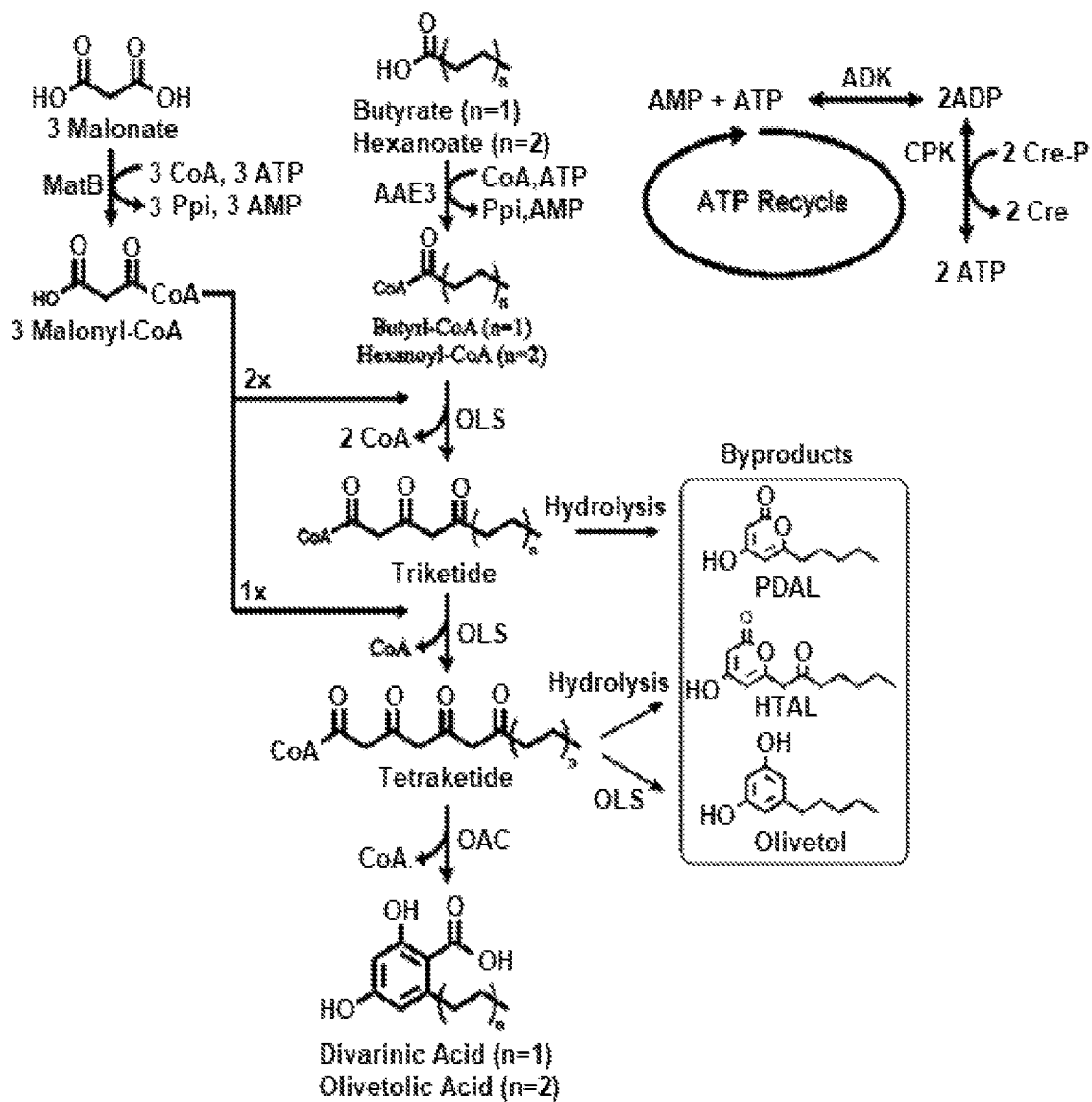
Figure 6:
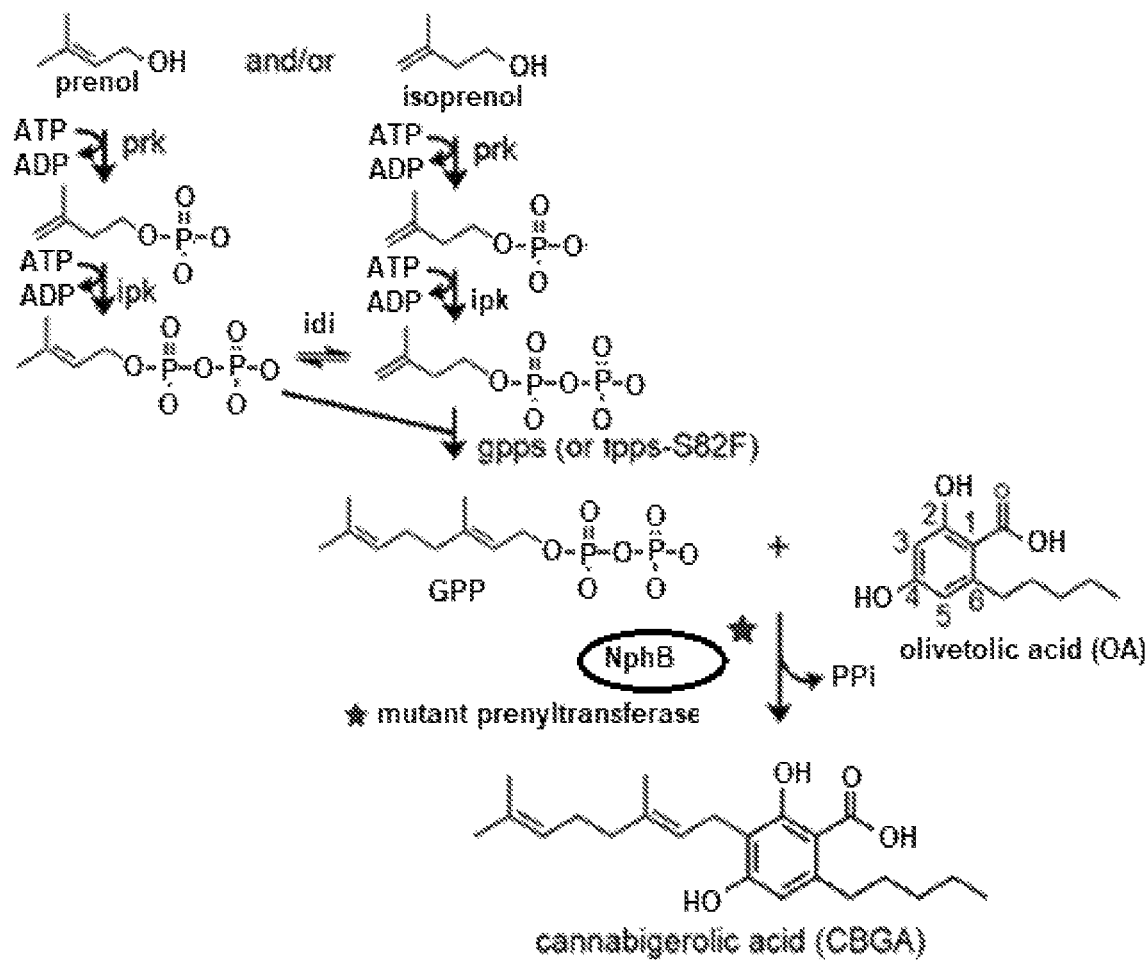
FIG. 6 shows a pathway schematic for the (iso)prenol to GPP paths. Isoprenol or prenol can be turned in to geranylpyrophosphate using ATP and necessary kinases.

FIG. 5A-B depict the pathway as various "modules" (e.g., glycolysis module, mevalonate/isoprenoid module, cannabinoid module, polyketide module). For example, the isoprenoid module produces the isoprenoid geranyl pyrophosphate (GPP) from acetyl-CoA via the mevalonate pathway. The aromatic polyketide module utilizes a Type III polyketide synthase (PKS) to convert hexanoyl-CoA and malonyl-CoA (derived from acetyl-CoA) into olivetolic acid (OA). The cannabinoid module, uses products from the isoprenoid module and the polyketide module to yield cannabigerolic acid, which is then converted into the final cannabinoid by a cannabinoid synthase.

In another embodiment, one or more polynucleotides encoding one or more enzymes of the pathway are cloned into one or more microorganism under conditions whereby the enzymes are expressed. Subsequently the cells are lysed and the lysed preparation comprising the one or more enzymes derived from the cell are combined with a suitable buffer and substrate (and one or more additional enzymes of the pathway, if necessary) to produce the prenylated compound or the cannabinoids or cannabinoid precursor. Alternatively, the enzymes can be isolated from the lysed preparations and then recombined in an appropriate buffer. In yet another embodiment, a combination of purchased enzymes and expressed enzymes are used to provide a pathway in an appropriate buffer. In one embodiment, heat stabilized polypeptide/enzymes of the pathway are cloned and expressed. In one embodiment, the enzymes of the pathway are derived from thermophilic microorganisms. The microorganisms are then lysed, the preparation heated to a temperature wherein the heat stabilized polypeptides of the pathway are active and other polypeptides (not of interest) are denatured and become inactive. The preparation thereby includes a subset of all enzymes in the microorganism and includes active heat-stable enzymes. The preparation can then be used to carry out the pathway to produce the prenylated compound or the cannabinoids or cannabinoid precursor.

For example, to construct an in vitro system, all the enzymes can be acquired commercially or purified by affinity chromatography, tested for activity, and mixed together in a properly selected reaction buffer.

An in vivo system is also contemplated using all or portions of the foregoing enzymes in a biosynthetic pathway engineered into a microorganism to obtain a recombinant microorganism.

The disclosure also provides recombinant organisms comprising metabolically engineered biosynthetic pathways that comprise a mutant nphB for the production of prenylated compounds and may further include one or more additional organisms expressing enzymes for the production of cannabinoids (e.g., a co-culture of one set of microorganism expressing a partial pathway and a second set of microorganism expression yet a further or final portion of the pathway etc.).

In one embodiment, the disclosure provides a recombinant microorganism comprising elevated expression of at least one target enzyme as compared to a parental microorganism or encodes an enzyme not found in the parental organism. In another or further embodiment, the microorganism comprises a reduction, disruption or knockout of at least one gene encoding an enzyme that competes with a metabolite necessary for the production of a desired metabolite or which produces an unwanted product. The recombinant microorganism expresses an enzymes that produces at least one metabolite involved in a biosynthetic pathway for the production of, for example, the prenylated compound or the cannabinoids or cannabinoid precursor. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of, for example, a prenylated compound or cannabinoids or cannabinoid precursors. The target enzyme is encoded by, and expressed from, a polynucleotide derived from a suitable biological source. In some embodiments, the polynucleotide comprises a gene derived from a bacterial or yeast source and recombinantly engineered into the microorganism of the disclosure. In another embodiment, the polynucleotide encoding the desired target enzyme is naturally occurring in the organism but is recombinantly engineered to be overexpressed compared to the naturally expression levels.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) *Proteobacteria*, e.g., Purple photosynthetic+non-photosynthetic Gram-negative bacteria (includes most "common" Gram-negative bacteria); (3) *Cyanobacteria*, e.g., oxygenic phototrophs; (4) Spirochetes and related species; (5) *Planctomyces*; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; and (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another (see, e.g., FIG. 1A-B). Gene products belong to the same "metabolic pathway" if they, in parallel or in series, act on the same substrate, produce the same product, or act on or produce a metabolic intermediate (i.e., metabolite) between the same substrate and metabolite end product. The disclosure provides recombinant microorganism having a metabolically engineered pathway for the production of a desired product or intermediate.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite or to express a polypeptide nor normally expressed. In an illustrative embodiment, the introduction of genetic material into a parental microorganism results in a new or modified ability to produce acetyl-phosphate and/or acetyl-CoA through through a PDH bypass using pyruvate oxidase and acetylphosphate transferase. The genetic material introduced into the parental microorganism contains gene(s), or parts of gene(s), coding for one or more of the enzymes involved in a biosynthetic pathway for the production of prenylated compounds or cannabinoids or cannabinoid precursors, and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products) or eliminates the enzyme from cell free preparations that may compete with a biosynthetic pathway developed from lysed preparations.

An "enzyme" means any substance, typically composed wholly or largely of amino acids making up a protein or polypeptide that catalyzes or promotes, more or less specifically, one or more chemical or biochemical reactions.

A "protein" or "polypeptide", which terms are used interchangeably herein, comprises one or more chains of chemical building blocks called amino acids that are linked together by chemical bonds called peptide bonds. A protein or polypeptide can function as an enzyme.

As used herein, the term "metabolically engineered" or "metabolic engineering" involves rational pathway design and assembly of biosynthetic genes, genes associated with operons, and control elements of such polynucleotides, for the production of a desired metabolite, such as an acetyl-phosphate and/or acetyl-CoA, higher alcohols or other chemical, in a microorganism. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., glucose etc.), an intermediate in (e.g., acetyl-coA), or an end product (e.g., CBDA) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon. A mutation that gives rise to a different primary sequence of a protein can be referred to as a mutant protein or protein variant.

A "native" or "wild-type" protein, enzyme, polynucleotide, gene, or cell, means a protein, enzyme, polynucleotide, gene, or cell that occurs in nature.

A "parental microorganism" refers to a cell used to generate a recombinant microorganism. The term "parental microorganism" describes, in one embodiment, a cell that occurs in nature, i.e. a "wild-type" cell that has not been genetically modified. The term "parental microorganism" further describes a cell that serves as the "parent" for further engineering. In this latter embodiment, the cell may have been genetically engineered, but serves as a source for further genetic engineering.

For example, a wild-type microorganism can be genetically modified to express or over express a first target enzyme such as a hexokinase. This microorganism can act as a parental microorganism in the generation of a microorganism modified to express or over-express a second target enzyme e.g., a fructose-1,6-bisphosphate aldolase. In turn, that microorganism can be modified to express or over express e.g., an NADH oxidase and a Gald-3-phosphate dehydrogenase (and mutants thereof), which can be further modified to express or over express a third target enzyme, e.g., a phosphoglycerate kinase etc. As used herein, "express" or "over express" refers to the phenotypic expression of a desired gene product. In one embodiment, a naturally occurring gene in the organism can be engineered such that it is linked to a heterologous promoter or regulatory domain, wherein the regulatory domain causes expression of the gene, thereby modifying its normal expression relative to the wild-type organism. Alternatively, the organism can be engineered to remove or reduce a repressor function on the gene, thereby modifying its expression. In yet another embodiment, a cassette comprising the gene sequence operably linked to a desired expression control/regulatory element is engineered in to the microorganism.

Accordingly, a parental microorganism functions as a reference cell for successive genetic modification events. Each modification event can be accomplished by introducing one or more nucleic acid molecules into the reference cell. The introduction facilitates the expression or over-expression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme into a parental microorganism.

Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells. The sequences provided herein and the accession numbers provide those of skill in the art the ability to obtain and obtain coding sequences for various enzymes of the disclosure using readily available software and basis biology knowledge.

The sequence listing appended hereto provide exemplary polypeptides useful in the methods described herein. It is understood that the addition of sequences which do not alter the activity of a polypeptide molecule, such as the addition of a non-functional or non-coding sequence (e.g., polyHIS tags), is a conservative variation of the basic molecule.

It is understood that a polynucleotide described herein include "genes" and that the nucleic acid molecules described above include "vectors" or "plasmids."

The term "polynucleotide," "nucleic acid" or "recombinant nucleic acid" refers to polynucleotides such as deoxyribonucleic acid (DNA), and, where appropriate, ribonucleic acid (RNA).

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate exemplary embodiments of the disclosure.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

The disclosure provides a number of polypeptide sequences in the sequence listing accompanying the present application, which can be used to design, synthesize and/or isolate polynucleotide sequences using the degeneracy of the genetic code or using publicly available databases to search for the coding sequences.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a starting material, but also intermediate and end product metabolites used in a pathway associated with a metabolically engineered microorganism as described herein.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For *E. coli* expression vectors, it is useful to include an *E. coli* origin of replication, such as from pUC, p1P, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

In some instances "isozymes" can be used that carry out the same functional conversion/reaction, but which are so dissimilar in structure that they are typically determined to not be "homologous".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than BLASTp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

The disclosure provides accession numbers and sequences for various genes, homologs and variants useful in the generation of recombinant microorganism and proteins for use in in vitro systems. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

It is well within the level of skill in the art to utilize the sequences and accession number described herein to identify homologs and isozymes that can be used or substituted for any of the polypeptides used herein. In fact, a BLAST search of any one of the sequences provide herein will identify a plurality of related homologs.

Culture conditions suitable for the growth and maintenance of a recombinant microorganism provided herein are known (see, e.g., "Culture of Animal Cells—A Manual of Basic Technique" by Freshney, Wiley-Liss, N.Y. (1994), Third Edition). The skilled artisan will recognize that such conditions can be modified to accommodate the requirements of each microorganism.

It is understood that a range of microorganisms can be modified to include all or part of a recombinant metabolic pathway suitable for the production of prenylated compounds or cannabinoids or cannabinoid precursors. It is also understood that various microorganisms can act as "sources" for genetic material encoding target enzymes suitable for use in a recombinant microorganism provided herein.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"), each of which is incorporated herein by reference in its entirety.

Examples of protocols sufficient to direct persons of skill through in vitro amplification methods, including the polymerase chain reaction (PCR), the ligase chain reaction (LCR), Qp-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13:563-564.

Improved methods for cloning in vitro amplified nucleic acids are described in Wallace et al., U.S. Pat. No. 5,426,039.

Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Chemicals and Reagents. Yeast hexokinase and *Corynebacterium glutamicum* catalase were purchased from Sigma Aldrich. *Aerococcus* viridians pyruvate oxidase was purchased from A.G. scientific. All cofactors and reagents were purchased from either Sigma Aldrich or Thermo Fisher Scientific, with the exception of olivetolic acid, which was purchased from Santa Cruz Biotechnology and divarinic acid, which was purchased from Toronto Research Chemicals.

Cloning and purification of enzymes. The NphB gene was purchased as a gene block from IDT DNA, and cloned into a pET 28(+) vector using the Gibson Assembly method. The remaining enzymes were amplified from genomic DNA or a plasmid, and cloned into pET28(+) using the same Gibson assembly method. All plasmids were transformed into BL21 (DE3) Gold, and enzymes expressed in LB media with 50 µg/mL kanamycin. 1 L cultures were inoculated with 2 mL of a saturated culture in the same media, and grown to an $OD_{600}$ of 0.5-0.8 at 37° C. The cultures were induced with 1 mM IPTG, and expressed at 18° C. for 16 hours. The cells were harvested by centrifugation at 2,500×g, and resuspended in ~20 mL lysis buffer: 50 mM Tris [pH 8.0], 150 mM NaCl, and 10 mM imidazole. The cells were lysed using an Emulsiflex instrument. The lysate was clarified by centrifugation at 20,000×g, and the supernatant was batch bound to 1 mL NiNTA resin for 30 mins at 4° C. The resin was transferred to a gravity flow column. The resin was washed with 10 column volumes of wash buffer: 50 mM Tris [pH 8.0], 150 mM NaCl, and 10 mM imidazole. The protein was then eluted with 2 column volumes of elution buffer: 50 mM Tris [pH 8.0], 150 mM NaCl, 250 mM imidazole and 30% (v/v) glycerol. Enzymes were flash frozen in elution buffer using liquid $N_2$, and the enzyme stocks were stored at −80° C.

PDH Cell-free Reactions. The PDH reactions were assembled in two parts. First the co-factors and substrates were combined in one tube, and the enzymes were combined in another. The reactions were initiated by mixing the co-factors and enzymes in a final volume of 200 µL. The final substrate and co-factor concentrations were as follows: 500 mM glucose, 1 mM 1,6 fructose bisphosphate, 4 mM ATP, 0.5 mM 2,3 bisphosphoglycerate, 0.5 mM $NAD^+$, 1.5 mM CoA, 1.5 mM $NADP^+$, 0.5 mM TPP, 6 mM $MgCl_2$, 10 mM KCl, 50 mM Tris [pH 8.0] and 20 mM phosphate buffer [pH 8.0], 5 mM glutathione and 0.5-5 mM 1,6 DHN. The reactions were quenched at 24 hours.

PDH Activity Assays. PDH was assayed for activity in the presence of several aromatic polyketides. The vehicle control was 1% ethanol, and the activity was compared to an assay without the aromatic polyketides. The final reaction volume was 200 µL, and contained 2 mM $NAD^+$, 2 mM CoA, 1 mM TPP, 5 mM $MgCl_2$, 5 mM KCl, 50 mM Tris pH 8.0, and 5 µL of 1.25 mg/mL PDH. The reactions were set up in a 96-well plate. The aromatic polyketides were added to a final concentration of 1 mM and the ethanol control was added to a final concentration of 1% (v/v). The plate was incubated at room temperature for 10 minutes, and the reactions were initiated with 10 µL of 100 mM pyruvate. The absorbance at 340 nm was monitored for 10 minutes using an M200 spectrometer. Because the aromatic molecules had a background absorbance at 340 nm, the reactions were blanked using the reaction mixture and aromatic molecule, but instead of initiating the reaction with pyruvate, water was added. The initial rates were determined using the initial slope of a linear fit. The amount of NADH produced per unit time was calculated using Beer's law, and the extinction coefficient of $6.22 \times 10^3$ $M^{-1}$ $cm^{-1}$. Reactions were performed in triplicate, and the average value and standard error were calculated.

PyOx/PTA Cell-free Reactions. The PyOx/PTA reactions were assembled in two pieces. First the co-factors and substrates were combined in one tube, and the enzymes were combined in another. The final co-factor and substrate concentrations in the 200 μL reaction were as follows: 500 mM glucose, 1 mM 1,6 fructose bisphosphate, 4 mM ATP, 0.5 mM 2,3 bisphosphoglycerate, 0.5 mM $NAD^+$, 1.5 mM CoA, 3 mM mM $NADP^+$, 0.5 mM TPP, 6 mM $MgCl_2$, 10 mM KCl, 50 mM Tris pH 8.0 and 50 mM phosphate buffer [pH 8.0]. The amount of enzyme added to each reaction is detailed in Table 3. The co-factors and enzymes were mixed to initiate the reaction, and a 500 μL nonane overlay was added to the top. The reactions were incubated at room temperature shaking gently on a gel shaker.

For 1,6 DHN/5-p-1,6 DHN: When the aromatic substrate was the varied component 0.5 to 5 mM of the aromatic substrate was added to the reaction, and the reactions were quenched at 24 hours. When time was the varied component, 5 mM of 1,6 DHN was added, and separate reactions were quenched at ~12, 24, 48 and 72 hours.

For olivetolate/CBGA: The optimization of the cannabinoid pathway showed that the same titers could be achieved with less glucose, so the glucose concentration was reduced to 150 mM. Additionally, increasing the $NADP^+$ concentration to 6 mM and decreasing the ATP concentration to 1 mM led to higher titers of CBGA. The olivetolate concentration was set at 5 mM. The amount of NphB added to the reaction was variable. The data shown in FIG. 2c utilized 1.5 mg/mL NphB, and the reactions were quenched at ~4, 8, 14, 24, 48, 72 and 96 hours. The data shown in FIG. 4a was achieved with 0.5 mg/mL of WT NphB and M23, and reactions were quenched at ~6, 9, 12, 24, 48, 72 and 96 hours.

For divarinic acid/CBGVA: The conditions were very similar to the general method above except 150 mM glucose, 1 mM ATP and 6 mM $NADP^+$ was used and the reactions were quenched at ~6, 9, 12, 24, and 48 hours. Additionally, the final concentration of the prenyl-transferase was 1 mg/mL, and we tested AtaPT, NovQ, and NphB with apigenin, daidzein, genistein, naringenin, and resveratrol. We also tested NphB with olivetol, olivetolate, and 1,6 DHN. The reactions were quenched at 24 h.

Quenching reactions. To quench the reactions, the aqueous and organic layer were transferred to a 1.5 mL microcentrifuge tube. The reaction vial was washed with 200 μL of ethyl acetate, which was then pooled with the reaction in the microcentrifuge tube. The samples were vortexed for 5-10 seconds and then centrifuged for 3 minutes at 13,000 rpm. The organic layer was removed, and the remaining aqueous layer was extracted 2 additional times with 200 μL of ethyl acetate. For each sample the organic extract was pooled, and then evaporated using a vacuum centrifuge. The samples were re-dissolved in methanol for HPLC analysis.

For olivetolate/CBGA: Due to the observed protein precipitation, the CBGA reactions shown in FIG. 4a were extracted in the presence of 0.12 g of urea (solid), to facilitate the extraction of CBGA. This was unnecessary for the WT NphB CBGA data in FIG. 2c because the proteins did not precipitate.

Quantification of products. The reactions were fractionated by reverse phase chromatography on a C18 column (4.6×100 mm) using a Thermo Ultimate 3000 HPLC. The column compartment temperature was set to 40° C., and the flow rate was 1 mL/min. The compounds were separated using a gradient elution with water +0.1% TFA (solvent A) and acetonitrile+0.1% TFA (solvent B) as the mobile phase. Solvent B was held at 20% for the first min. Then solvent B was increased to 95% B over 4 min, and 95% B was then held for 3 min. The column was then re-equilibrated to 20% B for three min, for a total run time of 11 min.

The cannabinoids (CBGA, CBDA, and CBDVA) were quantified using an external calibration curve derived from an analytical standard purchased from Sigma Aldrich. The 5-p-1,6-DHN and CBGVA nuclear magnetic resonance (NMR) samples were used to generate an external calibration curve because authentic standards were not available. A known concentration of the standard was dissolved in water, and then extracted using the method detailed above.

Quantify prenyl-products without authentic standards. Due to the lack of authentic standards for the prenyl-products prenyl-apigenin, prenyl-daidzein, prenyl-naringenin, prenyl-genistein, prenyl-resveratrol, and prenyl-olivetol, the prenyl-products were quantified based on substrate consumption. To generate a standard curve, serial dilutions of each aromatic substrate were subjected to the reaction mix, but to prevent product formation the prenyl-transferase was left out. Liquid chromatography-mass spectrometry was used to quantify the amount of substrate consumed by the reaction compared to the standard curve.

Electrospray ionisation time-of-flight measurements were carried out on a Waters LCT-Premier XE Time of Flight Instrument controlled by MassLynx 4.1 software (Waters Corporation, Milford, Mass.). The instrument was equipped with the Multi Mode Ionization source operated in the electrospray mode. A solution of Leucine Enkephalin (Sigma Chemical, L9133) was used in the Lock-Spray to obtain accurate mass measurements. Samples were infused using direct loop injection on a Waters Acquity UPLC system. Samples were separated on a Waters Acquity UPLC system using an Acquity BEH C18 1.7 μm column (50×2.1 mm) and were eluted with a gradient of 30-95% solvent B over 10 min (solvent A: water, solvent B: acetonitrile, both with 0.2% formic acid (vol/vol)). Mass spectra were recorded from a mass of 300-2000 Da.

NMR Spectroscopy. NMR spectroscopy was used to identify prenyl-products, and quantify 5-p-1,6-DHN.

For 1,6 DHN/5-p-1,6 DHN: The PyOx/PTA cell-free system was used to produce prenyl-DHN. 200 μL reactions were pooled, and extracted 3 times with an equivalent amount of nonane and then the nonane was evaporated. The product of the reactions was suspended in 500 μL of deuterated methanol ($CD_3OD$), with 2 mM 1,3,5-trimethoxybenzene (TMB) as an internal standard. Spectra were collected on an AV400 Bruker NMR spectrometer. The amount of the prenylated compound in the sample was determined with reference to the internal TMB standard. The proton signal from TMB (3H, s) at 6.05 ppm were compared with an aromatic proton corresponding to 5-p-1,6-DHN (1H, d) at 7.27 ppm.

For divarinic acid/CBGVA: NMR was also used to identify the product of the enzymatic system with divarinic acid as the aromatic substrate. The PyOx/PTA system was set up as detailed above, and the reactions were quenched at 24 hours. The reactions were extracted as detailed above, and analyzed on the HPLC. There was a new major peak at 6.7 minutes that was predicted to be the prenylated divarinic acid. The HPLC peak was purified, removed the solvent, and re-dissolved the pure component in 600 μL of $CD_3OD$. A proton spectrum collected with an AV500 Bruker NMR spectrometer was compared to a proton spectrum published by Shoyama et al. for CBGVA to confirm that CBGVA was the main product. Based on the paper by Shoyama et al the paper by Bohlman et al., it was concluded that the prenylation of divarinic acid occurs at the C3 carbon of divarinic acid.

Rosetta Design to modify the binding pocket of NphB to accept olivetolate. Olivetolate was placed in the active site of NphB in six different starting positions denoted as Olivetolate P1-6 in Table 4. ROSETTA was run 5 times for each olivetolate position for a total of 30 designs. The mutations predicted in each design are listed in Table 4. For each olivetolate position a consensus set of mutations (i.e., the most frequently chosen residue) was chosen to evaluate further: Consensus Group A through F (Table 4). The relative importance of each ROSSETTA suggested mutation was then evaluated. For each Consensus Group, the mutations were set back to WT residue, one at a time, and used ROSETTA to calculate the change in energy score (see Table 5). Those that caused the largest change in energy were deemed to be the most important mutants to include in the library for experimental testing.

TABLE 4

|  | Olivetolate P1 | | | | | Consensus Mutations | Olivetolate P2 | | | | | Consensus Mutations | Olivetolate P3 | | | | | Consensus Mutations |
|---|---|---|---|---|---|---|---|---|---|---|---|---|---|---|---|---|---|---|
| Prediction # | 1 | 2 | 3 | 4 | 5 | Group A | 6 | 7 | 8 | 9 | 10 | Group B | 11 | 12 | 13 | 14 | 15 | Group C |
| V49 | I | T | I | I | I | I | T | S | S | S | T | S | N |  | N | N | S | N |
| M162 |  |  |  |  |  |  |  |  |  |  |  |  | C | C | C | C | C | C |
| F213 | N | N | N | N | N | N | N | N | N | N | N | N | N | N | N | N | N | N |
| A232 | N | N | N | N | S | N | S | S | S | S | S | S |  |  |  |  |  |  |
| I234 | T | T | T | T | T | T | T | T | T | T | T | T | T | T | T | T | T | T |
| V271 | N | H | N | N | N | N | N | N | N | N | N | N | N | N | N | N | N | N |
| G286 |  |  |  |  |  |  | S | S | S |  | S | S | S |  | S | S | S | S |
| Y288 | A | D | A | A | H | A | N | N | N | N | N | N | S | A | S | S | N | S |
| L298 | I | I | I | I | I | I | R | R | R | R | R | R | R | R | R | R | R | R |
| Energy Score |  |  |  |  |  | −404 |  |  |  |  |  | −410 |  |  |  |  |  | −405 |

|  | Olivetolate P4 | | | | | Consensus Mutations | Olivetolate P5 | | | | | Consensus Mutations | Olivetolate P6 | | | | | Consensus Mutations |
|---|---|---|---|---|---|---|---|---|---|---|---|---|---|---|---|---|---|---|
| Prediction # | 16 | 17 | 18 | 19 | 20 | Group D | 21 | 22 | 23 | 24 | 25 | Group E | 26 | 27 | 28 | 29 | 30 | Group F |
| V49 | T | N | T | N | T | T | S | S | I | S | S | S | G | G | G | S | S | G |
| M162 |  |  |  |  |  |  | R | R | R | R | R | R | R | R | R | R | R | R |
| F213 | G | G | G | G | G | G | N | N | N | N | N | N | N | N | N | N | N | N |
| A232 |  |  |  |  |  |  | N | S | N | S | S | S | S | S | S | S | S | S |
| I234 | T | T | T | T | T | T | T | T | T | T | T | T | T | T | T | T | T | T |
| V271 | H | N | H | N | H | H | N | N | S | N | N | N | A | N | N | A | A | N |
| G286 |  |  |  |  |  |  |  |  |  |  |  |  |  |  |  |  |  |  |
| Y288 | D | S | N | S | D | N | N | N | N | N | N | N | N | N | N | A | A | N |
| L298 | I | I | I | I | I | I | I | A | N | A | N | A | G | V | V | G | G | V |
| Energy Score |  |  |  |  |  | −402 |  |  |  |  |  | −403 |  |  |  |  |  | −398 |

TABLE 5

| Olivetolate Position 1 | | | | | Olivetolate Position 2 | | | | |
|---|---|---|---|---|---|---|---|---|---|
| Amino Acid Position | Consensus Mutations Group A | WT | Energy Score of Mutant → WT | Energy Difference | Amino Acid Position | Consensus Mutations Group B | WT | Energy Score of Mutant → WT | Energy Difference |
| 49 | I | V | −403 | 1 | 49 | S | V | −394 | 16 |
| 213 | N | F | −391 | 13 | 219 | N | F | −402 | 8 |
| 232 | N | A | −401 | 3 | 232 | S | A | −409 | 1 |
| 234 | T | I | −382 | 22 | 234 | T | I | −404 | 6 |
| 271 | N | V | −395 | 9 | 271 | N | V | −397 | 13 |
| 288 | A | Y | −392 | 12 | 296 | S | G | −409 | 1 |
| 298 | I | L | −404 | 0 | 288 | N | Y | −401 | 9 |
|  |  |  |  |  | 298 | R | L | −408 | 2 |

| Mutations with largest effect | Mutations with largest effect |
|---|---|
| I234T | V49S |
| F213N | V271N |
| Y288A | Y288N |

| Olivetolate Position 3 | | | | | Olivetolate Position 4 | | | | |
|---|---|---|---|---|---|---|---|---|---|
| Amino Acid Position | Consensus Mutations Group C | WT | Energy Score of Mutant → WT | Energy Difference | Amino Acid Position | Consensus Mutations Group D | WT | Energy Score of Mutant → WT | Energy Difference |
| 49 | N | V | −391 | 14 | 49 | T | V | −401 | 1 |
| 162 | C | M | −404 | 1 | 213 | G | F | −98 | 304 |
| 213 | N | F | −390 | 15 | 234 | T | I | −372 | 30 |
| 234 | T | I | −400 | 5 | 271 | H | V | −398 | 4 |
| 271 | N | V | −396 | 9 | 288 | N | Y | −381 | 21 |

TABLE 5-continued

| 286 | S | G | −404 | 1 | 298 | I | L | −401 | 1 |
| 288 | S | Y | −394 | 11 | | | | | |
| 298 | R | L | −403 | 2 | | | | | |

| Mutations with largest effect | Mutations with largest effect |
|---|---|
| F213N | F213G |
| V49N | I234T |
| Y288S | Y288N |

| Olivetolate Position 5 | | | | | Olivetolate Position 6 | | | | |
|---|---|---|---|---|---|---|---|---|---|
| Amino Acid Position | Consensus Mutations Group E | WT | Energy Score of Mutant → WT | Energy Difference | Amino Acid Position | Consensus Mutations Group F | WT | Energy Score of Mutant → WT | Energy Difference |
| 49  | S | V | −398 | 5  | 49  | G | V | −383 | 15 |
| 162 | R | M | −402 | 1  | 162 | R | M | −398 | 0  |
| 213 | N | F | −318 | 85 | 213 | N | F | −388 | 10 |
| 232 | S | A | −327 | 76 | 232 | S | A | −388 | 10 |
| 234 | T | I | −398 | 5  | 234 | T | I | −388 | 10 |
| 271 | N | V | −391 | 12 | 271 | N | V | −390 | 8  |
| 288 | N | Y | −390 | 13 | 288 | N | Y | −367 | 31 |
| 298 | A | L | −394 | 9  | 298 | V | L | −397 | 1  |

| Mutations with largest effect | Mutations with largest effect |
|---|---|
| F213N | Y288N |
| A232S | V49G |
| Y288N | |

To model the olivetolic acid, the 4MX.sdf 3-D structure of olivetolate from the 5B09 crystal structure was used and hydrogen atoms were added to the structure assuming pH 7 using open Babel 2.3.1. A rotamer library was generated for olivetolic acid using the Bio Chemical Library (BCL) molecule: Conformer Generator 3.5 using the PDB library. Finally, the aromatic bonds were manually annotated into the file before generating the parameter file read by Rosetta using the script main/source/python/public/molfile_to_params.py in the Rosetta 3.7 release. The parameter file for geranyl s-thioldiphosphate (GST) was generated without a rotamer library using the GST.sdf file from the 1ZB6 crystal structure. The olivetolic acid molecule was then manually placed into the co-crystal structure of NphB with GST and DHN (1ZB6) with the DHN and crystallographic waters removed using pymol. The olivetolic acid was placed in 6 different positions in the active site with the plane of the olivetolate aromatic ring parallel to the GST alkyl tail and the desired prenylation site 3.7 angstroms away from the eventual carbocation mirroring the placement of DHN in the 1ZB6 crystal structure. Residues 49, 162, 213, 224, 232, 233, 234, 271, 286, and 288 were allowed to be any amino acid during the Rosetta design with other sidechains held in a fixed position and the backbone fixed. The designed residues were in direct contact with the olivetolate and not in direct contact with GST. The fixed backbone script main/source/bin/fixbb.static.linuxgccrelease from the Rosetta 3.7 release was run with the all possible rotamers (-ex4), using the input sidechains (-use_input_sc), sidechains minimized after design (minimize_sidechains), the linear memnode interaction graph (-linmem_ig 10), and both with and without the ligand weighted score function (-score:weights ligand). From the identical starting point each design was run 5 times using the -nstruct input. From the set of mutations suggested by Rosetta, the mutations that occurred most frequently and contributed most to the Rosetta score function were chosen, creating a library of 22 mutants for experimental testing.

Initial NphB mutant library screening. For screening of the initial library, small scale expression and purifications were performed. 25 mL of LB media was inoculated with 25 uL of a saturated culture of BL21 DE3 Gold harboring the NphB expression plasmid. The cultures were incubated at 37° C. until the $OD_{600}$ reached 0.4-0.6. The expression of the NphB constructs were induced with the addition of 1 mM IPTG, followed by incubation for 18 hours at 18° C. Cells were harvested by centrifugation at 2500×g. The pellets were re-suspended in 500 µL of lysis buffer: 50 mM [Tris pH 8.0], 150 mM NaCl, and 5 mM imidazole and lysed by sonication. The cell lysate was clarified by centrifugation at 20,000×g for 10 minutes at 4° C., and the supernatant was incubated at 4° C. with 50 µL of NiNTA resin. A 96-well spin column plate was used to purify the NphB constructs. The supernatant/resin was applied to the column and centrifuged for 2 mins at 500×g. 500 µL of lysis buffer was then added, and the plate was centrifuged again for 1 minute at 500×g. The protein was eluted using 200 µL of elution buffer (50 mM Tris [pH 8.0], 150 mM NaCl, 250 mM imidazole and 30% (v/v) glycerol).

The enzymes were assayed under the following conditions: 2.5 mM geranyl pyrophosphate, 5 mM olivetolate, 5 mM $MgCl_2$, 50 mM Tris pH 8.0, ~0.1 mg/mL NphB mutant in a final volume of 100 µL. All enzymes were first diluted to 0.5 mg/mL using elution buffer so the final concentration of imidazole was the same in each reaction. The reactions were incubated for 12 hours at room temperature, then extracted 3 times with 100 µL of ethyl acetate. The organic extract was pooled for each reaction and the solvent was removed using a vacuum centrifuge. The samples were redissolved in 100 µL of methanol and subjected to HPLC analysis.

Focused NphB mutant library screening. For the focused library, 1 L scale expression and purification of the NphB constructs as described above was performed. The enzymes were assayed under the following conditions: 2.5 mM GPP, 5 mM olivetolate, 5 mM $MgCl_2$, 50 mM Tris pH 8.0 and ~1 mg/mL of NphB enzyme in a final volume of 100 µL. The reactions were incubated at room temperature for 1 hour. 40 µL of each reaction was quenched in 80 µL of acetonitrile. The samples were centrifuged for 5 minutes at 13,000 rpm, to remove precipitated proteins. The supernatant was analyzed using HPLC as described above.

Enzyme Kinetic Parameters. The reactions were set up under the following conditions: 50 mM Tris [pH 8.0], 2.5 mM GPP, 5 mM $MgCl_2$, ~27 μM enzyme, and olivetolate or divarinic acid was varied from 0.1 mM to 6 mM in a final volume of 200 μL. 40 μL of the reaction was quenched in 80 μl acetonitrile+0.1% TFA, at the time intervals detailed below. The reactions were centrifuged for 5 minutes at 13,000-16,060×g to pellet the protein, and the supernatant was analyzed using the HPLC method detailed above. The initial rate was plotted vs the concentration of substrate, and fit with the Michaelis-Menten equation to determine the kinetic parameters $k_{cat}$ and $K_M$ (OriginPro). Each Michaelis-Menten curve was performed in triplicate. The average and standard deviation of the kinetic parameters are reported.

For olivetolate/CBGA: For WT, M1, M10 and M30 the time course was 3, 6, 9, and 12 minutes. For mutant 25 the reactions were quenched at 1, 2, 4 and 8 minutes, and for M31 the reactions were quenched at 1, 2, 4 and 6 minutes.

For divarinic acid/CBGVA: For M31, the time course was 0.5, 1, 1.5 and 2 minutes. For M23, the time course was 5, 10, 15 and 20 minutes, and for WT NphB the time course was 8, 16, 24 and 32 minutes. The enzyme concentration for the mutants was ~27 μM, and the concentration of WT NphB was ~35 μM.

GC-MS characterization of isomer profile from WT NphB and M23. Samples were dissolved in 200 μL of ethyl acetate. GC-MS measurements were carried out using an Agilent Model 7693 Autosampler, 7890B Gas Chromatograph, and 7250 Q-TOF Mass Selective Detector in the Electron Ionization mode. Sample injection was carried out in split mode with inlet temperature set to 280° C. Separation was carried out on an Agilent HP5-MS column with dimensions 30 m×250 μm×0.25 μm. Ultra High Purity Grade He (Airgas) was used as carrier gas with the flow set to 1.1 mL/min in constant flow mode. The initial oven temperature was set to 120° C. for 1 min followed by a 20° C./min ramp to a final temperature of 300° C. which was maintained for 4 min. A 3.0 min solvent delay was used. EI energy was set to 15 eV. The MSD was set to scan the 50-500 m/z range. Data collection and analysis were performed using Mass Hunter Acquisition and Qualitative Analysis software (Agilent).

Due to the increased temperature of the GC inlet, CBGA undergoes spontaneous decarboxylation as described by Radwan et al, resulting in an M+ ion at 316 m/z. The retention time corresponding to the 316 m/z ion for the CBGA standard was 10.48 minutes.

Nonane-flow system for the extraction of CBGA from solution. A PyOx/PTA reaction was set up as detailed above. A 500 μL nonane overlay was added to the reaction in a 2 ml glass vial which was covered with 2 layers of breathable cell culture film. 2 needles were inserted into a 15 mL falcon tube at the ~750 μL mark and the 3.5 mL mark. Luer locks to tubing connectors were connected to the needles and Viton tubing was connected to the other end of the luer lock. Needles were connected to the other end of the tubing via a luer lock connector and inserted through the mesh covering so they were only touching the nonane layer and not the reaction. 2 mL of Tris buffer [pH 8.5] was added to the 15 mL conical tube, and 6 mL of nonane was added. The nonane was pumped through the system using a peristaltic pump such that the nonane flowed from the top of the reaction, through the buffered solution. The nonane pumped into the reservoir separated into the top layer of the 15 mL conical tube. The nonane from the top of the 15 mL conical tube was pumped into the top of the reaction vial. This essentially diluted the CBGA throughout the system driving the diffusion of CBGA into the nonane layer and out of the reaction.

Cloning CBDAS. A gene block of CBDAS was ordered from IDT codon optimized for *Pichia pastoris*. The signal sequence was removed by PCR amplifying from the 28$^{th}$ residue of the protein sequence (NPREN . . . ) through the end of the protein, with overhangs compatible with the pPICZa vector. The PCR product was cloned into the pPICZa vector digested with EcoRI and XbaI using the Gibson cloning method. The product of the assembly reaction was transformed into BL21 Gold (DE3) cells a clone with the correct sequence isolated. The plasmid was digested with PmeI for 2 hours, and then purified using the Qiagen PCR purification protocol. The plasmid was transformed into *Pichia pastoris* X33 using electroporation. Immediately following electroporation, the cells were incubated in 1 mL of cold 1 M sorbitol and 1 mL of YPD media without shaking for 2 hours. The cells were plated on YPDS plates with 500 μg/mL of zeocin. Colonies were screened using PCR for the presence of the CBDAS gene between the AOX1 promoter and terminator. For screening, the colonies were re-suspended in 15 μL of sterile water and 5 μL of the resuspended colony was transferred into a PCR tube with 0.2% SDS. The samples were heated for 10 minutes at 99° C., and then 1 μL was used as the template for PCR. Six colonies with positive colony PCR hits were screened for the expression of CBDAS.

CBDAS Expression Test. The six colonies were grown overnight at 30° C. to obtain a saturated culture. The overnight cultures were used to inoculate a 25 mL culture in BMGY media and grown to an OD of ~2. The cells were harvested by centrifugation at 2,000×g for 10 minutes. The cell pellet was re-suspended in 90 mL of BMMY media, and incubated at 30° C. for 5 days. Each day, 1 mL of the culture was removed for SDS-PAGE analysis, and 500 μL of methanol was added. On day 3 the cultures were screened for CBDAS activity. The assay conditions were as follows: 100 μL of 200 mM citrate buffer, 100 μM CBGA, 5 mM $MgCl_2$, 5 mM KCl, 1 mM FAD and 50 μL of the expression media in a final volume of 200 μL. The reactions were incubated overnight at room temperature and then extracted 3 times with 200 μL of ethyl acetate. The ethyl acetate extractions were pooled for each sample, and removed using a vacuum centrifuge. The samples were re-suspended in 200 μL of methanol and analyzed by HPLC. All clones produced active CBDAS.

The culture from three clones (~300 mL total), was collected to obtain CBDAS activity. The cells were pelleted by centrifuging at ~3,000×g for 20 minutes at 4° C. Then the supernatant was passed through a 0.22 μm filter. The media was concentrated and buffer exchanged into 100 mM citrate buffer pH 5.0 using a 50,000 MWCO protein concentrator from Millipore. The total protein in the media concentrate was determined to be 0.4 mg/mL using a Bradford assay, for a total yield of ~5 mg/L total protein.

Production of CBDVA and CBDA. To convert the precursors CBGA and CBGVA into CBDA and CBGVA respectively, a secondary reaction was set up with CBDAS synthase.

For CBGA/CBDA: A PyOx/PTA enzymatic system was set up as detailed above to produce CBGA. After 24 hours 200 μL of the nonane overlay from the CBGA reaction was transferred to a CBDAS reaction vessel. In the aqueous layer: 50 mM Hepes [pH 7.0], 5 mM $MgCl_2$, 5 mM KCl, 25 μM FAD, 0.1 mg/mL CBDAS concentrate. The reaction was incubated at 30° C. with gentle shaking. Reactions were quenched at 12, 24, 48, 72 and 96 hours.

For CBGVA/CBDVA: HPLC purified CBGVA was converted to CBDVA. The final reaction volume was 200 µL, with 50 mM Hepes [pH 7.0], 5 mM MgCl$_2$, 5 mM KCl, 25 µM FAD and 0.1 mg/mL (total protein) of CBDAS concentrate. A 200 µL nonane overlay was added, and the reactions were incubated at 30° C. with gentle shaking. The reactions were quenched at ~24, 48, 72 and 96 hours.

MatB Activity Assay. A coupled enzymatic assay was used to determine the activity of malonyl-CoA synthetase (MatB) from *R. palustris* (see, e.g., SEQ ID NO:82-83) in the presence of OA and DA. The reaction conditions were: 2.5 mM malonate, 2 mM ATP, 1 mM CoA, 2.5 mM phosphoenolpyruvate (PEP), 1 mM NADH, 5 mM MgCl$_2$, 10 mM KCl, 0.35 mg/mL ADK, 0.75 µg/mL MatB, 1.6 units of PK and 2.5 units of LDH, and 50 mM Tris [pH 8.0]. Background ATPase activity was controlled for by leaving out the substrate (malonate), and either 1% ethanol, 250 µM or 5 mM OA or 5 mM DA was added to the remaining reactions. The activity of MatB was determined by monitoring decreasing absorbance at 340 nm due to NADH consumption using an M2 SpectraMax. To ensure that MatB was limiting at 5 mM OA or DA, MatB was doubled to 1.5 µg/mL. The rate of the reaction doubled suggesting that MatB was the limiting component in the system. The rate of NADH consumption at 5 mM OA and 5 mM DA was normalized to the 1% ethanol control.

AAE3 Activity Assay. A coupled enzymatic assay, similar to the one above was used to determine the activity of acyl activating enzyme 3 (AAE3) (see, e.g., SEQ ID NOs: 70-71 and homologs-SEQ ID NO:72-75) in the presence of OA and DA. The conditions were the same as the MatB assay with the following modifications: 2.5 mM hexanoate was added in lieu of malonate, and 15 µg/mL of AAE3 was added in lieu of MatB. To ensure that AAE3 was limiting, AAE3 was doubled in the presence of 5 mM OA or DA. The rate of the reaction doubled indicating AAE3 is limiting.

ADK Activity Assay. A coupled enzymatic assay was used to determine the activity of adenylate kinase (ADK) (see, e.g., SEQ ID NO: in the presence of OA and DA. The conditions were similar to the MatB assay, with the following modifications: 2 mM AMP was added in lieu of malonate, CoA was not added, and 0.001 mg/mL of ADK was added. To ensure that ADK was the limiting reagent at 5 mM OA and DA, the amount of ADK was doubled. The 2-fold increase in rate suggested that ADK was the limiting factor.

CPK Activity Assay. A coupled enzymatic assay was used to determine the activity of creatine kinase (CPK) in the presence of OA or DA. The reaction conditions were: 5 mM Creatine Phosphate, 2 mM ADP, 5 mM glucose, 2 mM NADP$^+$, 5 mM MgCl$_2$, 5 mM KCl, 0.3 mg/mL Zwf, 0.1 mg/mL Sc Hex and 0.08 units CPK. The positive control reaction contained 1% ethanol, and either 5 mM of OA or DA was added to the remaining reactions. The absorbance of NADPH at 340 nm was monitored. To ensure that CPK was limiting was doubled at 5 mM OA and 5 mM DA. The resulting rate doubled, which indicates CPK is limiting even at high OA and DA.

OLS Activity Assay. Olivetol synthase (OLS) (see, e.g., SEQ ID NO:76-77) was assayed by setting up the following conditions: 200 µM malonyl CoA, 100 µM hexanoyl-CoA, 0.65 mg/mL OAS, in either 50 mM citrate buffer pH 5.5 or 50 mM Tris buffer pH 8.0. The reactions were initiated by the addition of OAS, and then they were quenched at 30 minutes by adding 150 µL of methanol to the 50 µL reaction. The samples were centrifuged at ~16,000×g for 2 minutes to pellet the proteins. The supernatant was analyzed using the HPLC.

For the inhibition experiments the conditions were altered to: 1 mM malonyl-CoA, 400 µM hexanoyl-CoA in 50 mM citrate buffer, pH 5.5 in a final volume of 200 µL. Either 1% ethanol, 250 µM OA or 1 mM DA was added to the reaction, and then the reactions were initiated by adding 0.65 mg/mL OLS. 50 µL aliquots were quenched at 2, 4, 6 and 8 minutes in 150 µL of methanol. The reactions were vortexed briefly and centrifuged at 16,000×g for 2 minutes to pellet the proteins. The supernatant was analyzed by HPLC. The raw peak areas of HTAL, PDAL and olivetol were summed and plotted against time to determine the rate. The rate of the OA supplemented reaction and the DA supplemented reaction were normalized to the ethanol control.

OLS/OAC Activity Assay. To produce OA, the same OLS conditions specified above were used, but olivetolic acid cyclase (OAC) (see, e.g., SEQ ID NO:78-79) was added to the reaction at 0.6 mg/mL. The reactions were quenched and analyzed in the same manner as the OLS assay. Acetyl-phosphate and BSA were added to the assays individually 5 mM-40 mM AcP and 10-30 mg/mL BSA final concentration.

Full pathway set up. The enzymes used in this study and the final concentration (mg/mL) can be found in Table 6 for the MatB path and Table 7 for the MdcA path. For the MatB path, the cofactors were added at the following concentrations: 150 mM glucose, 1 mM fructose bisphosphate, 2 mM ATP, 0.25 mM NAD+, 3 mM NADP+, 2 mM CoA, 0.25 mM 2,3-bisphosphoglycerate, 6 mM MgCl2, 10 mM KCl, 0.5 mM thiamine pyrophosphate, 50 mM phosphate pH 8.0, 5 mM hexanoate, 15 mM malonate, 5 mM creatine phosphate, and 50 mM Tris, pH 8.0. The reactions were initiated by the addition of the enzymes listed in Table 6. The reaction was incubated overnight at room temperature, and the reaction was quenched and extracted 3 times with 200 µL of ethyl acetate. The ethyl acetate was removed using a vacuum centrifuge. The sample was dissolved in 200 µL of methanol and analyzed using HPLC.

TABLE 6

Enzymes used in the full cannabinoid MatB pathway, with final enzyme concentrations MatB Pathway

| Enzyme | mg/mL |
|---|---|
| Glycolysis | |
| Sc Hex | 0.02 |
| Gs PfkA | 0.32 |
| Sa Fba | 0.18 |
| Gs TpiA | 0.04 |
| Gs Pgi | 0.17 |
| Ec GapA | 0.05 |
| Gs GapM6 | 0.18 |
| Gs Pgk | 0.03 |
| Ec dPgm | 0.38 |
| Ec Eno | 0.08 |
| Ec PykF | 0.56 |
| Av PyOx | 1 unit |
| Gs PTA | 0.06 |
| Ll NoxE | 0.25 |
| Ca Catalase | 125 units |
| Mevalonate | |
| Re PhaA | 0.12 |
| Ef HMGS A110G | 0.22 |
| Ef HMGR | 0.58 |
| Mm MVK | 0.16 |
| Spne PMVK | 0.23 |

TABLE 6-continued

Enzymes used in the full cannabinoid MatB
pathway, with final enzyme concentrations
MatB Pathway

| Enzyme | mg/mL |
|---|---|
| Spne MDC | 0.22 |
| Ec IDI | 0.23 |
| Gs FPPS S82F | 0.04 |
| SCL190 NphB | 0.45 |
| Gs Ppase | 0.16 |
| Olivetolate | |
| Rp MatB | 0.03 |
| Cs AAE3 | 0.18 |
| Cs OLS | 0.25 |
| Cs OAC | 0.87 |
| Gt ADK | 0.07 |
| Creatine Kinase | 2 units |

TABLE 7

Enzymes used in the full cannabinoid MdcA
pathway with final enzyme concentrations
Transferase Pathway

| Enzyme | mg/mL |
|---|---|
| Glycolysis | |
| Sc Hex | 0.02 |
| Gs PfkA | 0.32 |
| Sa Fba | 0.18 |
| Gs TpiA | 0.04 |
| Gs Pgi | 0.17 |
| Ec GapDH | 0.05 |
| Gs GapM6 | 0.18 |
| Gs Pgk | 0.03 |
| Ttg dPgm | 0.09 |
| Ec EnoNH | 0.08 |
| Gs PykA | 0.13 |
| Av PyOx | 1 unit |
| Gs PTA | 0.06 |

TABLE 7-continued

Enzymes used in the full cannabinoid MdcA
pathway with final enzyme concentrations
Transferase Pathway

| Enzyme | mg/mL |
|---|---|
| Ll NoxE | 0.25 |
| Ca Catalase | 125 units |
| Mevalonate | |
| Re PhaA | 0.12 |
| Ef HMGS-A110G | 0.43 |
| Ef HMGR | 0.58 |
| Mm MVK | 0.16 |
| Spne PMVK | 0.23 |
| Spne MDC | 0.19 |
| Ec IDI-CH | 0.23 |
| Gs FPPS S82F | 0.04 |
| SCL190 NphB 31 | 0.68 |
| Gs PPase | 0.16 |
| Olivetolate | |
| Gs MdcA | 0.18 |
| Cs AAE3 | 0.12 |
| Cs OAS | 0.60 |
| Cs OAC | 0.87 |
| Gt ADK | 0.07 |
| Creatine Kinase | 2 units |

The enzymes for the MdcA path can be found in Table 7. The MdcA reaction was set up under the same cofactor conditions specified above with the following changes: 3 mM ATP, 0.25 mM AMP, 25 mM creatine phosphate and no Tris buffer.

The pathway of both the MatB and MdcA pathway are provided in FIG. 5A-B.

Certain embodiments of the invention have been described. It will be understood that various modifications may be made without departing from the spirit and scope of the invention. Other embodiments are within the scope of the following claims.

What is claimed is:

1. A recombinant polypeptide comprising a sequence selected from the group consisting of:
   (a) SEQ ID NO:30 and having at least a Y288X mutation, wherein X is A, N, S or V;
   (b) SEQ ID NO:30 having at least a Y288X mutation, wherein X is A, N, S or V, and at least one other mutation selected from V49Z$_1$, F213Z$_2$, A232S, I234T, V271Z$_3$ and/or G286S, wherein Z$_1$ is S, N, T or G, Z$_2$ is H, N or G and Z$_3$ is N or H;
   (c) a sequence of (a) or (b) further comprising from 1-20 conservative amino acid substitutions and having prenyltransferase (NphB) activity; and
   (d) a sequence that is at least 95%, 98% or 99% identical to SEQ ID NO:30 and which has at least the mutations of (a) or (b);
   wherein the polypeptide of (a)-(d) can perform prenylation reactions.

2. The recombinant polypeptide of claim 1, wherein the polypeptide comprises SEQ ID NO:30 and has a mutation selected from the group consisting of:
   (i) V288A;
   (ii) Y288N;
   (iii) Y288N and F213H;
   (iv) Y288A and F213N;
   (v) Y288N and V49S,
   (vi) Y288S and V49N;
   (vii) Y288A and V49S,
   (viii) Y288N and G286S;
   (ix) Y288N, F213N and V49G;
   (x) Y288A, F213N and I234T;
   (xi) Y288S, F213N and V49N;
   (xii) Y288A, F213N and A232S;
   (xiii) Y288N, F213G and V49T,
   (xiv) Y288N, F213N, V49S and V271N;
   (xv) Y288N, F213G, V49T and V271I-1;
   (xvi) Y288A and G286S;
   (xvii) Y288A, G286S and A232S;
   (xviii) Y288A, G286S, A232S and F213H;
   (xix) Y288V and G286S;
   (xx) Y288A and A232S; and
   (xxi) Y288V and A232S.

3. The recombinant polypeptide of claim 1 having a sequence of SEQ ID NO:30 and having Y288A and G286S mutations.

4. The recombinant polypeptide of claim 1, wherein the prenylation reaction comprises the production of CBGA from GPP and Olivetolate or cannabigerovarinic acid (CBGVA) from geranylpyrophosphate (GPP) and divirinic acid or CBGXA from GPP and a 2,4-dihydroxy benzoic acid or a compound of Formula I:

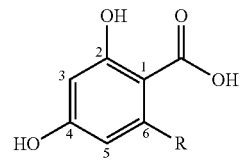

Formula I wherein R is H, CH$_3$ or X, wherein X is selected from a halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted (C$_1$-C$_{10}$)alkyl, an optionally substituted (C$_2$-C$_{10}$)alkenyl, an optionally substituted (C$_2$-C$_{10}$)alkynyl, an optionally substituted (C$_1$-C$_{10}$)heteroalkyl, an optionally substituted (C$_2$-C$_{10}$)hetero-alkenyl, an optionally substituted (C$_2$-C$_{10}$)hetero-alkynyl, an optionally substituted (C$_3$-C$_{10}$)cycloalkyl, an optionally substituted aryl, and an optionally substituted heterocycle.

5. A composition comprising a recombinant pathway comprising a polypeptide of claim 1 and a plurality of enzymes that convert glucose to Geranylpyrophosphate (GPP).

6. The composition of claim 5 further comprising a pyruvate dehydrogenase bypass enzymatic pathway comprising a pyruvate oxidase and an acetyl phosphate transferase.

7. The composition of claim 4, wherein the pathway comprises a purge valve that recycles NADH/NAD.

8. The composition of claim 5, wherein the pathway comprises the following enzymes:
   (i) hexokinase (Hex);
   (ii) Glucose-6-phosphate isomerase (Pgi);
   (iii) Phosphofructokinase (Pfk);
   (iv) Fructose-1,6-bisphosphate aldolase (Fba);
   (v) Triose phosphate isomerase (Tpi);
   (vi) Gald-3-P dehydrogenase (Gap);
   (vii) a mutant Gald-3-P dehydrogenase (mGap);
   (viii) NADH Oxidase (Nox)

(ix) Phosphoglycerate Kinase (Pgk)
(x) Phosphoglycerate Mutase (2,3 BPG dependent or Mn2+ dependent) (dPgm or iPgm);
(xi) Enolase (eno);
(xii) Pyruvate Kinase (FBP dependent/pykF or AMP dependent/pykA);
(xiii) Pyruvate Oxidase (PyOx);
(xiv) Acetyl-phosphate transferase (PTA);
(xv) Acetyl-CoA acetyltransferase (PhaA);
(xvi) HMG-CoA Synthase (HMGS);
(xvii) HMG-CoA Reductase (HMGR);
(xviii) Mevalonate Kinase (MVK);
(xix) Phosphomevalonate Kinase (PMVK);
(xx) Diphosphomevalonate decarboxylase (MDC);
(xxi) Geranyl-PP synthase (GPPS) or Farnesyl-PP synthease mutant S82F; and
(xxii) a mutant aromatic prenyltransferase.

9. The composition of claim 5, wherein the pathway is supplemented with ATP and olivetolate and the pathway produces a cannabinoid precursor.

10. The composition of claim 9, wherein the pathway further comprises a cannabidiolic acid synthase.

11. The composition of claim 10, wherein the pathway produces cannabidiolic acid.

12. A recombinant pathway composition comprising the polypeptide of claim 1 and a plurality of enzymes that convert (iso)prenol to geranylpyrophosphate (GPP).

* * * * *